(12) United States Patent
Frohberg et al.

(10) Patent No.: US 8,252,975 B2
(45) Date of Patent: Aug. 28, 2012

(54) GENETICALLY MODIFIED PLANTS WHICH SYNTHESIZE A LOW AMYLOSE STARCH WITH INCREASED SWELLING POWER

(75) Inventors: Claus Frohberg, Kleinmachnow (DE); Ralf-Christian Schmidt, Stahnsdorf (DE)

(73) Assignee: Bayer Cropscience AG, Monheim am Rhein (DE)

( * ) Notice: Subject to any disclaimer, the term of this patent is extended or adjusted under 35 U.S.C. 154(b) by 250 days.

(21) Appl. No.: 12/524,542

(22) PCT Filed: Jan. 23, 2008

(86) PCT No.: PCT/EP2008/000614
§ 371 (c)(1),
(2), (4) Date: Jul. 24, 2009

(87) PCT Pub. No.: WO2008/090008
PCT Pub. Date: Jul. 31, 2008

(65) Prior Publication Data
US 2009/0317535 A1   Dec. 24, 2009

(30) Foreign Application Priority Data
Jan. 26, 2007 (EP) .................................. 07090009

(51) Int. Cl.
*A01H 5/00* (2006.01)
*A01H 5/10* (2006.01)
*C12N 15/82* (2006.01)
(52) U.S. Cl. ......... 800/284; 800/298; 435/468; 435/419
(58) Field of Classification Search .................. None
See application file for complete search history.

(56) References Cited

U.S. PATENT DOCUMENTS

| | | | |
|---|---|---|---|
| 4,280,851 A | 7/1981 | Pitchon et al. | |
| 6,299,907 B1 | 10/2001 | Seib et al. | |
| 6,479,275 B1 | 11/2002 | Leathers et al. | |
| 7,001,771 B1 * | 2/2006 | Morell et al. | 435/468 |
| 2003/0167529 A1 * | 9/2003 | Landschutze | 800/284 |
| 2006/0127328 A1 | 6/2006 | Monsan et al. | |
| 2010/0034953 A1 | 2/2010 | Frohberg et al. | |

FOREIGN PATENT DOCUMENTS

| | | |
|---|---|---|
| EP | 0 522 942 | 1/1993 |
| WO | WO 92/11376 | 7/1992 |
| WO | WO 97/11188 | 3/1997 |
| WO | WO 97/45545 | 12/1997 |
| WO | WO 00/47727 | 8/2000 |
| WO | WO 2005/002359 | 1/2005 |
| WO | WO 2005/030941 | 4/2005 |
| WO | WO 2005/095617 | 10/2005 |
| WO | WO 2005/095619 | 10/2005 |

OTHER PUBLICATIONS

Fujita et al (Plant Science 160 (2001) 595-602).*
Tester et al (Cereal Chemistry 1996, 73(2):271-27).*
Tester et al (Cereal Chemistry vol. 67, No. 6,1990 p. 551-557).*
Singh et al (Journal Science and Food Agriculture 2004, 84:714-720).*
Landerito et al (Cereal Chemistry, vol. 82, No. 3, 2005 p. 271-276).*
Ball, S. et al., "From Bacterial Glycogen to Starch: Understanding the Biogenesis of the Plant Starch Granule", Annual Review Plant Biology, vol. 54, pp. 207-233, Jan. 2003.
Baunsgaard, L. et al., A Novel Isofrom of Glucan, Water Dikinase Phosphorylates Pre-Phosphorylated α-Glucans and is Involved in Starch Degradation in Arabidopsis, The Plant Journal, vol. 41, pp. 595-605, accepted Nov. 2004.
Blennow, A et al., "The Distribution of Covalently Bound Phosphate in the Starch Granule in Relation to Starch Crystallinity", International Journal of Biological Macromolecules, vol. 27, pp. 211-218, accepted Jan. 2000.
Chen, J. et al., "Effects of Compositional and Granular Properties on the Pasting of Viscosity of Rice Starch Blends", Starch/Starke, vol. 55, pp. 203-212, (2003).
GenBank Accession No. AF031162, Description: Oryza Saliva Granule-Bound Starch Synthase (Waxy) Gene, Complete cds., Modification Date: Nov. 2006.
GenBank Accession No. AF092443, Description: Oryza Sativa Granule Bound Starch Synthase (wx) Gene, Partial cds., Modification Date: Sep. 1999.
GenBank Accession No. AF092444, Description: Oryza Sativa Subsp. Japonica Granule Bound Starch Synthase (wx) Gene, Partial cds., Modification Date: Sep. 1999.
GenBank Accession No. AY027522, Description: Solanum Tuberosum Starch Associated Protein R1 mRNA, Complete cds., Modification Date: Feb. 2001.
Hovenkamp-Hermelink, J.H.M. et al., "Isolation of Amylose-Free Starch Mutant of the Potato (Solanum tuberosum L.)", Theoretical and Applied Genetics, vol. 75, pp. 217-221, accepted Jun. 1987.
Jane et al., "Phosphorus in Rice and Other Starches", Cereal Foods World, vol. 41, No. 11, pp. 827-832, Nov.-Dec. 1996.
Kotting, O. et al., "Identification of Novel Enzyme Required for Starch Metabolism in Arabidopsis Leaves. The Phosphoglucan, Water Dikinase", Plant Physiology, vol. 137, pp. 242-252, Jan. 2005.
Landerito, N. et al., "Preparation and Properties of Starch Phosphates Using Waxy, Common, and High-Amylose Corn Starches. II. Reacativ Extrusion Method", Cereal Chemistry, vol. 82, No. 3, pp. 271-276, accepted Feb. 2005.
Leach, H. et al, "Structure of the Starch Granule", Cereal Chemistry, vol. 36, pp. 534-544, Feb. 1959.

(Continued)

*Primary Examiner* — Anne Kubelik
*Assistant Examiner* — Lee A Visone
(74) *Attorney, Agent, or Firm* — Hunton & Williams LLP

(57) ABSTRACT

The present invention relates to genetically modified monocotyledonous plant cells and plants whose starch has an apparent amylose content of less than 5% by weight and an increased activity of a protein with the activity of a starch synthase II and an increased activity of a protein with the activity of a glucan, water dikinase. Such plants synthesize starch with an increased hot-water swelling power. Methods and processes for the generation/preparation of these plant cells, plants, starches and flours are likewise subject matter of the present invention.

17 Claims, 2 Drawing Sheets

OTHER PUBLICATIONS

Leathers, T. et al., "Characterization of a Novel Modified Alternan", Carbohydrate Polymers, vol. 54, pp. 107-113, accepted May 2003.

Li, Z. et al., "The Structural Organization of the Gene Encoding Class II Starch Synthase of Wheat and Barley and the Evolution of the Genes Encoding Starch Synthases in Plants", Functional & Integrative Geonomics, vol. 3, pp. 76-85, (2003).

Liu, H. et al., "Physical Properties of Cross-Linked and Acetylated Normal and Waxy Rice Starch", Starch/Starke, vol. 52, pp. 249-252, (1999).

Lorberth, R. et al., "Inhibition of a Starch-Granule-Bound Protein Leads to Modified Starch and Repression of Cold Sweetening", Nature Biotechnology, vol. 16, pp. 473-477, accepted Mar. 1998.

Mikkelsen, R. et al., "Functional Characterization of α-Glucan, Water Dikinase, the Starch Phosphorylating Enzyme", Biochemical Journal, vol. 377, pp. 525-532, (2004).

Moorthy, N., "Physicochemical and Functional Properties of Tropical Tuber Starches: A Review", Starch/Starke, vol. 54, pp. 559-592, second revision received Jul. 2002.

Nishi, A. et al., "Biochemical and Genetic Analysis of the Effects of Amylose Extender Mutation in Rice Endosperm", Plant Physiology, vol. 127, pp. 459-472, Oct. 2001.

Ritte, G. et al., "The Starch-Related R1 Protein is an α-Glucan, Water Dikinase", Proceedings of the National Academy of Science, vol. 99, No. 10, May 2002.

Ritte, G. et al., "Phosphorylation of C6- and C3-Positions of Glucosyl Residues in Starch Catalyzed by Distinct Dikinases", FEBS Letters, vol. 580, pp. 4872-4876, accepted Jul. 2006.

Sano, Y., "Differential Regulation of Waxy Gene Expression in Rice Endosperm", Theoretical and Applied Genetics, vol. 68, pp. 467-473, accepted Feb. 1984.

Shi, Y. et al., "Molecular Structure of a Low-Amylopectin Starch and Other High-Amylose Maize Starches", Journal of Cereal Science, vol. 27, pp. 289-299, (1998).

Shure, M. et l., "Molecular Identification and Isolation of the Waxy Locus in Maize", Cell, vol. 35, pp. 225-233, Nov. 1983.

Singh, N. et al. "Morphological, Thermal, Rheological and Noodle-Making Properties of Potato and Corn Starch", Journal of the Science of Food and Agriculture, vol. 82, pp. 1376-1383, accepted Apr. 2002.

Sitohy, M. et al., "Granular Properties of Different Starch Phosphate Monoesters", Stach/Starke, vol. 53, pp. 27-34, (2001).

Sodhi, N. et al., Morphological, Thermal and Rheological Properties of Starches Separated from Rice Cultivars Grown in India, Food Chemistry, vol. 80, pp. 99-108, (2003).

Takizawa, F., "Characterization of Tropical Starches Modified with Potassium Permanganate and Lactic Acid", Brazilian Archives of Biology and Technology, vol. 47, No. 6, Nov. 2004.

Tetlow, I. et al., "Recent Developments in Understanding the Regulation of Starch Metabolism in Higher Plants", Journal of Experimental Botany, vol. 55, No. 406, pp. 2131-2145, accepted Jul. 2004.

Van Hung, P. et al., "Effects of Granule Sizes on a Physicochemical Properties of a Cross-Linked and Acetylated Wheat Starches", Starch/Starke, vol. 57, pp. 413-420, accepted May 2005.

Villareal, C.P. et al., Waxy Gene Factor and Residual Protein of Rice Starch Granules, Starch/Starke, vol. 38, pp. 11- and 119, (1986).

Visser, R.G.F. et al., "Inhibition of the Expression of the Gene for Granule-Bound Starch Synthase in potato by Antisense Constructs", Molecular and General Genetics, vol. 225, pp. 289-296, (1991).

Yamamori, M. et al., "Genetic Elimination of a Starch Granule Protein, SGP-1, of Wheat Generated and Altered Starch with Apparent High Amylose", Theoretical and Applied Genetics, vol. 101, pp. 21-29, (2000).

Yasui, T. et al., "Strach Properties of a Waxy Mutant Line of Hull-Less Barley (Hordeum vulgare L.)", Starch/Starke, vol. 54, pp. 179-184, revision received Jan. 2002.

International Search Report for International Application No. PCT/EP2008/000614 mailed Jun. 3, 2008.

Written Opinion for International Application No. PCT/EP2008/000614 mailed Jun. 3, 2008.

Morell et al. (2005) Current Opinion in Plant Biology 8: 204-210.

* cited by examiner

Determination of SS2-Activity in transgenic lines

SEQUENCE LISTING

```
<160> NUMBER OF SEQ ID NOS: 12

<210> SEQ ID NO 1
<211> LENGTH: 4851
<212> TYPE: DNA
<213> ORGANISM: Solanum tuberosum
<220> FEATURE:
<221> NAME/KEY: transit_peptide
<222> LOCATION: (1)..(77)
<220> FEATURE:
<221> NAME/KEY: CDS
<222> LOCATION: (105)..(4499)
<300> PUBLICATION INFORMATION:
<308> DATABASE ACCESSION NUMBER: EMBL / Y09533
<309> DATABASE ENTRY DATE: 1998-07-30
<313> RELEVANT RESIDUES IN SEQ ID NO: (1)..(4499)

<400> SEQUENCE: 1
catcttcatc gaatttctcg aagcttcttc gctaatttcc tggtttcttc actcaaaatc      60
gacgtttcta gctgaacttg agtgaattaa gccagtggga ggat atg agt aat tcc     116
                                               Met Ser Asn Ser
                                                 1 tta ggg aat aac ttg ctg tac cag gga ttc cta acc tca aca gtg ttg     164
Leu Gly Asn Asn Leu Leu Tyr Gln Gly Phe Leu Thr Ser Thr Val Leu
  5                  10                  15                  20 gaa cat aaa agt aga atc agt cct cct tgt gtt gga ggc aat tct ttg     212
Glu His Lys Ser Arg Ile Ser Pro Pro Cys Val Gly Gly Asn Ser Leu
                 25                  30                  35 ttt caa caa caa gtg atc tcg aaa tca cct tta tca act gag ttt cga     260
Phe Gln Gln Gln Val Ile Ser Lys Ser Pro Leu Ser Thr Glu Phe Arg
             40                  45                  50 ggt aac agg tta aag gtg cag aaa aag aaa ata cct atg gaa aag aag     308
Gly Asn Arg Leu Lys Val Gln Lys Lys Lys Ile Pro Met Glu Lys Lys
         55                  60                  65 cgt gct ttt tct agt tct cct cat gct gta ctt acc act gat acc tct     356
Arg Ala Phe Ser Ser Ser Pro His Ala Val Leu Thr Thr Asp Thr Ser
     70                  75                  80 tct gag cta gca gaa aag ttc agt cta ggg ggg aat att gag cta cag     404
Ser Glu Leu Ala Glu Lys Phe Ser Leu Gly Gly Asn Ile Glu Leu Gln
 85                  90                  95                 100 gtt gat gtt agg cct ccc act tca ggt gat gtg tcc ttt gtg gat ttt     452
Val Asp Val Arg Pro Pro Thr Ser Gly Asp Val Ser Phe Val Asp Phe
                105                 110                 115 caa gta aca aat ggt agt gat aaa ctg ttt ttg cac tgg ggg gca gta     500
Gln Val Thr Asn Gly Ser Asp Lys Leu Phe Leu His Trp Gly Ala Val
            120                 125                 130 aaa ttc ggg aaa gaa aca tgg tct ctt ccg aat gat cgt cca gat ggg     548
Lys Phe Gly Lys Glu Thr Trp Ser Leu Pro Asn Asp Arg Pro Asp Gly
        135                 140                 145 acc aaa gtg tac aag aac aaa gca ctt aga act cca ttt gtt aaa tct     596
Thr Lys Val Tyr Lys Asn Lys Ala Leu Arg Thr Pro Phe Val Lys Ser
    150                 155                 160 ggc tct aac tcc atc ctg aga ctg gag ata cga gac act gct atc gaa     644
Gly Ser Asn Ser Ile Leu Arg Leu Glu Ile Arg Asp Thr Ala Ile Glu
165                 170                 175                 180 gct att gag ttt ctc ata tac gat gaa gcc cac gat aaa tgg ata aag     692
Ala Ile Glu Phe Leu Ile Tyr Asp Glu Ala His Asp Lys Trp Ile Lys
                185                 190                 195
```

```
aat aat ggt ggt aat ttt cgt gtc aaa ttg tca aga aaa gag ata cga    740
Asn Asn Gly Gly Asn Phe Arg Val Lys Leu Ser Arg Lys Glu Ile Arg
        200             205             210 ggc cca gat gtt tct gtt cct gag gag ctt gta cag atc caa tca tat    788
Gly Pro Asp Val Ser Val Pro Glu Glu Leu Val Gln Ile Gln Ser Tyr
        215             220             225 ttg agg tgg gag agg aag gga aaa cag aat tac ccc cct gag aaa gag    836
Leu Arg Trp Glu Arg Lys Gly Lys Gln Asn Tyr Pro Pro Glu Lys Glu
    230             235             240 aag gag gaa tat gag gct gct cga act gtg cta cag gag gaa ata gct    884
Lys Glu Glu Tyr Glu Ala Ala Arg Thr Val Leu Gln Glu Glu Ile Ala
245             250             255             260 cgt ggt gct tcc ata cag gac att cga gca agg cta aca aaa act aat    932
Arg Gly Ala Ser Ile Gln Asp Ile Arg Ala Arg Leu Thr Lys Thr Asn
                265             270             275 gat aaa agt caa agc aaa gaa gag cct ctt cat gta aca aag agt gat    980
Asp Lys Ser Gln Ser Lys Glu Glu Pro Leu His Val Thr Lys Ser Asp
            280             285             290 ata cct gat gac ctt gcc caa gca caa gct tac att agg tgg gag aaa   1028
Ile Pro Asp Asp Leu Ala Gln Ala Gln Ala Tyr Ile Arg Trp Glu Lys
        295             300             305 gca gga aag ccg aac tat cct cca gaa aag caa att gaa gaa ctc gaa   1076
Ala Gly Lys Pro Asn Tyr Pro Pro Glu Lys Gln Ile Glu Glu Leu Glu
310             315             320 gaa gca aga aga gaa ttg caa ctt gag ctt gag aaa ggc att acc ctt   1124
Glu Ala Arg Arg Glu Leu Gln Leu Glu Leu Glu Lys Gly Ile Thr Leu
325             330             335             340 gat gag ttg cgg aaa acg att aca aaa ggg gag ata aaa act aag gtg   1172
Asp Glu Leu Arg Lys Thr Ile Thr Lys Gly Glu Ile Lys Thr Lys Val
            345             350             355 gaa aag cac ctg aaa aga agt tct ttt gcc gtt gaa aga atc caa aga   1220
Glu Lys His Leu Lys Arg Ser Ser Phe Ala Val Glu Arg Ile Gln Arg
        360             365             370 aag aag aga gac ttt ggg cat ctt att aat aag tat act tcc agt cct   1268
Lys Lys Arg Asp Phe Gly His Leu Ile Asn Lys Tyr Thr Ser Ser Pro
    375             380             385 gca gta caa gta caa aag gtc ttg gaa gaa cca cca gcc tta tct aaa   1316
Ala Val Gln Val Gln Lys Val Leu Glu Glu Pro Pro Ala Leu Ser Lys
390             395             400 att aag ctg tat gcc aag gag aag gag gag cag att gat gat ccg atc   1364
Ile Lys Leu Tyr Ala Lys Glu Lys Glu Glu Gln Ile Asp Asp Pro Ile
405             410             415             420 cta aat aaa aag atc ttt aag gtc gat gat ggg gag cta ctg gta ctg   1412
Leu Asn Lys Lys Ile Phe Lys Val Asp Asp Gly Glu Leu Leu Val Leu
            425             430             435 gta gca aag tcc tct ggg aag aca aaa gta cat cta gct aca gat ctg   1460
Val Ala Lys Ser Ser Gly Lys Thr Lys Val His Leu Ala Thr Asp Leu
        440             445             450 aat cag cca att act ctt cac tgg gca tta tcc aaa agt cct gga gag   1508
Asn Gln Pro Ile Thr Leu His Trp Ala Leu Ser Lys Ser Pro Gly Glu
    455             460             465 tgg atg gta cca cct tca agc ata ttg cct cct ggg tca att att tta   1556
Trp Met Val Pro Pro Ser Ser Ile Leu Pro Pro Gly Ser Ile Ile Leu
470             475             480 gac aag gct gcc gaa aca cct ttt tca gcc agt tct tct gat ggt cta   1604
Asp Lys Ala Ala Glu Thr Pro Phe Ser Ala Ser Ser Ser Asp Gly Leu
485             490             495             500 act tct aag gta caa tct ttg gat ata gta att gaa gat ggc aat ttt   1652
Thr Ser Lys Val Gln Ser Leu Asp Ile Val Ile Glu Asp Gly Asn Phe
            505             510             515
```

| | |
|---|---|
| gtg ggg atg cca ttt gtt ctt ttg tct ggt gaa aaa tgg att aag aac<br>Val Gly Met Pro Phe Val Leu Leu Ser Gly Glu Lys Trp Ile Lys Asn<br>520 525 530 | 1700 |
| caa ggg tcg gat ttc tat gtt ggc ttc agt gct gca tcc aaa tta gca<br>Gln Gly Ser Asp Phe Tyr Val Gly Phe Ser Ala Ala Ser Lys Leu Ala<br>535 540 545 | 1748 |
| ctc aag gct gct ggg gat ggc agt gga act gca aag tct tta ctg gat<br>Leu Lys Ala Ala Gly Asp Gly Ser Gly Thr Ala Lys Ser Leu Leu Asp<br>550 555 560 | 1796 |
| aaa ata gca gat atg gaa agt gag gct cag aag tca ttt atg cac cgg<br>Lys Ile Ala Asp Met Glu Ser Glu Ala Gln Lys Ser Phe Met His Arg<br>565 570 575 580 | 1844 |
| ttt aat att gca gct gac ttg ata gaa gat gcc act agt gct ggt gaa<br>Phe Asn Ile Ala Ala Asp Leu Ile Glu Asp Ala Thr Ser Ala Gly Glu<br>585 590 595 | 1892 |
| ctt ggt ttt gct gga att ctt gta tgg atg agg ttc atg gct aca agg<br>Leu Gly Phe Ala Gly Ile Leu Val Trp Met Arg Phe Met Ala Thr Arg<br>600 605 610 | 1940 |
| caa ctg ata tgg aac aaa aac tat aac gta aaa cca cgt gaa ata agc<br>Gln Leu Ile Trp Asn Lys Asn Tyr Asn Val Lys Pro Arg Glu Ile Ser<br>615 620 625 | 1988 |
| aag gct cag gac aga ctt aca gac ttg ttg cag aat gct ttc acc agt<br>Lys Ala Gln Asp Arg Leu Thr Asp Leu Leu Gln Asn Ala Phe Thr Ser<br>630 635 640 | 2036 |
| cac cct cag tac cgt gaa att ttg cgg atg att atg tca act gtt gga<br>His Pro Gln Tyr Arg Glu Ile Leu Arg Met Ile Met Ser Thr Val Gly<br>645 650 655 660 | 2084 |
| cgt gga ggt gaa ggg gat gta gga cag cga att agg gat gaa att ttg<br>Arg Gly Gly Glu Gly Asp Val Gly Gln Arg Ile Arg Asp Glu Ile Leu<br>665 670 675 | 2132 |
| gtc atc cag agg aac aat gac tgc aag ggt ggt atg atg caa gaa tgg<br>Val Ile Gln Arg Asn Asn Asp Cys Lys Gly Gly Met Met Gln Glu Trp<br>680 685 690 | 2180 |
| cat cag aaa ttg cat aat aat act agt cct gat gat gtt gtg atc tgt<br>His Gln Lys Leu His Asn Asn Thr Ser Pro Asp Asp Val Val Ile Cys<br>695 700 705 | 2228 |
| cag gca tta att gac tac atc aag agt gat ttt gat ctt ggt gtt tat<br>Gln Ala Leu Ile Asp Tyr Ile Lys Ser Asp Phe Asp Leu Gly Val Tyr<br>710 715 720 | 2276 |
| tgg aaa acc ctg aat gag aac gga ata aca aaa gag cgt ctt ttg agt<br>Trp Lys Thr Leu Asn Glu Asn Gly Ile Thr Lys Glu Arg Leu Leu Ser<br>725 730 735 740 | 2324 |
| tat gac cgt gct atc cat tct gaa cca aat ttt aga gga gat caa aag<br>Tyr Asp Arg Ala Ile His Ser Glu Pro Asn Phe Arg Gly Asp Gln Lys<br>745 750 755 | 2372 |
| ggt ggt ctt ttg cgt gat tta ggt cac tat atg aga aca ttg aag gca<br>Gly Gly Leu Leu Arg Asp Leu Gly His Tyr Met Arg Thr Leu Lys Ala<br>760 765 770 | 2420 |
| gtt cat tca ggt gca gat ctt gag tct gct att gca aac tgc atg ggc<br>Val His Ser Gly Ala Asp Leu Glu Ser Ala Ile Ala Asn Cys Met Gly<br>775 780 785 | 2468 |
| tac aaa act gag gga gaa ggc ttt atg gtt gga gtc cag ata aat cct<br>Tyr Lys Thr Glu Gly Glu Gly Phe Met Val Gly Val Gln Ile Asn Pro<br>790 795 800 | 2516 |
| gta tca ggc ttg cca tct ggc ttt cag gac ctc ctc cat ttt gtc tta<br>Val Ser Gly Leu Pro Ser Gly Phe Gln Asp Leu Leu His Phe Val Leu<br>805 810 815 820 | 2564 |
| gac cat gtg gaa gat aaa aat gtg gaa act ctt ctt gag aga ttg cta<br>Asp His Val Glu Asp Lys Asn Val Glu Thr Leu Leu Glu Arg Leu Leu<br>825 830 835 | 2612 |

| | | |
|---|---|---|
| gag gct cgt gag gag ctt agg ccc ttg ctt ctc aaa cca aac aac cgt<br>Glu Ala Arg Glu Glu Leu Arg Pro Leu Leu Leu Lys Pro Asn Asn Arg<br>840                        845                     850 | | 2660 |
| cta aag gat ctg ctg ttt ttg gac ata gca ctt gat tct aca gtt aga<br>Leu Lys Asp Leu Leu Phe Leu Asp Ile Ala Leu Asp Ser Thr Val Arg<br>    855                        860                     865 | | 2708 |
| aca gca gta gaa agg gga tat gaa gaa ttg aac aac gct aat cct gag<br>Thr Ala Val Glu Arg Gly Tyr Glu Glu Leu Asn Asn Ala Asn Pro Glu<br>870                        875                     880 | | 2756 |
| aaa atc atg tac ttc atc tcc ctc gtt ctt gaa aat ctc gca ctc tct<br>Lys Ile Met Tyr Phe Ile Ser Leu Val Leu Glu Asn Leu Ala Leu Ser<br>885                        890                     895                     900 | | 2804 |
| gtg gac gat aat gaa gat ctt gtt tat tgc ttg aag gga tgg aat caa<br>Val Asp Asp Asn Glu Asp Leu Val Tyr Cys Leu Lys Gly Trp Asn Gln<br>                     905                     910                     915 | | 2852 |
| gct ctt tca atg tcc aat ggt ggg gac aac cat tgg gct tta ttt gca<br>Ala Leu Ser Met Ser Asn Gly Gly Asp Asn His Trp Ala Leu Phe Ala<br>920                        925                     930 | | 2900 |
| aaa gct gtg ctt gac aga acc cgt ctt gca ctt gca agc aag gca gag<br>Lys Ala Val Leu Asp Arg Thr Arg Leu Ala Leu Ala Ser Lys Ala Glu<br>    935                        940                     945 | | 2948 |
| tgg tac cat cac tta ttg cag cca tct gcc gaa tat cta gga tca ata<br>Trp Tyr His His Leu Leu Gln Pro Ser Ala Glu Tyr Leu Gly Ser Ile<br>    950                        955                     960 | | 2996 |
| ctt ggg gtg gac caa tgg gct ttg aac ata ttt act gaa gaa att ata<br>Leu Gly Val Asp Gln Trp Ala Leu Asn Ile Phe Thr Glu Glu Ile Ile<br>965                        970                     975                     980 | | 3044 |
| cgt gct gga tca gca gct tca tta tcc tct ctt ctt aat aga ctc gat<br>Arg Ala Gly Ser Ala Ala Ser Leu Ser Ser Leu Leu Asn Arg Leu Asp<br>                     985                     990                     995 | | 3092 |
| ccc gtg ctt cgg aaa act gca aat cta gga agt tgg cag att atc<br>Pro Val Leu Arg Lys Thr Ala Asn Leu Gly Ser Trp Gln Ile Ile<br>            1000                   1005                  1010 | | 3137 |
| agt cca gtt gaa gcc gtt gga tat gtt gtc gtt gtg gat gag ttg<br>Ser Pro Val Glu Ala Val Gly Tyr Val Val Val Val Asp Glu Leu<br>            1015                   1020                  1025 | | 3182 |
| ctt tca gtt cag aat gaa atc tac gag aag ccc acg atc tta gta<br>Leu Ser Val Gln Asn Glu Ile Tyr Glu Lys Pro Thr Ile Leu Val<br>            1030                   1035                  1040 | | 3227 |
| gca aaa tct gtt aaa gga gag gag gaa att cct gat ggt gct gtt<br>Ala Lys Ser Val Lys Gly Glu Glu Glu Ile Pro Asp Gly Ala Val<br>            1045                   1050                  1055 | | 3272 |
| gcc ctg ata aca cca gac atg cca gat gtt ctt tca cat gtt tct<br>Ala Leu Ile Thr Pro Asp Met Pro Asp Val Leu Ser His Val Ser<br>            1060                   1065                  1070 | | 3317 |
| gtt cga gct aga aat ggg aag gtt tgc ttt gct aca tgc ttt gat<br>Val Arg Ala Arg Asn Gly Lys Val Cys Phe Ala Thr Cys Phe Asp<br>            1075                   1080                  1085 | | 3362 |
| ccc aat ata ttg gct gac ctc caa gca aag gaa gga agg att ttg<br>Pro Asn Ile Leu Ala Asp Leu Gln Ala Lys Glu Gly Arg Ile Leu<br>            1090                   1095                  1100 | | 3407 |
| ctc tta aag cct aca cct tca gac ata atc tat agt gag gtg aat<br>Leu Leu Lys Pro Thr Pro Ser Asp Ile Ile Tyr Ser Glu Val Asn<br>            1105                   1110                  1115 | | 3452 |
| gag att gag ctc caa agt tca agt aac ttg gta gaa gct gaa act<br>Glu Ile Glu Leu Gln Ser Ser Ser Asn Leu Val Glu Ala Glu Thr<br>            1120                   1125                  1130 | | 3497 |
| tca gca aca ctt aga ttg gtg aaa aag caa ttt ggt ggt tgt tac<br>Ser Ala Thr Leu Arg Leu Val Lys Lys Gln Phe Gly Gly Cys Tyr<br>            1135                   1140                  1145 | | 3542 |

```
gca ata tca gca gat gaa ttc aca agt gaa atg gtt gga gct aaa        3587
Ala Ile Ser Ala Asp Glu Phe Thr Ser Glu Met Val Gly Ala Lys
        1150                1155                1160 tca cgt aat att gca tat ctg aaa gga aaa gtg cct tcc tcg gtg        3632
Ser Arg Asn Ile Ala Tyr Leu Lys Gly Lys Val Pro Ser Ser Val
    1165                1170                1175 gga att cct acg tca gta gct ctt cca ttt gga gtc ttt gag aaa        3677
Gly Ile Pro Thr Ser Val Ala Leu Pro Phe Gly Val Phe Glu Lys
            1180                1185                1190 gta ctt tca gac gac ata aat cag gga gtg gca aaa gag ttg caa        3722
Val Leu Ser Asp Asp Ile Asn Gln Gly Val Ala Lys Glu Leu Gln
                1195                1200                1205 att ctg atg aaa aaa cta tct gaa gga gac ttc agc gct ctt ggt        3767
Ile Leu Met Lys Lys Leu Ser Glu Gly Asp Phe Ser Ala Leu Gly
                    1210                1215                1220 gaa att cgc aca acg gtt tta gat ctt tca gca cca gct caa ttg        3812
Glu Ile Arg Thr Thr Val Leu Asp Leu Ser Ala Pro Ala Gln Leu
1225                1230                1235 gtc aaa gag ctg aag gag aag atg cag ggt tct ggc atg cct tgg        3857
Val Lys Glu Leu Lys Glu Lys Met Gln Gly Ser Gly Met Pro Trp
    1240                1245                1250 cct ggt gat gaa ggt cca aag cgg tgg gaa caa gca tgg atg gcc        3902
Pro Gly Asp Glu Gly Pro Lys Arg Trp Glu Gln Ala Trp Met Ala
        1255                1260                1265 ata aaa aag gtg tgg gct tca aaa tgg aat gag aga gca tac ttc        3947
Ile Lys Lys Val Trp Ala Ser Lys Trp Asn Glu Arg Ala Tyr Phe
            1270                1275                1280 agc aca agg aag gtg aaa ctg gat cat gac tat ctg tgc atg gct        3992
Ser Thr Arg Lys Val Lys Leu Asp His Asp Tyr Leu Cys Met Ala
                1285                1290                1295 gtc ctt gtt caa gaa ata ata aat gct gat tat gca ttt gtc att        4037
Val Leu Val Gln Glu Ile Ile Asn Ala Asp Tyr Ala Phe Val Ile
                    1300                1305                1310 cac aca acc aac cca tct tcc gga gac gac tca gaa ata tat gcc        4082
His Thr Thr Asn Pro Ser Ser Gly Asp Asp Ser Glu Ile Tyr Ala
1315                1320                1325 gag gtg gtc agg ggc ctt ggg gaa aca ctt gtt gga gct tat cca        4127
Glu Val Val Arg Gly Leu Gly Glu Thr Leu Val Gly Ala Tyr Pro
    1330                1335                1340 gga cgt gct ttg agt ttt atc tgc aag aaa aag gat ctc aac tct        4172
Gly Arg Ala Leu Ser Phe Ile Cys Lys Lys Lys Asp Leu Asn Ser
        1345                1350                1355 cct caa gtg tta ggt tac cca agc aaa ccg atc ggc ctt ttc ata        4217
Pro Gln Val Leu Gly Tyr Pro Ser Lys Pro Ile Gly Leu Phe Ile
            1360                1365                1370 aaa aga tct atc atc ttc cga tct gat tcc aat ggg gaa gat ttg        4262
Lys Arg Ser Ile Ile Phe Arg Ser Asp Ser Asn Gly Glu Asp Leu
                1375                1380                1385 gaa ggt tat gcc ggt gct ggc ctc tac gac agt gta cca atg gat        4307
Glu Gly Tyr Ala Gly Ala Gly Leu Tyr Asp Ser Val Pro Met Asp
                    1390                1395                1400 gag gag gaa aaa gtt gta att gat tac tct tcc gac cca ttg ata        4352
Glu Glu Glu Lys Val Val Ile Asp Tyr Ser Ser Asp Pro Leu Ile
1405                1410                1415 act gat ggt aac ttc cgc cag aca atc ctg tcc aac att gct cgt        4397
Thr Asp Gly Asn Phe Arg Gln Thr Ile Leu Ser Asn Ile Ala Arg
    1420                1425                1430 gct gga cat gct atc gag gag cta tat ggc tct cct caa gac att        4442
Ala Gly His Ala Ile Glu Glu Leu Tyr Gly Ser Pro Gln Asp Ile
        1435                1440                1445
```

-continued

```
gag ggt gta gtg  agg gat gga aag att  tat gtc gtt cag aca  aga     4487
Glu Gly Val Val  Arg Asp Gly Lys Ile  Tyr Val Val Gln Thr  Arg
            1450                1455                 1460 cca cag atg tga ttatattctc gttgtatgtt gttcagagaa gaccacagat        4539
Pro Gln Met gtgatcatat tctcattgta tcagatctgt gaccacttac ctgataccctc ccatgaagtt 4599 acctgtatga ttatacgtga tccaaagcca tcacatcatg ttcaccttca gctattggag  4659
gagaagtgag aagtaggaat tgcaatatga ggaataataa gaaaacttt gtaaaagcta   4719 aattagctgg gtatgatata gggagaaatg tgtaaacatt gtactatata tagtatatac  4779
acacgcatta tgtattgcat tatgcactga ataatatcgc agcatcaaag aagaaatcct  4839
ttgggtggtt tc                                                      4851
```

<210> SEQ ID NO 2
<211> LENGTH: 1464
<212> TYPE: PRT
<213> ORGANISM: Solanum tuberosum

<400> SEQUENCE: 2

```
Met Ser Asn Ser Leu Gly Asn Asn Leu Leu Tyr Gln Gly Phe Leu Thr
1               5                   10                  15

Ser Thr Val Leu Glu His Lys Ser Arg Ile Ser Pro Pro Cys Val Gly
            20                  25                  30

Gly Asn Ser Leu Phe Gln Gln Val Ile Ser Lys Ser Pro Leu Ser
        35                  40                  45

Thr Glu Phe Arg Gly Asn Arg Leu Lys Val Gln Lys Lys Ile Pro
    50                  55                  60

Met Glu Lys Lys Arg Ala Phe Ser Ser Pro His Ala Val Leu Thr
65                  70                  75                  80

Thr Asp Thr Ser Ser Glu Leu Ala Glu Lys Phe Ser Leu Gly Gly Asn
                85                  90                  95

Ile Glu Leu Gln Val Asp Val Arg Pro Pro Thr Ser Gly Asp Val Ser
            100                 105                 110

Phe Val Asp Phe Gln Val Thr Asn Gly Ser Asp Lys Leu Phe Leu His
        115                 120                 125

Trp Gly Ala Val Lys Phe Gly Lys Glu Thr Trp Ser Leu Pro Asn Asp
    130                 135                 140

Arg Pro Asp Gly Thr Lys Val Tyr Lys Asn Lys Ala Leu Arg Thr Pro
145                 150                 155                 160

Phe Val Lys Ser Gly Ser Asn Ser Ile Leu Arg Leu Glu Ile Arg Asp
                165                 170                 175

Thr Ala Ile Glu Ala Ile Glu Phe Leu Ile Tyr Asp Glu Ala His Asp
            180                 185                 190

Lys Trp Ile Lys Asn Asn Gly Gly Asn Phe Arg Val Lys Leu Ser Arg
        195                 200                 205

Lys Glu Ile Arg Gly Pro Asp Val Ser Val Pro Glu Glu Leu Val Gln
    210                 215                 220

Ile Gln Ser Tyr Leu Arg Trp Glu Arg Lys Gly Lys Gln Asn Tyr Pro
225                 230                 235                 240

Pro Glu Lys Glu Lys Glu Glu Tyr Glu Ala Ala Arg Thr Val Leu Gln
                245                 250                 255

Glu Glu Ile Ala Arg Gly Ala Ser Ile Gln Asp Ile Arg Ala Arg Leu
            260                 265                 270

Thr Lys Thr Asn Asp Lys Ser Gln Ser Lys Glu Glu Pro Leu His Val
```

-continued

```
                275                 280                 285
Thr Lys Ser Asp Ile Pro Asp Leu Ala Gln Ala Gln Ala Tyr Ile
290                 295                 300
Arg Trp Glu Lys Ala Gly Lys Pro Asn Tyr Pro Glu Lys Gln Ile
305                 310                 315                 320
Glu Glu Leu Glu Glu Ala Arg Arg Glu Leu Gln Leu Glu Leu Lys
                325                 330                 335
Gly Ile Thr Leu Asp Glu Leu Arg Lys Thr Ile Thr Lys Gly Glu Ile
                340                 345                 350
Lys Thr Lys Val Glu Lys His Leu Lys Arg Ser Ser Phe Ala Val Glu
            355                 360                 365
Arg Ile Gln Arg Lys Lys Arg Asp Phe Gly His Leu Ile Asn Lys Tyr
370                 375                 380
Thr Ser Ser Pro Ala Val Gln Val Gln Lys Val Leu Glu Glu Pro Pro
385                 390                 395                 400
Ala Leu Ser Lys Ile Lys Leu Tyr Ala Lys Glu Lys Glu Glu Gln Ile
                405                 410                 415
Asp Asp Pro Ile Leu Asn Lys Lys Ile Phe Lys Val Asp Asp Gly Glu
            420                 425                 430
Leu Leu Val Leu Val Ala Lys Ser Ser Gly Lys Thr Lys Val His Leu
            435                 440                 445
Ala Thr Asp Leu Asn Gln Pro Ile Thr Leu His Trp Ala Leu Ser Lys
450                 455                 460
Ser Pro Gly Glu Trp Met Val Pro Pro Ser Ile Leu Pro Pro Gly
465                 470                 475                 480
Ser Ile Ile Leu Asp Lys Ala Ala Glu Thr Pro Phe Ser Ala Ser Ser
                485                 490                 495
Ser Asp Gly Leu Thr Ser Lys Val Gln Ser Leu Asp Ile Val Ile Glu
            500                 505                 510
Asp Gly Asn Phe Val Gly Met Pro Phe Val Leu Ser Gly Glu Lys
            515                 520                 525
Trp Ile Lys Asn Gln Gly Ser Asp Phe Tyr Val Gly Phe Ser Ala Ala
530                 535                 540
Ser Lys Leu Ala Leu Lys Ala Ala Gly Asp Gly Ser Gly Thr Ala Lys
545                 550                 555                 560
Ser Leu Leu Asp Lys Ile Ala Asp Met Glu Ser Glu Ala Gln Lys Ser
                565                 570                 575
Phe Met His Arg Phe Asn Ile Ala Ala Asp Leu Ile Glu Asp Ala Thr
            580                 585                 590
Ser Ala Gly Glu Leu Gly Phe Ala Gly Ile Leu Val Trp Met Arg Phe
            595                 600                 605
Met Ala Thr Arg Gln Leu Ile Trp Asn Lys Asn Tyr Asn Val Lys Pro
610                 615                 620
Arg Glu Ile Ser Lys Ala Gln Asp Arg Leu Thr Asp Leu Leu Gln Asn
625                 630                 635                 640
Ala Phe Thr Ser His Pro Gln Tyr Arg Glu Ile Leu Arg Met Ile Met
                645                 650                 655
Ser Thr Val Gly Arg Gly Gly Glu Gly Asp Val Gly Gln Arg Ile Arg
            660                 665                 670
Asp Glu Ile Leu Val Ile Gln Arg Asn Asn Asp Cys Lys Gly Gly Met
            675                 680                 685
Met Gln Glu Trp His Gln Lys Leu His Asn Asn Thr Ser Pro Asp Asp
        690                 695                 700
```

-continued

Val Val Ile Cys Gln Ala Leu Ile Asp Tyr Ile Lys Ser Asp Phe Asp
705                 710                 715                 720

Leu Gly Val Tyr Trp Lys Thr Leu Asn Glu Asn Gly Ile Thr Lys Glu
            725                 730                 735

Arg Leu Leu Ser Tyr Asp Arg Ala Ile His Ser Glu Pro Asn Phe Arg
        740                 745                 750

Gly Asp Gln Lys Gly Gly Leu Arg Asp Leu Gly His Tyr Met Arg
            755                 760                 765

Thr Leu Lys Ala Val His Ser Gly Ala Asp Leu Glu Ser Ala Ile Ala
770                 775                 780

Asn Cys Met Gly Tyr Lys Thr Glu Gly Glu Gly Phe Met Val Gly Val
785                 790                 795                 800

Gln Ile Asn Pro Val Ser Gly Leu Pro Ser Gly Phe Gln Asp Leu Leu
            805                 810                 815

His Phe Val Leu Asp His Val Glu Asp Lys Asn Val Glu Thr Leu Leu
            820                 825                 830

Glu Arg Leu Leu Glu Ala Arg Glu Glu Leu Arg Pro Leu Leu Leu Lys
        835                 840                 845

Pro Asn Asn Arg Leu Lys Asp Leu Leu Phe Leu Asp Ile Ala Leu Asp
850                 855                 860

Ser Thr Val Arg Thr Ala Val Glu Arg Gly Tyr Glu Glu Leu Asn Asn
865                 870                 875                 880

Ala Asn Pro Glu Lys Ile Met Tyr Phe Ile Ser Leu Val Leu Glu Asn
            885                 890                 895

Leu Ala Leu Ser Val Asp Asp Asn Glu Asp Leu Val Tyr Cys Leu Lys
            900                 905                 910

Gly Trp Asn Gln Ala Leu Ser Met Ser Asn Gly Gly Asp Asn His Trp
            915                 920                 925

Ala Leu Phe Ala Lys Ala Val Leu Asp Arg Thr Arg Leu Ala Leu Ala
930                 935                 940

Ser Lys Ala Glu Trp Tyr His His Leu Leu Gln Pro Ser Ala Glu Tyr
945                 950                 955                 960

Leu Gly Ser Ile Leu Gly Val Asp Gln Trp Ala Leu Asn Ile Phe Thr
            965                 970                 975

Glu Glu Ile Ile Arg Ala Gly Ser Ala Ala Ser Leu Ser Ser Leu Leu
            980                 985                 990

Asn Arg Leu Asp Pro Val Leu Arg Lys Thr Ala Asn Leu Gly Ser Trp
        995                 1000                1005

Gln Ile Ile Ser Pro Val Glu Ala Val Gly Tyr Val Val Val Val
1010                1015                1020

Asp Glu Leu Leu Ser Val Gln Asn Glu Ile Tyr Glu Lys Pro Thr
1025                1030                1035

Ile Leu Val Ala Lys Ser Val Lys Gly Glu Glu Glu Ile Pro Asp
1040                1045                1050

Gly Ala Val Ala Leu Ile Thr Pro Asp Met Pro Asp Val Leu Ser
    1055                1060                1065

His Val Ser Val Arg Ala Arg Asn Gly Lys Val Cys Phe Ala Thr
    1070                1075                1080

Cys Phe Asp Pro Asn Ile Leu Ala Asp Leu Gln Ala Lys Glu Gly
1085                1090                1095

Arg Ile Leu Leu Leu Lys Pro Thr Pro Ser Asp Ile Ile Tyr Ser
    1100                1105                1110

Glu Val Asn Glu Ile Glu Leu Gln Ser Ser Ser Asn Leu Val Glu
    1115                1120                1125

Ala Glu Thr Ser Ala Thr Leu Arg Leu Val Lys Lys Gln Phe Gly
1130                1135                1140

Gly Cys Tyr Ala Ile Ser Ala Asp Glu Phe Thr Ser Glu Met Val
1145                1150                1155

Gly Ala Lys Ser Arg Asn Ile Ala Tyr Leu Lys Gly Lys Val Pro
1160                1165                1170

Ser Ser Val Gly Ile Pro Thr Ser Val Ala Leu Pro Phe Gly Val
1175                1180                1185

Phe Glu Lys Val Leu Ser Asp Asp Ile Asn Gln Gly Val Ala Lys
1190                1195                1200

Glu Leu Gln Ile Leu Met Lys Lys Leu Ser Glu Gly Asp Phe Ser
1205                1210                1215

Ala Leu Gly Glu Ile Arg Thr Thr Val Leu Asp Leu Ser Ala Pro
1220                1225                1230

Ala Gln Leu Val Lys Glu Leu Lys Glu Lys Met Gln Gly Ser Gly
1235                1240                1245

Met Pro Trp Pro Gly Asp Glu Gly Pro Lys Arg Trp Glu Gln Ala
1250                1255                1260

Trp Met Ala Ile Lys Lys Val Trp Ala Ser Lys Trp Asn Glu Arg
1265                1270                1275

Ala Tyr Phe Ser Thr Arg Lys Val Lys Leu Asp His Asp Tyr Leu
1280                1285                1290

Cys Met Ala Val Leu Val Gln Glu Ile Ile Asn Ala Asp Tyr Ala
1295                1300                1305

Phe Val Ile His Thr Thr Asn Pro Ser Ser Gly Asp Asp Ser Glu
1310                1315                1320

Ile Tyr Ala Glu Val Val Arg Gly Leu Gly Glu Thr Leu Val Gly
1325                1330                1335

Ala Tyr Pro Gly Arg Ala Leu Ser Phe Ile Cys Lys Lys Lys Asp
1340                1345                1350

Leu Asn Ser Pro Gln Val Leu Gly Tyr Pro Ser Lys Pro Ile Gly
1355                1360                1365

Leu Phe Ile Lys Arg Ser Ile Ile Phe Arg Ser Asp Ser Asn Gly
1370                1375                1380

Glu Asp Leu Glu Gly Tyr Ala Gly Ala Gly Leu Tyr Asp Ser Val
1385                1390                1395

Pro Met Asp Glu Glu Lys Val Val Ile Asp Tyr Ser Ser Asp
1400                1405                1410

Pro Leu Ile Thr Asp Gly Asn Phe Arg Gln Thr Ile Leu Ser Asn
1415                1420                1425

Ile Ala Arg Ala Gly His Ala Ile Glu Glu Leu Tyr Gly Ser Pro
1430                1435                1440

Gln Asp Ile Glu Gly Val Val Arg Asp Gly Lys Ile Tyr Val Val
1445                1450                1455

Gln Thr Arg Pro Gln Met
1460

<210> SEQ ID NO 3
<211> LENGTH: 3000
<212> TYPE: DNA
<213> ORGANISM: Triticum aestivum
<220> FEATURE:
<221> NAME/KEY: CDS
<222> LOCATION: (227)..(2623)

<400> SEQUENCE: 3

```
ctccaccgcg gtggcggccg ctctagaact agtggatccc ccgggctgca ggaattcggc      60
acgagcttcg gcctgacccc gttcgtttac ccccacacag agcacactcc agtccagtcc     120
agcccactgc caccgcgcta ctctccactc ccactgccac cacctccgcc tgcgccgcgc     180
tctgggcgga ccaacccgcg aaccgtacca tctcccgccc cgatcc atg tcg tcg        235
                                                  Met Ser Ser
                                                    1 gcg gtc gcg tcc gcc gca tcc ttc ctc gcg ctc gcg tca gcc tcc ccc       283
Ala Val Ala Ser Ala Ala Ser Phe Leu Ala Leu Ala Ser Ala Ser Pro
  5              10                  15 ggg aga tca cgc agg cgg gcg agg gtg agc gcg cag cca ccc cac gcc       331
Gly Arg Ser Arg Arg Ala Arg Val Ser Ala Gln Pro Pro His Ala
 20              25                  30                  35 ggg gcc ggc agg ttg cac tgg ccg ccg tgg ccg ccg cag cgc acg gct       379
Gly Ala Gly Arg Leu His Trp Pro Pro Trp Pro Pro Gln Arg Thr Ala
             40                  45                  50 cgc gac gga gct gtg gcg gcg ctc gcc gcc ggg aag aag gac gcg ggg       427
Arg Asp Gly Ala Val Ala Ala Leu Ala Ala Gly Lys Lys Asp Ala Gly
                 55                  60                  65 atc gac gac gcc gcc gcg tcc gtg agg cag ccc cgc gca ctc cgc ggt       475
Ile Asp Asp Ala Ala Ala Ser Val Arg Gln Pro Arg Ala Leu Arg Gly
             70                  75                  80 ggc gcc gcc acc aag gtc gcg gag cga agg gat ccc gtc aag acg ctc       523
Gly Ala Ala Thr Lys Val Ala Glu Arg Arg Asp Pro Val Lys Thr Leu
 85                  90                  95 gac cgc gac gcc gcg gaa ggc ggc ggg ccg tcc ccg ccg gca gcg agg       571
Asp Arg Asp Ala Ala Glu Gly Gly Gly Pro Ser Pro Pro Ala Ala Arg
100                 105                 110                 115 cag gac gcc gcc cgt ccg ccg agt atg aac ggc atg ccg gtg aac ggc       619
Gln Asp Ala Ala Arg Pro Pro Ser Met Asn Gly Met Pro Val Asn Gly
                120                 125                 130 gag aac aaa tct acc ggc ggc ggc ggc gcg act aaa gac agc ggg ctg       667
Glu Asn Lys Ser Thr Gly Gly Gly Gly Ala Thr Lys Asp Ser Gly Leu
            135                 140                 145 ccc acg ccc gca cgc gcg ccc cat ccg tcg acc cag aac aga gca ccg       715
Pro Thr Pro Ala Arg Ala Pro His Pro Ser Thr Gln Asn Arg Ala Pro
        150                 155                 160 gtg aac ggt gaa aac aaa gct aac gtc gcc tcg ccg ccg acg agc ata       763
Val Asn Gly Glu Asn Lys Ala Asn Val Ala Ser Pro Pro Thr Ser Ile
165                 170                 175 gcc gag gcc gcg gct tcg gat tcc gca gct acc att tcc atc agc gac       811
Ala Glu Ala Ala Ala Ser Asp Ser Ala Ala Thr Ile Ser Ile Ser Asp
180                 185                 190                 195 aag gcg ccg gag tcc gtt gtc cca gct gag aag acg ccg ccg tcg tcc       859
Lys Ala Pro Glu Ser Val Val Pro Ala Glu Lys Thr Pro Pro Ser Ser
                200                 205                 210 ggc tca aat ttc gag tcc tcg gcc tct gct ccc ggg tct gac act gtc       907
Gly Ser Asn Phe Glu Ser Ser Ala Ser Ala Pro Gly Ser Asp Thr Val
            215                 220                 225 agc gac gtg gaa caa gaa ctg aag aag ggt gcg gtc gtt gtc gaa gaa       955
Ser Asp Val Glu Gln Glu Leu Lys Lys Gly Ala Val Val Val Glu Glu
        230                 235                 240 gct cca aag cca aag gct ctt tcg ccg cct gca gcc ccc gct gta caa      1003
Ala Pro Lys Pro Lys Ala Leu Ser Pro Pro Ala Ala Pro Ala Val Gln
245                 250                 255 gaa gac ctt tgg gat ttc aag aaa tac att ggt ttc gag gag ccc gtg      1051
Glu Asp Leu Trp Asp Phe Lys Lys Tyr Ile Gly Phe Glu Glu Pro Val
                260                 265                 270                 275 gag gcc aag gat gat ggc cgg gct gtc gca gat gat gcg ggc tcc ttt      1099
```

-continued

```
                    Glu Ala Lys Asp Asp Gly Arg Ala Val Ala Asp Asp Ala Gly Ser Phe
                                    280                 285                 290 gaa cac cac cag aat cac gac tcc gga cct ttg gca ggg gag aat gtc           1147
Glu His His Gln Asn His Asp Ser Gly Pro Leu Ala Gly Glu Asn Val
                295                 300                 305 atg aac gtg gtc gtg gct gct gag tgt tct ccc tgg tgc aaa aca               1195
Met Asn Val Val Val Ala Ala Glu Cys Ser Pro Trp Cys Lys Thr
            310                 315                 320 ggt ggt ctg gga gat gtt gcg ggt gct ctg ccc aag gct ttg gca aag           1243
Gly Gly Leu Gly Asp Val Ala Gly Ala Leu Pro Lys Ala Leu Ala Lys
        325                 330                 335 aga gga cat cgt gtt atg gtt gtg gta cca agg tat ggg gac tat gaa           1291
Arg Gly His Arg Val Met Val Val Val Pro Arg Tyr Gly Asp Tyr Glu
340                 345                 350                 355 gaa gcc tac gat gtc gga gtc cga aaa tac tac aag gct gct gga cag           1339
Glu Ala Tyr Asp Val Gly Val Arg Lys Tyr Tyr Lys Ala Ala Gly Gln
                360                 365                 370 gat atg gaa gtg aat tat ttc cat gct tat atc gat gga gtt gat ttt           1387
Asp Met Glu Val Asn Tyr Phe His Ala Tyr Ile Asp Gly Val Asp Phe
                375                 380                 385 gtg ttc att gac gct cct ctc ttc cga cac cgt cag gaa gac att tat           1435
Val Phe Ile Asp Ala Pro Leu Phe Arg His Arg Gln Glu Asp Ile Tyr
        390                 395                 400 ggg ggc agc aga cag gaa att atg aag cgc atg att ttg ttc tgc aag           1483
Gly Gly Ser Arg Gln Glu Ile Met Lys Arg Met Ile Leu Phe Cys Lys
    405                 410                 415 gcc gct gtt gag gtt cca tgg cac gtt cca tgc ggc ggt gtc cct tat           1531
Ala Ala Val Glu Val Pro Trp His Val Pro Cys Gly Gly Val Pro Tyr
420                 425                 430                 435 ggg gat gga aat ctg gtg ttt att gca aat gat tgg cac acg gca ctc           1579
Gly Asp Gly Asn Leu Val Phe Ile Ala Asn Asp Trp His Thr Ala Leu
                440                 445                 450 ctg cct gtc tat ctg aaa gca tat tac agg gac cat ggt ttg atg cag           1627
Leu Pro Val Tyr Leu Lys Ala Tyr Tyr Arg Asp His Gly Leu Met Gln
                455                 460                 465 tac act cgg tcc att atg gtg ata cat aac atc gct cac cag ggc cgt           1675
Tyr Thr Arg Ser Ile Met Val Ile His Asn Ile Ala His Gln Gly Arg
        470                 475                 480 ggc cct gta gat gaa ttc ccg ttc acc gag ttg cct gag cac tac ctg           1723
Gly Pro Val Asp Glu Phe Pro Phe Thr Glu Leu Pro Glu His Tyr Leu
    485                 490                 495 gaa cac ttc aga ctg tac gac ccc gtg ggt ggt gaa cac gcc aac tac           1771
Glu His Phe Arg Leu Tyr Asp Pro Val Gly Gly Glu His Ala Asn Tyr
500                 505                 510                 515 ttc gcc gcc ggc ctg aag atg gcg gac cag gtt gtc gtg gtg agc ccc           1819
Phe Ala Ala Gly Leu Lys Met Ala Asp Gln Val Val Val Val Ser Pro
                520                 525                 530 ggg tac ctg tgg gag ctg aag acg gtg gag ggc ggc tgg ggg ctt cac           1867
Gly Tyr Leu Trp Glu Leu Lys Thr Val Glu Gly Gly Trp Gly Leu His
                535                 540                 545 gac atc ata cgg cag aac gac tgg aag acc cgc ggc atc gtc aac ggc           1915
Asp Ile Ile Arg Gln Asn Asp Trp Lys Thr Arg Gly Ile Val Asn Gly
        550                 555                 560 atc gac aac atg gag tgg aac ccc gag gtg gac gcc cac ctc aag tcg           1963
Ile Asp Asn Met Glu Trp Asn Pro Glu Val Asp Ala His Leu Lys Ser
    565                 570                 575 gac ggc tac acc aac ttc tcc ctg agg acg ctg gac tcc ggc aag cgg           2011
Asp Gly Tyr Thr Asn Phe Ser Leu Arg Thr Leu Asp Ser Gly Lys Arg
580                 585                 590                 595 cag tgc aag gag gcc ctg cag cgc gag ctg ggc ctg cag gtc cgc gcc           2059
```

```
                Gln Cys Lys Glu Ala Leu Gln Arg Glu Leu Gly Leu Gln Val Arg Ala
                                600                 605                 610 gac gtg ccg ctg ctc ggc ttc atc ggc cgc ctg gac ggg cag aag ggc         2107
Asp Val Pro Leu Leu Gly Phe Ile Gly Arg Leu Asp Gly Gln Lys Gly
            615                 620                 625 gtg gag atc atc gcg gac gcc atg ccc tgg atc gtg agc cag gac gtg         2155
Val Glu Ile Ile Ala Asp Ala Met Pro Trp Ile Val Ser Gln Asp Val
        630                 635                 640 cag ctg gtg atg ctg ggc acc ggg cgc cac gac ctg gag agc atg ctg         2203
Gln Leu Val Met Leu Gly Thr Gly Arg His Asp Leu Glu Ser Met Leu
    645                 650                 655 cag cac ttc gag cgg gag cac cac gac aag gtg cgc ggg tgg gtg ggg         2251
Gln His Phe Glu Arg Glu His His Asp Lys Val Arg Gly Trp Val Gly
660                 665                 670                 675 ttc tcc gtg cgc ctg gcg cac cgg atc acg gcg ggg gcg gac gcg ctc         2299
Phe Ser Val Arg Leu Ala His Arg Ile Thr Ala Gly Ala Asp Ala Leu
                680                 685                 690 ctc atg ccc tcc cgg ttc gag ccg tgc ggg ctg aac cag ctc tac gcc         2347
Leu Met Pro Ser Arg Phe Glu Pro Cys Gly Leu Asn Gln Leu Tyr Ala
            695                 700                 705 atg gcc tac ggc acc gtc ccc gtc gtg cac gcc gtc ggc ggc ctc agg         2395
Met Ala Tyr Gly Thr Val Pro Val Val His Ala Val Gly Gly Leu Arg
        710                 715                 720 gac acc gtg ccg ccg ttc gac ccc ttc aac cac tcc ggg ctc ggg tgg         2443
Asp Thr Val Pro Pro Phe Asp Pro Phe Asn His Ser Gly Leu Gly Trp
    725                 730                 735 acg ttc gac cgc gcc gag gcg cac aag ctg atc gag gcg ctc ggg cac         2491
Thr Phe Asp Arg Ala Glu Ala His Lys Leu Ile Glu Ala Leu Gly His
740                 745                 750                 755 tgc ctc cgc acc tac cga gac ttc aag gag agc tgg agg gcc ctc cag         2539
Cys Leu Arg Thr Tyr Arg Asp Phe Lys Glu Ser Trp Arg Ala Leu Gln
                760                 765                 770 gag cgc ggc atg tcg cag gac ttc agc tgg gag cac gcc gcc aag ctc         2587
Glu Arg Gly Met Ser Gln Asp Phe Ser Trp Glu His Ala Ala Lys Leu
            775                 780                 785 tac gag gac gtc ctc gtc aag gcc aag tac cag tgg tgaacgctag             2633
Tyr Glu Asp Val Leu Val Lys Ala Lys Tyr Gln Trp
        790                 795 ctgctagccg ctccagcccc gcatgcgtgc atgacaggat ggaactgcat tgcgcacgca      2693
ggaaagtgcc atggagcgcc ggcatccgcg aagtacagtg acatgaggtg tgtgtggttg      2753
agacgctgat tccaatccgg cccgtagcag agtagagcgg aggtatatgg gaatcttaac     2813
ttggtattgt aatttgttat gttgtgtgca ttattacaat gttgttactt attcttgtta    2873
agtcggaggc caagggcgaa agctagctca catgtctgat ggatgcacgt gccatggttg     2933
gtttggtagc gcagtgcaaa cggcaagaat gggaagtgaa ttcctccctg cttgaaaaaa    2993
aaaaaaa                                                              3000

<210> SEQ ID NO 4
<211> LENGTH: 799
<212> TYPE: PRT
<213> ORGANISM: Triticum aestivum

<400> SEQUENCE: 4

Met Ser Ser Ala Val Ala Ser Ala Ala Ser Phe Leu Ala Leu Ala Ser
1               5                   10                  15

Ala Ser Pro Gly Arg Ser Arg Arg Ala Arg Val Ser Ala Gln Pro
            20                  25                  30

Pro His Ala Gly Ala Gly Arg Leu His Trp Pro Pro Trp Pro Pro Gln
```

-continued

```
                35                  40                  45
Arg Thr Ala Arg Asp Gly Ala Val Ala Ala Leu Ala Ala Gly Lys Lys
 50                  55                  60
Asp Ala Gly Ile Asp Asp Ala Ala Ser Val Arg Gln Pro Arg Ala
 65                  70                  75                  80
Leu Arg Gly Gly Ala Ala Thr Lys Val Ala Glu Arg Arg Asp Pro Val
                 85                  90                  95
Lys Thr Leu Asp Arg Asp Ala Ala Glu Gly Gly Pro Ser Pro Pro
                100                 105                 110
Ala Ala Arg Gln Asp Ala Ala Arg Pro Pro Ser Met Asn Gly Met Pro
                115                 120                 125
Val Asn Gly Glu Asn Lys Ser Thr Gly Gly Gly Ala Thr Lys Asp
                130                 135                 140
Ser Gly Leu Pro Thr Pro Ala Arg Ala Pro His Pro Ser Thr Gln Asn
145                 150                 155                 160
Arg Ala Pro Val Asn Gly Glu Asn Lys Ala Asn Val Ala Ser Pro Pro
                165                 170                 175
Thr Ser Ile Ala Glu Ala Ala Ser Asp Ser Ala Ala Thr Ile Ser
                180                 185                 190
Ile Ser Asp Lys Ala Pro Glu Ser Val Val Pro Ala Glu Lys Thr Pro
                195                 200                 205
Pro Ser Ser Gly Ser Asn Phe Glu Ser Ser Ala Ser Ala Pro Gly Ser
                210                 215                 220
Asp Thr Val Ser Asp Val Glu Gln Glu Leu Lys Lys Gly Ala Val Val
225                 230                 235                 240
Val Glu Glu Ala Pro Lys Pro Lys Ala Leu Ser Pro Pro Ala Ala Pro
                245                 250                 255
Ala Val Gln Glu Asp Leu Trp Asp Phe Lys Lys Tyr Ile Gly Phe Glu
                260                 265                 270
Glu Pro Val Glu Ala Lys Asp Asp Gly Arg Ala Val Ala Asp Ala
                275                 280                 285
Gly Ser Phe Glu His His Gln Asn His Asp Ser Gly Pro Leu Ala Gly
                290                 295                 300
Glu Asn Val Met Asn Val Val Val Ala Glu Cys Ser Pro Trp
305                 310                 315                 320
Cys Lys Thr Gly Gly Leu Gly Asp Val Ala Gly Ala Leu Pro Lys Ala
                325                 330                 335
Leu Ala Lys Arg Gly His Arg Val Met Val Val Pro Arg Tyr Gly
                340                 345                 350
Asp Tyr Glu Glu Ala Tyr Asp Val Gly Val Arg Lys Tyr Tyr Lys Ala
                355                 360                 365
Ala Gly Gln Asp Met Glu Val Asn Tyr Phe His Ala Tyr Ile Asp Gly
                370                 375                 380
Val Asp Phe Val Phe Ile Asp Ala Pro Leu Phe Arg His Arg Gln Glu
385                 390                 395                 400
Asp Ile Tyr Gly Gly Ser Arg Gln Glu Ile Met Lys Arg Met Ile Leu
                405                 410                 415
Phe Cys Lys Ala Ala Val Glu Val Pro Trp His Val Pro Cys Gly Gly
                420                 425                 430
Val Pro Tyr Gly Asp Gly Asn Leu Val Phe Ile Ala Asn Asp Trp His
                435                 440                 445
Thr Ala Leu Leu Pro Val Tyr Leu Lys Ala Tyr Tyr Arg Asp His Gly
                450                 455                 460
```

```
Leu Met Gln Tyr Thr Arg Ser Ile Met Val Ile His Asn Ile Ala His
465                 470                 475                 480

Gln Gly Arg Gly Pro Val Asp Glu Phe Pro Phe Thr Glu Leu Pro Glu
                485                 490                 495

His Tyr Leu Glu His Phe Arg Leu Tyr Asp Pro Val Gly Gly Glu His
            500                 505                 510

Ala Asn Tyr Phe Ala Ala Gly Leu Lys Met Ala Asp Gln Val Val Val
        515                 520                 525

Val Ser Pro Gly Tyr Leu Trp Glu Leu Lys Thr Val Glu Gly Gly Trp
530                 535                 540

Gly Leu His Asp Ile Ile Arg Gln Asn Asp Trp Lys Thr Arg Gly Ile
545                 550                 555                 560

Val Asn Gly Ile Asp Asn Met Glu Trp Asn Pro Glu Val Asp Ala His
                565                 570                 575

Leu Lys Ser Asp Gly Tyr Thr Asn Phe Ser Leu Arg Thr Leu Asp Ser
            580                 585                 590

Gly Lys Arg Gln Cys Lys Glu Ala Leu Gln Arg Glu Leu Gly Leu Gln
        595                 600                 605

Val Arg Ala Asp Val Pro Leu Leu Gly Phe Ile Gly Arg Leu Asp Gly
610                 615                 620

Gln Lys Gly Val Glu Ile Ile Ala Asp Ala Met Pro Trp Ile Val Ser
625                 630                 635                 640

Gln Asp Val Gln Leu Val Met Leu Gly Thr Gly Arg His Asp Leu Glu
                645                 650                 655

Ser Met Leu Gln His Phe Glu Arg Glu His His Asp Lys Val Arg Gly
            660                 665                 670

Trp Val Gly Phe Ser Val Arg Leu Ala His Arg Ile Thr Ala Gly Ala
        675                 680                 685

Asp Ala Leu Leu Met Pro Ser Arg Phe Glu Pro Cys Gly Leu Asn Gln
690                 695                 700

Leu Tyr Ala Met Ala Tyr Gly Thr Val Pro Val Val His Ala Val Gly
705                 710                 715                 720

Gly Leu Arg Asp Thr Val Pro Pro Phe Asp Pro Phe Asn His Ser Gly
                725                 730                 735

Leu Gly Trp Thr Phe Asp Arg Ala Glu Ala His Lys Leu Ile Glu Ala
            740                 745                 750

Leu Gly His Cys Leu Arg Thr Tyr Arg Asp Phe Lys Glu Ser Trp Arg
        755                 760                 765

Ala Leu Gln Glu Arg Gly Met Ser Gln Asp Phe Ser Trp Glu His Ala
770                 775                 780

Ala Lys Leu Tyr Glu Asp Val Leu Val Lys Ala Lys Tyr Gln Trp
785                 790                 795

<210> SEQ ID NO 5
<211> LENGTH: 2433
<212> TYPE: DNA
<213> ORGANISM: Oryza sativa
<220> FEATURE:
<221> NAME/KEY: CDS
<222> LOCATION: (1)..(2430)

<400> SEQUENCE: 5 atg tct agc gcg gtg gtt gcg tcc agc aca act ttt ctc gtc gca ctt    48
Met Ser Ser Ala Val Val Ala Ser Ser Thr Thr Phe Leu Val Ala Leu
1               5                   10                  15 gcc tct agc gcg agc cgg ggc ggg cca cgt agg ggg cgc gtc gtg ggc    96
Ala Ser Ser Ala Ser Arg Gly Gly Pro Arg Arg Gly Arg Val Val Gly
```

```
                 20                  25                  30
gtg gcc gct ccc cca gcc ctc ctg tat gac ggg aga gct ggc agg cta    144
Val Ala Ala Pro Pro Ala Leu Leu Tyr Asp Gly Arg Ala Gly Arg Leu
             35                  40                  45 gcc ctg cgc gcc cct ccg cca ccc cgc cct aga cct agg cgc agg gat    192
Ala Leu Arg Ala Pro Pro Pro Pro Arg Pro Arg Pro Arg Arg Arg Asp
 50                  55                  60 gcg ggt gtt gtc agg cgg gct gat gac ggg gag aac gag gcc gca gtg    240
Ala Gly Val Val Arg Arg Ala Asp Asp Gly Glu Asn Glu Ala Ala Val
 65                  70                  75                  80 gag cgg gcc ggc gag gac gat gac gag gag gag gag ttc tcg tcc ggg    288
Glu Arg Ala Gly Glu Asp Asp Asp Glu Glu Glu Glu Phe Ser Ser Gly
                 85                  90                  95 gcc tgg cag cca ccg cgt tca agg cgc ggt gga gtt ggc aag gtc ctc    336
Ala Trp Gln Pro Pro Arg Ser Arg Arg Gly Gly Val Gly Lys Val Leu
             100                 105                 110 aaa cgt cgc ggt acc gtg ccg cca gtc gga agg tac ggc tcc ggt gga    384
Lys Arg Arg Gly Thr Val Pro Pro Val Gly Arg Tyr Gly Ser Gly Gly
             115                 120                 125 gac gcc gct cgg gtg aga gga gcc gcg gca ccc gct cca gca ccg acg    432
Asp Ala Ala Arg Val Arg Gly Ala Ala Pro Ala Pro Ala Pro Thr
 130                 135                 140 caa gac gca gcg tcg tct aag aat ggc gcg ctt ttg tca ggc agg gat    480
Gln Asp Ala Ala Ser Ser Lys Asn Gly Ala Leu Leu Ser Gly Arg Asp
145                 150                 155                 160 gac gac aca cct gcc tca cgg aac gga tcg gtc gtt acc ggc gcc gac    528
Asp Asp Thr Pro Ala Ser Arg Asn Gly Ser Val Val Thr Gly Ala Asp
                 165                 170                 175 aag cct gcc gcc gcc acg ccg ccg gtg acc ata acg aag ctc cca gcg    576
Lys Pro Ala Ala Ala Thr Pro Pro Val Thr Ile Thr Lys Leu Pro Ala
             180                 185                 190 ccg gac tcc ccc gtg atc ctt cca tcc gta gac aag ccg cag ccg gag    624
Pro Asp Ser Pro Val Ile Leu Pro Ser Val Asp Lys Pro Gln Pro Glu
             195                 200                 205 ttc gtc atc cca gac gcg acg gcg ccg gcg ccg cca ccg ccc ggt tca    672
Phe Val Ile Pro Asp Ala Thr Ala Pro Ala Pro Pro Pro Pro Gly Ser
 210                 215                 220 aat ccc agg tcg tcc gct cct ctc ccc aag cct gac aat tcg gaa ttt    720
Asn Pro Arg Ser Ser Ala Pro Leu Pro Lys Pro Asp Asn Ser Glu Phe
225                 230                 235                 240 gca gag gat aag agc gca aaa gtt gtt gag agt gct ccg aag cca aag    768
Ala Glu Asp Lys Ser Ala Lys Val Val Glu Ser Ala Pro Lys Pro Lys
                 245                 250                 255 gcg act aga tct tcc cct att cct gcg gta gaa gag gag acg tgg gat    816
Ala Thr Arg Ser Ser Pro Ile Pro Ala Val Glu Glu Glu Thr Trp Asp
             260                 265                 270 ttc aag aaa tat ttt gat ctg aac gaa ccg gac gcc gcg gag gat ggc    864
Phe Lys Lys Tyr Phe Asp Leu Asn Glu Pro Asp Ala Ala Glu Asp Gly
             275                 280                 285 gat gac gat gat gac tgg gct gat tca gat gcg tca gat tct gag atc    912
Asp Asp Asp Asp Asp Trp Ala Asp Ser Asp Ala Ser Asp Ser Glu Ile
 290                 295                 300 gac cag gat gac gat tcg ggt cct ttg gct ggg gag aat gtc atg aac    960
Asp Gln Asp Asp Asp Ser Gly Pro Leu Ala Gly Glu Asn Val Met Asn
305                 310                 315                 320 gtg atc gtg gtg gct gct gaa tgt tct ccc tgg tgc aaa aca ggt ggg   1008
Val Ile Val Val Ala Ala Glu Cys Ser Pro Trp Cys Lys Thr Gly Gly
                 325                 330                 335 ctt gga gat gtt gca ggt gct tta ccc aag gct ttg gcg agg aga gga   1056
Leu Gly Asp Val Ala Gly Ala Leu Pro Lys Ala Leu Ala Arg Arg Gly
```

```
                     340                 345                 350
cat cgt gtt atg gtt gtc gta cca agg tac ggt gat tac gcg gaa gcc    1104
His Arg Val Met Val Val Val Pro Arg Tyr Gly Asp Tyr Ala Glu Ala
        355                 360                 365 cag gat gta gga atc agg aaa tac tac aag gct gct gga cag gat ctg    1152
Gln Asp Val Gly Ile Arg Lys Tyr Tyr Lys Ala Ala Gly Gln Asp Leu
370                 375                 380 gaa gtg aaa tat ttc cat gca ttt atc gac gga gtt gat ttt gtg ttc    1200
Glu Val Lys Tyr Phe His Ala Phe Ile Asp Gly Val Asp Phe Val Phe
385                 390                 395                 400 att gac gct cct ctc ttc cgt cac cgt cag gat gac atc tat ggg ggg    1248
Ile Asp Ala Pro Leu Phe Arg His Arg Gln Asp Asp Ile Tyr Gly Gly
            405                 410                 415 aac aga cag gaa atc atg aag cgc atg att ctg ttt tgt aag gct gct    1296
Asn Arg Gln Glu Ile Met Lys Arg Met Ile Leu Phe Cys Lys Ala Ala
        420                 425                 430 gtt gag gtt cct tgg cac gtt cca tgc ggt ggt gtg ccc tat ggg gat    1344
Val Glu Val Pro Trp His Val Pro Cys Gly Gly Val Pro Tyr Gly Asp
                435                 440                 445 ggc aac ttg gtg ttc ctt gca aac gat tgg cac act gca ctc ctg cct    1392
Gly Asn Leu Val Phe Leu Ala Asn Asp Trp His Thr Ala Leu Leu Pro
450                 455                 460 gtt tat ctg aag gca tat tac aga gac aat ggc atg atg cag tac act    1440
Val Tyr Leu Lys Ala Tyr Tyr Arg Asp Asn Gly Met Met Gln Tyr Thr
465                 470                 475                 480 cgc tct gtc ctt gtg ata cat aat atc gct tac cag ggc cgt ggc cca    1488
Arg Ser Val Leu Val Ile His Asn Ile Ala Tyr Gln Gly Arg Gly Pro
            485                 490                 495 gta gat gaa ttc ccc tac atg gaa ttg ccg gag cac tac ctg gat cac    1536
Val Asp Glu Phe Pro Tyr Met Glu Leu Pro Glu His Tyr Leu Asp His
                500                 505                 510 ttc aag ctg tac gac ccc gtc ggc ggc gag cac gcc aac atc ttc ggc    1584
Phe Lys Leu Tyr Asp Pro Val Gly Gly Glu His Ala Asn Ile Phe Gly
        515                 520                 525 gcg ggc ctg aag atg gcg gac cgg gtg gtg acc gtg agc ccc ggc tac    1632
Ala Gly Leu Lys Met Ala Asp Arg Val Val Thr Val Ser Pro Gly Tyr
530                 535                 540 ctc tgg gag ctg aag acg acg gag ggc ggc tgg ggc ctc cac gac atc    1680
Leu Trp Glu Leu Lys Thr Thr Glu Gly Gly Trp Gly Leu His Asp Ile
545                 550                 555                 560 ata cgg gag aac gac tgg aag atg aac ggc atc gtg aac ggc atc gac    1728
Ile Arg Glu Asn Asp Trp Lys Met Asn Gly Ile Val Asn Gly Ile Asp
            565                 570                 575 tac cgg gag tgg aac ccg gag gtg gac gtg cac ctg cag tcc gac ggc    1776
Tyr Arg Glu Trp Asn Pro Glu Val Asp Val His Leu Gln Ser Asp Gly
                580                 585                 590 tac gcc aac tac acc gtg gcc tcg ctg gac tcc agc aag ccg cgg tgc    1824
Tyr Ala Asn Tyr Thr Val Ala Ser Leu Asp Ser Ser Lys Pro Arg Cys
        595                 600                 605 aag gcg gcg ctg cag cgc gag ctg ggg ctg gag gtg cgc gac gac gtg    1872
Lys Ala Ala Leu Gln Arg Glu Leu Gly Leu Glu Val Arg Asp Asp Val
610                 615                 620 ccg ctg atc ggg ttc atc ggg cgg ctc gac ggg cag aaa ggt gtg gac    1920
Pro Leu Ile Gly Phe Ile Gly Arg Leu Asp Gly Gln Lys Gly Val Asp
625                 630                 635                 640 atc atc ggc gac gcg atg ccg tgg atc gcc ggg cag gac gtg cag ctg    1968
Ile Ile Gly Asp Ala Met Pro Trp Ile Ala Gly Gln Asp Val Gln Leu
            645                 650                 655 gtg ctg ctg ggc tcc ggc cgc cgc gac ctg gag gtg atg ctg cag cgg    2016
Val Leu Leu Gly Ser Gly Arg Arg Asp Leu Glu Val Met Leu Gln Arg
```

-continued

```
                      660                 665                 670
ttc gag gcg cag cac aac agc aag gtg cgc ggg tgg gtg ggg ttc tcg      2064
Phe Glu Ala Gln His Asn Ser Lys Val Arg Gly Trp Val Gly Phe Ser
            675                 680                 685 gtg aag atg gcg cac cgg atc acg gcg ggc gcc gac gtg ctg gtc atg      2112
Val Lys Met Ala His Arg Ile Thr Ala Gly Ala Asp Val Leu Val Met
        690                 695                 700 ccg tcg cgg ttc gag ccg tgc ggc ctc aac cag ctc tac gcc atg gcg      2160
Pro Ser Arg Phe Glu Pro Cys Gly Leu Asn Gln Leu Tyr Ala Met Ala
705                 710                 715                 720 tac ggc acc gtc ccc gtc gtg cac gcc gtc ggc ggg ctg agg gac acc      2208
Tyr Gly Thr Val Pro Val Val His Ala Val Gly Gly Leu Arg Asp Thr
                725                 730                 735 gtg tcg gcg ttc gac ccg ttc gag gac acc ggc ctc ggg tgg acg ttc      2256
Val Ser Ala Phe Asp Pro Phe Glu Asp Thr Gly Leu Gly Trp Thr Phe
            740                 745                 750 gac cgc gcc gag ccg cac aag ctc atc gag gcg ctc ggc cac tgc ctg      2304
Asp Arg Ala Glu Pro His Lys Leu Ile Glu Ala Leu Gly His Cys Leu
        755                 760                 765 gag acg tac cgc aag tac aag gag agc tgg agg ggg ctc cag gtg cgc      2352
Glu Thr Tyr Arg Lys Tyr Lys Glu Ser Trp Arg Gly Leu Gln Val Arg
770                 775                 780 ggc atg tcg cag gac ctc agc tgg gac cac gcc gcc gag ctc tac gag      2400
Gly Met Ser Gln Asp Leu Ser Trp Asp His Ala Ala Glu Leu Tyr Glu
785                 790                 795                 800 gag gtc ctt gtc aag gcc aag tac caa tgg tga                          2433
Glu Val Leu Val Lys Ala Lys Tyr Gln Trp
                805                 810

<210> SEQ ID NO 6
<211> LENGTH: 810
<212> TYPE: PRT
<213> ORGANISM: Oryza sativa

<400> SEQUENCE: 6

Met Ser Ser Ala Val Ala Ser Ser Thr Thr Phe Leu Val Ala Leu
1               5                   10                  15

Ala Ser Ser Ala Ser Arg Gly Gly Pro Arg Arg Gly Arg Val Val Gly
            20                  25                  30

Val Ala Ala Pro Pro Ala Leu Leu Tyr Asp Gly Arg Ala Gly Arg Leu
        35                  40                  45

Ala Leu Arg Ala Pro Pro Pro Arg Pro Arg Pro Arg Arg Arg Asp
    50                  55                  60

Ala Gly Val Val Arg Arg Ala Asp Asp Gly Glu Asn Glu Ala Ala Val
65                  70                  75                  80

Glu Arg Ala Gly Glu Asp Asp Glu Glu Glu Phe Ser Ser Gly
                85                  90                  95

Ala Trp Gln Pro Pro Arg Ser Arg Arg Gly Gly Val Gly Lys Val Leu
            100                 105                 110

Lys Arg Arg Gly Thr Val Pro Pro Val Gly Arg Tyr Gly Ser Gly Gly
        115                 120                 125

Asp Ala Ala Arg Val Arg Gly Ala Ala Ala Pro Ala Pro Ala Pro Thr
    130                 135                 140

Gln Asp Ala Ala Ser Ser Lys Asn Gly Ala Leu Leu Ser Gly Arg Asp
145                 150                 155                 160

Asp Asp Thr Pro Ala Ser Arg Asn Gly Ser Val Val Thr Gly Ala Asp
                165                 170                 175

Lys Pro Ala Ala Ala Thr Pro Pro Val Thr Ile Thr Lys Leu Pro Ala
```

```
                180               185               190
Pro Asp Ser Pro Val Ile Leu Pro Ser Val Asp Lys Pro Gln Pro Glu
            195               200               205
Phe Val Ile Pro Asp Ala Thr Ala Pro Ala Pro Pro Pro Gly Ser
            210               215               220
Asn Pro Arg Ser Ser Ala Pro Leu Pro Lys Pro Asp Asn Ser Glu Phe
225               230               235               240
Ala Glu Asp Lys Ser Ala Lys Val Val Glu Ser Ala Pro Lys Pro Lys
            245               250               255
Ala Thr Arg Ser Ser Pro Ile Pro Ala Val Glu Glu Thr Trp Asp
            260               265               270
Phe Lys Lys Tyr Phe Asp Leu Asn Glu Pro Asp Ala Ala Glu Asp Gly
            275               280               285
Asp Asp Asp Asp Asp Trp Ala Asp Ser Asp Ala Ser Asp Ser Glu Ile
            290               295               300
Asp Gln Asp Asp Asp Ser Gly Pro Leu Ala Gly Glu Asn Val Met Asn
305               310               315               320
Val Ile Val Val Ala Ala Glu Cys Ser Pro Trp Cys Lys Thr Gly Gly
                325               330               335
Leu Gly Asp Val Ala Gly Ala Leu Pro Lys Ala Leu Ala Arg Arg Gly
            340               345               350
His Arg Val Met Val Val Pro Arg Tyr Gly Asp Tyr Ala Glu Ala
            355               360               365
Gln Asp Val Gly Ile Arg Lys Tyr Tyr Lys Ala Ala Gly Gln Asp Leu
            370               375               380
Glu Val Lys Tyr Phe His Ala Phe Ile Asp Gly Val Asp Phe Val Phe
385               390               395               400
Ile Asp Ala Pro Leu Phe Arg His Arg Gln Asp Ile Tyr Gly Gly
            405               410               415
Asn Arg Gln Glu Ile Met Lys Arg Met Ile Leu Phe Cys Lys Ala Ala
            420               425               430
Val Glu Val Pro Trp His Val Pro Cys Gly Gly Val Pro Tyr Gly Asp
            435               440               445
Gly Asn Leu Val Phe Leu Ala Asn Asp Trp His Thr Ala Leu Leu Pro
450               455               460
Val Tyr Leu Lys Ala Tyr Tyr Arg Asp Asn Gly Met Met Gln Tyr Thr
465               470               475               480
Arg Ser Val Leu Val Ile His Asn Ile Ala Tyr Gln Gly Arg Gly Pro
            485               490               495
Val Asp Glu Phe Pro Tyr Met Glu Leu Pro Glu His Tyr Leu Asp His
            500               505               510
Phe Lys Leu Tyr Asp Pro Val Gly Gly Glu His Ala Asn Ile Phe Gly
            515               520               525
Ala Gly Leu Lys Met Ala Asp Arg Val Val Thr Val Ser Pro Gly Tyr
            530               535               540
Leu Trp Glu Leu Lys Thr Thr Glu Gly Gly Trp Gly Leu His Asp Ile
545               550               555               560
Ile Arg Glu Asn Asp Trp Lys Met Asn Gly Ile Val Asn Gly Ile Asp
                565               570               575
Tyr Arg Glu Trp Asn Pro Glu Val Asp Val His Leu Gln Ser Asp Gly
            580               585               590
Tyr Ala Asn Tyr Thr Val Ala Ser Leu Asp Ser Ser Lys Pro Arg Cys
            595               600               605
```

```
Lys Ala Ala Leu Gln Arg Glu Leu Gly Leu Glu Val Arg Asp Asp Val
        610                 615                 620

Pro Leu Ile Gly Phe Ile Gly Arg Leu Asp Gly Gln Lys Gly Val Asp
625                 630                 635                 640

Ile Ile Gly Asp Ala Met Pro Trp Ile Ala Gly Gln Asp Val Gln Leu
                645                 650                 655

Val Leu Gly Ser Gly Arg Arg Asp Leu Glu Val Met Leu Gln Arg
            660                 665                 670

Phe Glu Ala Gln His Asn Ser Lys Val Arg Gly Trp Val Gly Phe Ser
        675                 680                 685

Val Lys Met Ala His Arg Ile Thr Ala Gly Ala Asp Val Leu Val Met
    690                 695                 700

Pro Ser Arg Phe Glu Pro Cys Gly Leu Asn Gln Leu Tyr Ala Met Ala
705                 710                 715                 720

Tyr Gly Thr Val Pro Val Val His Ala Val Gly Gly Leu Arg Asp Thr
                725                 730                 735

Val Ser Ala Phe Asp Pro Phe Glu Asp Thr Gly Leu Gly Trp Thr Phe
            740                 745                 750

Asp Arg Ala Glu Pro His Lys Leu Ile Glu Ala Leu Gly His Cys Leu
        755                 760                 765

Glu Thr Tyr Arg Lys Tyr Lys Glu Ser Trp Arg Gly Leu Gln Val Arg
    770                 775                 780

Gly Met Ser Gln Asp Leu Ser Trp Asp His Ala Ala Glu Leu Tyr Glu
785                 790                 795                 800

Glu Val Leu Val Lys Ala Lys Tyr Gln Trp
                805                 810

<210> SEQ ID NO 7
<211> LENGTH: 1830
<212> TYPE: DNA
<213> ORGANISM: Oryza sativa
<220> FEATURE:
<221> NAME/KEY: CDS
<222> LOCATION: (1)..(1827)

<400> SEQUENCE: 7 atg tcg gct ctc acc acg tcc cag ctc gcc acc tcg gcc acc ggc ttc      48
Met Ser Ala Leu Thr Thr Ser Gln Leu Ala Thr Ser Ala Thr Gly Phe
1               5                   10                  15 ggc atc gcc gac agg tcg gcg ccg tcg tcg ctg ctc cgc cac ggg ttc      96
Gly Ile Ala Asp Arg Ser Ala Pro Ser Ser Leu Leu Arg His Gly Phe
            20                  25                  30 cag ggc ctc aag ccc cgc agc ccc gcc ggc ggc gac gcg acg tcg ctc     144
Gln Gly Leu Lys Pro Arg Ser Pro Ala Gly Gly Asp Ala Thr Ser Leu
        35                  40                  45 agc gtg acg acc agc gcg cgc gcg acg ccc aag cag cag cgg tcg gtg     192
Ser Val Thr Thr Ser Ala Arg Ala Thr Pro Lys Gln Gln Arg Ser Val
    50                  55                  60 cag cgt ggc agc cgg agg ttc ccc tcc gtc gtc gtg tac gcc acc ggc     240
Gln Arg Gly Ser Arg Arg Phe Pro Ser Val Val Val Tyr Ala Thr Gly
65                  70                  75                  80 gcc ggc atg aac gtc gtg ttc gtc ggc gcc gag atg gcc ccc tgg agc     288
Ala Gly Met Asn Val Val Phe Val Gly Ala Glu Met Ala Pro Trp Ser
                85                  90                  95 aag acc ggc ggc ctc ggt gac gtc ctc ggt ggc ctc ccc cct gcc atg     336
Lys Thr Gly Gly Leu Gly Asp Val Leu Gly Gly Leu Pro Pro Ala Met
            100                 105                 110 gct gcg aat ggc cac agg gtc atg gtg atc tct cct cgg tac gac cag     384
Ala Ala Asn Gly His Arg Val Met Val Ile Ser Pro Arg Tyr Asp Gln
```

-continued

```
                    115                 120                    125
tac aag gac gct tgg gat acc agc gtt gtg gct gag atc aag gtt gca       432
Tyr Lys Asp Ala Trp Asp Thr Ser Val Val Ala Glu Ile Lys Val Ala
        130                 135                 140 gac agg tac gag agg gtg agg ttt ttc cat tgc tac aag cgt gga gtc       480
Asp Arg Tyr Glu Arg Val Arg Phe Phe His Cys Tyr Lys Arg Gly Val
145                 150                 155                 160 gac cgt gtg ttc atc gac cat ccg tca ttc ctg gag aag gtt tgg gga       528
Asp Arg Val Phe Ile Asp His Pro Ser Phe Leu Glu Lys Val Trp Gly
                165                 170                 175 aag acc ggt gag aag atc tac gga cct gac act gga gtt gat tac aaa       576
Lys Thr Gly Glu Lys Ile Tyr Gly Pro Asp Thr Gly Val Asp Tyr Lys
            180                 185                 190 gac aac cag atg cgt ttc agc ctt ctt tgc cag gca gca ctc gag gct       624
Asp Asn Gln Met Arg Phe Ser Leu Leu Cys Gln Ala Ala Leu Glu Ala
        195                 200                 205 cct agg atc cta aac ctc aac aac aac cca tac ttc aaa gga act tat       672
Pro Arg Ile Leu Asn Leu Asn Asn Asn Pro Tyr Phe Lys Gly Thr Tyr
    210                 215                 220 ggt gag gat gtt gtg ttc gtc tgc aac gac tgg cac act ggc cca ctg       720
Gly Glu Asp Val Val Phe Val Cys Asn Asp Trp His Thr Gly Pro Leu
225                 230                 235                 240 gcg agc tac ctg aag aac aac tac cag ccc aat ggc atc tac agg aat       768
Ala Ser Tyr Leu Lys Asn Asn Tyr Gln Pro Asn Gly Ile Tyr Arg Asn
                245                 250                 255 gca aag gtt gct ttc tgc atc cac aac atc tcc tac cag ggc cgt ttc       816
Ala Lys Val Ala Phe Cys Ile His Asn Ile Ser Tyr Gln Gly Arg Phe
            260                 265                 270 gct ttc gag gat tac cct gag ctg aac ctc tcc gag agg ttc agg tca       864
Ala Phe Glu Asp Tyr Pro Glu Leu Asn Leu Ser Glu Arg Phe Arg Ser
        275                 280                 285 tcc ttc gat ttc atc gac ggg tat gac acg ccg gtg gag ggc agg aag       912
Ser Phe Asp Phe Ile Asp Gly Tyr Asp Thr Pro Val Glu Gly Arg Lys
    290                 295                 300 atc aac tgg atg aag gcc gga atc ctg gaa gcc gac agg gtg ctc acc       960
Ile Asn Trp Met Lys Ala Gly Ile Leu Glu Ala Asp Arg Val Leu Thr
305                 310                 315                 320 gtg agc ccg tac tac gcc gag gag ctc atc tcc ggc atc gcc agg gga       1008
Val Ser Pro Tyr Tyr Ala Glu Glu Leu Ile Ser Gly Ile Ala Arg Gly
                325                 330                 335 tgc gag ctc gac aac atc atg cgg ctc acc ggc atc acc ggc atc gtc       1056
Cys Glu Leu Asp Asn Ile Met Arg Leu Thr Gly Ile Thr Gly Ile Val
            340                 345                 350 aac ggc atg gac gtc agc gag tgg gat ccc agc aag gac aag tac atc       1104
Asn Gly Met Asp Val Ser Glu Trp Asp Pro Ser Lys Asp Lys Tyr Ile
        355                 360                 365 acc gcc aag tac gac gca acc acg gca atc gag gcg aag gcg ctg aac       1152
Thr Ala Lys Tyr Asp Ala Thr Thr Ala Ile Glu Ala Lys Ala Leu Asn
    370                 375                 380 aag gag gcg ttg cag gcg gag gcg ggt ctt ccg gtc gac agg aaa atc       1200
Lys Glu Ala Leu Gln Ala Glu Ala Gly Leu Pro Val Asp Arg Lys Ile
385                 390                 395                 400 cca ctg atc gcg ttc atc ggc agg ctg gag gaa cag aag ggc tct gac       1248
Pro Leu Ile Ala Phe Ile Gly Arg Leu Glu Glu Gln Lys Gly Ser Asp
                405                 410                 415 gtc atg gcc gcc gcc atc ccg gag ctc atg cag gag gac gtc cag atc       1296
Val Met Ala Ala Ala Ile Pro Glu Leu Met Gln Glu Asp Val Gln Ile
            420                 425                 430 gtt ctt ctg ggt act gga aag aag aag ttc gag aag ctg ctc aag agc       1344
Val Leu Leu Gly Thr Gly Lys Lys Lys Phe Glu Lys Leu Leu Lys Ser
```

```
                  435                 440                 445
atg gag gag aag tat ccg ggc aag gtg agg gcc gtg gtg aag ttc aac      1392
Met Glu Glu Lys Tyr Pro Gly Lys Val Arg Ala Val Val Lys Phe Asn
    450                 455                 460 gcg ccg ctt gct cat ctc atc atg gcc gga gcc gac gtg ctc gcc gtc      1440
Ala Pro Leu Ala His Leu Ile Met Ala Gly Ala Asp Val Leu Ala Val
465                 470                 475                 480 ccc agc cgc ttc gag ccc tgt gga ctc atc cag ctg cag ggg atg aga      1488
Pro Ser Arg Phe Glu Pro Cys Gly Leu Ile Gln Leu Gln Gly Met Arg
                485                 490                 495 tac gga acg ccc tgt gct tgc gcg tcc acc ggt ggg ctc gtg gac acg      1536
Tyr Gly Thr Pro Cys Ala Cys Ala Ser Thr Gly Gly Leu Val Asp Thr
            500                 505                 510 gtc atc gaa ggc aag act ggt ttc cac atg ggc cgt ctc agc gtc gac      1584
Val Ile Glu Gly Lys Thr Gly Phe His Met Gly Arg Leu Ser Val Asp
        515                 520                 525 tgc aag gtg gtg gag cca agc gac gtg aag aag gtg gcg gcc acc ctg      1632
Cys Lys Val Val Glu Pro Ser Asp Val Lys Lys Val Ala Ala Thr Leu
    530                 535                 540 aag cgc gcc atc aag gtc gtc ggc acg ccg gcg tac gag gag atg gtc      1680
Lys Arg Ala Ile Lys Val Val Gly Thr Pro Ala Tyr Glu Glu Met Val
545                 550                 555                 560 agg aac tgc atg aac cag gac ctc tcc tgg aag ggg cct gcg aag aac      1728
Arg Asn Cys Met Asn Gln Asp Leu Ser Trp Lys Gly Pro Ala Lys Asn
                565                 570                 575 tgg gag aat gtg ctc ctg ggc ctg ggc gtc gcc ggc agc gcg ccg ggg      1776
Trp Glu Asn Val Leu Leu Gly Leu Gly Val Ala Gly Ser Ala Pro Gly
            580                 585                 590 atc gaa ggc gac gag atc gcg ccg ctc gcc aag gag aac gtg gct gct      1824
Ile Glu Gly Asp Glu Ile Ala Pro Leu Ala Lys Glu Asn Val Ala Ala
        595                 600                 605 cct tga                                                               1830
Pro
```

<210> SEQ ID NO 8
<211> LENGTH: 609
<212> TYPE: PRT
<213> ORGANISM: Oryza sativa

<400> SEQUENCE: 8

```
Met Ser Ala Leu Thr Thr Ser Gln Leu Ala Thr Ser Ala Thr Gly Phe
1               5                   10                  15

Gly Ile Ala Asp Arg Ser Ala Pro Ser Ser Leu Leu Arg His Gly Phe
                20                  25                  30

Gln Gly Leu Lys Pro Arg Ser Pro Ala Gly Gly Asp Ala Thr Ser Leu
            35                  40                  45

Ser Val Thr Thr Ser Ala Arg Ala Thr Pro Lys Gln Gln Arg Ser Val
        50                  55                  60

Gln Arg Gly Ser Arg Arg Phe Pro Ser Val Val Tyr Ala Thr Gly
    65                  70                  75                  80

Ala Gly Met Asn Val Val Phe Val Gly Ala Glu Met Ala Pro Trp Ser
                85                  90                  95

Lys Thr Gly Gly Leu Gly Asp Val Leu Gly Gly Leu Pro Pro Ala Met
                100                 105                 110

Ala Ala Asn Gly His Arg Val Met Val Ile Ser Pro Arg Tyr Asp Gln
            115                 120                 125

Tyr Lys Asp Ala Trp Asp Thr Ser Val Val Ala Glu Ile Lys Val Ala
        130                 135                 140
```

-continued

```
Asp Arg Tyr Glu Arg Val Arg Phe Phe His Cys Tyr Lys Arg Gly Val
145                 150                 155                 160

Asp Arg Val Phe Ile Asp His Pro Ser Phe Leu Glu Lys Val Trp Gly
            165                 170                 175

Lys Thr Gly Glu Lys Ile Tyr Gly Pro Asp Thr Gly Val Asp Tyr Lys
        180                 185                 190

Asp Asn Gln Met Arg Phe Ser Leu Leu Cys Gln Ala Ala Leu Glu Ala
    195                 200                 205

Pro Arg Ile Leu Asn Leu Asn Asn Pro Tyr Phe Lys Gly Thr Tyr
210                 215                 220

Gly Glu Asp Val Val Phe Val Cys Asn Asp Trp His Thr Gly Pro Leu
225                 230                 235                 240

Ala Ser Tyr Leu Lys Asn Asn Tyr Gln Pro Asn Gly Ile Tyr Arg Asn
                245                 250                 255

Ala Lys Val Ala Phe Cys Ile His Asn Ile Ser Tyr Gln Gly Arg Phe
            260                 265                 270

Ala Phe Glu Asp Tyr Pro Glu Leu Asn Leu Ser Glu Arg Phe Arg Ser
        275                 280                 285

Ser Phe Asp Phe Ile Asp Gly Tyr Asp Thr Pro Val Glu Gly Arg Lys
    290                 295                 300

Ile Asn Trp Met Lys Ala Gly Ile Leu Glu Ala Asp Arg Val Leu Thr
305                 310                 315                 320

Val Ser Pro Tyr Tyr Ala Glu Glu Leu Ile Ser Gly Ile Ala Arg Gly
                325                 330                 335

Cys Glu Leu Asp Asn Ile Met Arg Leu Thr Gly Ile Thr Gly Ile Val
            340                 345                 350

Asn Gly Met Asp Val Ser Glu Trp Asp Pro Ser Lys Asp Lys Tyr Ile
        355                 360                 365

Thr Ala Lys Tyr Asp Ala Thr Thr Ala Ile Glu Ala Lys Ala Leu Asn
    370                 375                 380

Lys Glu Ala Leu Gln Ala Glu Ala Gly Leu Pro Val Asp Arg Lys Ile
385                 390                 395                 400

Pro Leu Ile Ala Phe Ile Gly Arg Leu Glu Glu Gln Lys Gly Ser Asp
                405                 410                 415

Val Met Ala Ala Ala Ile Pro Glu Leu Met Gln Glu Asp Val Gln Ile
            420                 425                 430

Val Leu Leu Gly Thr Gly Lys Lys Lys Phe Glu Lys Leu Leu Lys Ser
        435                 440                 445

Met Glu Glu Lys Tyr Pro Gly Lys Val Arg Ala Val Lys Phe Asn
    450                 455                 460

Ala Pro Leu Ala His Leu Ile Met Ala Gly Ala Asp Val Leu Ala Val
465                 470                 475                 480

Pro Ser Arg Phe Glu Pro Cys Gly Leu Ile Gln Leu Gln Gly Met Arg
                485                 490                 495

Tyr Gly Thr Pro Cys Ala Cys Ala Ser Thr Gly Gly Leu Val Asp Thr
            500                 505                 510

Val Ile Glu Gly Lys Thr Gly Phe His Met Gly Arg Leu Ser Val Asp
        515                 520                 525

Cys Lys Val Val Glu Pro Ser Asp Val Lys Lys Val Ala Ala Thr Leu
    530                 535                 540

Lys Arg Ala Ile Lys Val Val Gly Thr Pro Ala Tyr Glu Glu Met Val
545                 550                 555                 560

Arg Asn Cys Met Asn Gln Asp Leu Ser Trp Lys Gly Pro Ala Lys Asn
                565                 570                 575
```

```
Trp Glu Asn Val Leu Leu Gly Leu Gly Val Ala Gly Ser Ala Pro Gly
            580                 585                 590

Ile Glu Gly Asp Glu Ile Ala Pro Leu Ala Lys Glu Asn Val Ala Ala
        595                 600                 605

Pro

<210> SEQ ID NO 9
<211> LENGTH: 1818
<212> TYPE: DNA
<213> ORGANISM: Triticum aestivum
<220> FEATURE:
<221> NAME/KEY: CDS
<222> LOCATION: (1)..(1815)

<400> SEQUENCE: 9 atg gcg gct ctg gtc acg tcg cag ctc gcc acc tcc ggc acc gtc ctc      48
Met Ala Ala Leu Val Thr Ser Gln Leu Ala Thr Ser Gly Thr Val Leu
1               5                   10                  15 ggc atc acc gac agg ttc cgg cgt gca ggt ttt cag ggt gtg agg ccc      96
Gly Ile Thr Asp Arg Phe Arg Arg Ala Gly Phe Gln Gly Val Arg Pro
                20                  25                  30 cgg agc ccg gca gat gcg ccg ctc ggc atg agg act acc gga gcg agc     144
Arg Ser Pro Ala Asp Ala Pro Leu Gly Met Arg Thr Thr Gly Ala Ser
            35                  40                  45 gcc gcc ccg aag caa caa agc cgg aaa gcg cac cgc ggg acc cgg cgg     192
Ala Ala Pro Lys Gln Gln Ser Arg Lys Ala His Arg Gly Thr Arg Arg
        50                  55                  60 tgc ctc tcc atg gtg gtg cgc gcc acg ggc agc gcc ggc atg aac ctc     240
Cys Leu Ser Met Val Val Arg Ala Thr Gly Ser Ala Gly Met Asn Leu
65                  70                  75                  80 gtg ttc gtc ggc gcc gag atg gcg ccc tgg agc aag acc ggc ggc ctc     288
Val Phe Val Gly Ala Glu Met Ala Pro Trp Ser Lys Thr Gly Gly Leu
                85                  90                  95 ggc gac gtc ctc ggg ggc ctc ccc cca gcc atg gcc gcc aac ggt cac     336
Gly Asp Val Leu Gly Gly Leu Pro Pro Ala Met Ala Ala Asn Gly His
            100                 105                 110 cgg gtc atg gtc atc tcc ccg cgc tac gac cag tac aag gac gcc tgg     384
Arg Val Met Val Ile Ser Pro Arg Tyr Asp Gln Tyr Lys Asp Ala Trp
        115                 120                 125 gac acc agc gtc gtc tcc gag atc aag gtc gcg gac gag tac gag agg     432
Asp Thr Ser Val Val Ser Glu Ile Lys Val Ala Asp Glu Tyr Glu Arg
    130                 135                 140 gtg agg tac ttc cac tgc tac aag cgc ggg gtg gac cgc gtg ttc gtc     480
Val Arg Tyr Phe His Cys Tyr Lys Arg Gly Val Asp Arg Val Phe Val
145                 150                 155                 160 gac cac ccg tgc ttc ctg gag aag gtc cgg ggc aag acc aag gag aag     528
Asp His Pro Cys Phe Leu Glu Lys Val Arg Gly Lys Thr Lys Glu Lys
                165                 170                 175 atc tac ggg ccc gat gcc ggc acg gac tac gag gac aac cag cta cgc     576
Ile Tyr Gly Pro Asp Ala Gly Thr Asp Tyr Glu Asp Asn Gln Leu Arg
            180                 185                 190 ttc agc ctg ctc tgc cag gca gcg ctt gag gca ccc agg atc ctc gac     624
Phe Ser Leu Leu Cys Gln Ala Ala Leu Glu Ala Pro Arg Ile Leu Asp
        195                 200                 205 ctc aac aac aac cca tac ttc tcc gga ccc tac ggg gaa gac gtg gtg     672
Leu Asn Asn Asn Pro Tyr Phe Ser Gly Pro Tyr Gly Glu Asp Val Val
    210                 215                 220 ttc gtg tgc aac gac tgg cac acg ggc ctt ctg gcc tgc tac ctc aag     720
Phe Val Cys Asn Asp Trp His Thr Gly Leu Leu Ala Cys Tyr Leu Lys
225                 230                 235                 240
```

| | | |
|---|---|---|
| agc aac tac cag tcc agt ggc atc tat agg acg gcc aag gta gcg ttc<br>Ser Asn Tyr Gln Ser Ser Gly Ile Tyr Arg Thr Ala Lys Val Ala Phe<br>245 250 255 | 768 | |
| tgc atc cac aac atc tcg tat cag ggc cgc ttc tcc ttc gac gac ttc<br>Cys Ile His Asn Ile Ser Tyr Gln Gly Arg Phe Ser Phe Asp Asp Phe<br>260 265 270 | 816 | |
| gcg cag ctc aac ctg ccc gac agg ttc aag tcg tcc ttc gac ttc atc<br>Ala Gln Leu Asn Leu Pro Asp Arg Phe Lys Ser Ser Phe Asp Phe Ile<br>275 280 285 | 864 | |
| gac ggc tac gac aag ccg gtg gag ggg cgc aag atc aac tgg atg aag<br>Asp Gly Tyr Asp Lys Pro Val Glu Gly Arg Lys Ile Asn Trp Met Lys<br>290 295 300 | 912 | |
| gcc ggg atc ctg cag gcc gac aag gtg ctc acg gtg agc ccc tac tac<br>Ala Gly Ile Leu Gln Ala Asp Lys Val Leu Thr Val Ser Pro Tyr Tyr<br>305 310 315 320 | 960 | |
| gcg gag gag ctc atc tcc ggc gaa gcc agg ggc tgc gag ctc gac aac<br>Ala Glu Glu Leu Ile Ser Gly Glu Ala Arg Gly Cys Glu Leu Asp Asn<br>325 330 335 | 1008 | |
| atc atg cgc ctc acg ggc atc acc ggc atc gtc aac ggc atg gac gtc<br>Ile Met Arg Leu Thr Gly Ile Thr Gly Ile Val Asn Gly Met Asp Val<br>340 345 350 | 1056 | |
| agc gag tgg gac ccc gcc aag gac aag ttc ctc gcc gcc aac tac gac<br>Ser Glu Trp Asp Pro Ala Lys Asp Lys Phe Leu Ala Ala Asn Tyr Asp<br>355 360 365 | 1104 | |
| gtc acc acc gcg ttg gag ggg aag gcg ctg aac aag gag gcg ctg cag<br>Val Thr Thr Ala Leu Glu Gly Lys Ala Leu Asn Lys Glu Ala Leu Gln<br>370 375 380 | 1152 | |
| gcc gag gtg ggg ctg ccg gtg gac cgg aag gtg ccc ctg gtg gcc ttc<br>Ala Glu Val Gly Leu Pro Val Asp Arg Lys Val Pro Leu Val Ala Phe<br>385 390 395 400 | 1200 | |
| atc ggc agg ctg gag gag cag aag ggc ccc gac gtg atg atc gcc gcc<br>Ile Gly Arg Leu Glu Glu Gln Lys Gly Pro Asp Val Met Ile Ala Ala<br>405 410 415 | 1248 | |
| atc ccg gag atc ttg aag gag gag gac gtc cag atc gtt ctc ctg ggc<br>Ile Pro Glu Ile Leu Lys Glu Glu Asp Val Gln Ile Val Leu Leu Gly<br>420 425 430 | 1296 | |
| acc ggg aag aag aag ttt gag cgg ctg ctc aag agc gtg gag gag aag<br>Thr Gly Lys Lys Lys Phe Glu Arg Leu Leu Lys Ser Val Glu Glu Lys<br>435 440 445 | 1344 | |
| ttc ccg agc aag gtg agg gcc gtg gtc agg ttc aac gcg ccg ctg gct<br>Phe Pro Ser Lys Val Arg Ala Val Val Arg Phe Asn Ala Pro Leu Ala<br>450 455 460 | 1392 | |
| cac cag atg atg gcc ggc gcc gac gtg ctc gcc gtc acc agc cgc ttc<br>His Gln Met Met Ala Gly Ala Asp Val Leu Ala Val Thr Ser Arg Phe<br>465 470 475 480 | 1440 | |
| gag ccc tgc ggc ctc atc cag ctc cag ggg atg cgc tac gga acg ccg<br>Glu Pro Cys Gly Leu Ile Gln Leu Gln Gly Met Arg Tyr Gly Thr Pro<br>485 490 495 | 1488 | |
| tgc gcg tgc gcg tcc acc ggc ggg ctc gtc gac acg atc atg gag ggc<br>Cys Ala Cys Ala Ser Thr Gly Gly Leu Val Asp Thr Ile Met Glu Gly<br>500 505 510 | 1536 | |
| aag acc ggg ttc cac atg ggc cgc ctc agc gtc gac tgc aac gtg gtg<br>Lys Thr Gly Phe His Met Gly Arg Leu Ser Val Asp Cys Asn Val Val<br>515 520 525 | 1584 | |
| gag ccg gcc gac gtg aag aag gtg gtg acc acc ctg aag cgc gcc gtc<br>Glu Pro Ala Asp Val Lys Lys Val Val Thr Thr Leu Lys Arg Ala Val<br>530 535 540 | 1632 | |
| aag gtc gtc ggc acg cca gcc tac cat gag atg gtc aag aac tgc atg<br>Lys Val Val Gly Thr Pro Ala Tyr His Glu Met Val Lys Asn Cys Met<br>545 550 555 560 | 1680 | |

```
atc cag gat ctc tcc tgg aag ggg cca gcc aag aac tgg gag gac gtg     1728
Ile Gln Asp Leu Ser Trp Lys Gly Pro Ala Lys Asn Trp Glu Asp Val
            565                 570                 575 ctt ctg gaa ctg ggg gtc gag ggg agc gag cca ggg gtc atc ggc gag     1776
Leu Leu Glu Leu Gly Val Glu Gly Ser Glu Pro Gly Val Ile Gly Glu
        580                 585                 590 gag att gcg ccg ctc gcc atg gag aac gtc gcc gct ccc tga             1818
Glu Ile Ala Pro Leu Ala Met Glu Asn Val Ala Ala Pro
    595                 600                 605

<210> SEQ ID NO 10
<211> LENGTH: 605
<212> TYPE: PRT
<213> ORGANISM: Triticum aestivum

<400> SEQUENCE: 10
```

Met Ala Ala Leu Val Thr Ser Gln Leu Ala Thr Ser Gly Thr Val Leu
1               5                   10                  15

Gly Ile Thr Asp Arg Phe Arg Arg Ala Gly Phe Gln Gly Val Arg Pro
            20                  25                  30

Arg Ser Pro Ala Asp Ala Pro Leu Gly Met Arg Thr Thr Gly Ala Ser
        35                  40                  45

Ala Ala Pro Lys Gln Gln Ser Arg Lys Ala His Arg Gly Thr Arg Arg
    50                  55                  60

Cys Leu Ser Met Val Val Arg Ala Thr Gly Ser Ala Gly Met Asn Leu
65                  70                  75                  80

Val Phe Val Gly Ala Glu Met Ala Pro Trp Ser Lys Thr Gly Gly Leu
                85                  90                  95

Gly Asp Val Leu Gly Gly Leu Pro Pro Ala Met Ala Ala Asn Gly His
            100                 105                 110

Arg Val Met Val Ile Ser Pro Arg Tyr Asp Gln Tyr Lys Asp Ala Trp
        115                 120                 125

Asp Thr Ser Val Val Ser Glu Ile Lys Val Ala Asp Glu Tyr Glu Arg
    130                 135                 140

Val Arg Tyr Phe His Cys Tyr Lys Arg Gly Val Asp Arg Val Phe Val
145                 150                 155                 160

Asp His Pro Cys Phe Leu Glu Lys Val Arg Gly Lys Thr Lys Glu Lys
                165                 170                 175

Ile Tyr Gly Pro Asp Ala Gly Thr Asp Tyr Glu Asp Asn Gln Leu Arg
            180                 185                 190

Phe Ser Leu Leu Cys Gln Ala Ala Leu Glu Ala Pro Arg Ile Leu Asp
        195                 200                 205

Leu Asn Asn Asn Pro Tyr Phe Ser Gly Pro Tyr Gly Glu Asp Val Val
    210                 215                 220

Phe Val Cys Asn Asp Trp His Thr Gly Leu Leu Ala Cys Tyr Leu Lys
225                 230                 235                 240

Ser Asn Tyr Gln Ser Ser Gly Ile Tyr Arg Thr Ala Lys Val Ala Phe
                245                 250                 255

Cys Ile His Asn Ile Ser Tyr Gln Gly Arg Phe Ser Phe Asp Asp Phe
            260                 265                 270

Ala Gln Leu Asn Leu Pro Asp Arg Phe Lys Ser Ser Phe Asp Phe Ile
        275                 280                 285

Asp Gly Tyr Asp Lys Pro Val Glu Gly Arg Lys Ile Asn Trp Met Lys
    290                 295                 300

Ala Gly Ile Leu Gln Ala Asp Lys Val Leu Thr Val Ser Pro Tyr Tyr
305                 310                 315                 320

```
Ala Glu Glu Leu Ile Ser Gly Glu Ala Arg Gly Cys Glu Leu Asp Asn
            325                 330                 335

Ile Met Arg Leu Thr Gly Ile Thr Gly Ile Val Asn Gly Met Asp Val
            340                 345                 350

Ser Glu Trp Asp Pro Ala Lys Asp Lys Phe Leu Ala Ala Asn Tyr Asp
            355                 360                 365

Val Thr Thr Ala Leu Glu Gly Lys Ala Leu Asn Lys Glu Ala Leu Gln
            370                 375                 380

Ala Glu Val Gly Leu Pro Val Asp Arg Lys Val Pro Leu Val Ala Phe
385                 390                 395                 400

Ile Gly Arg Leu Glu Glu Gln Lys Gly Pro Asp Val Met Ile Ala Ala
            405                 410                 415

Ile Pro Glu Ile Leu Lys Glu Glu Asp Val Gln Ile Val Leu Leu Gly
            420                 425                 430

Thr Gly Lys Lys Lys Phe Glu Arg Leu Leu Lys Ser Val Glu Glu Lys
            435                 440                 445

Phe Pro Ser Lys Val Arg Ala Val Val Arg Phe Asn Ala Pro Leu Ala
        450                 455                 460

His Gln Met Met Ala Gly Ala Asp Val Leu Ala Val Thr Ser Arg Phe
465                 470                 475                 480

Glu Pro Cys Gly Leu Ile Gln Leu Gln Gly Met Arg Tyr Gly Thr Pro
            485                 490                 495

Cys Ala Cys Ala Ser Thr Gly Gly Leu Val Asp Thr Ile Met Glu Gly
            500                 505                 510

Lys Thr Gly Phe His Met Gly Arg Leu Ser Val Asp Cys Asn Val Val
            515                 520                 525

Glu Pro Ala Asp Val Lys Lys Val Val Thr Thr Leu Lys Arg Ala Val
        530                 535                 540

Lys Val Val Gly Thr Pro Ala Tyr His Glu Met Val Lys Asn Cys Met
545                 550                 555                 560

Ile Gln Asp Leu Ser Trp Lys Gly Pro Ala Lys Asn Trp Glu Asp Val
            565                 570                 575

Leu Leu Glu Leu Gly Val Glu Gly Ser Glu Pro Gly Val Ile Gly Glu
            580                 585                 590

Glu Ile Ala Pro Leu Ala Met Glu Asn Val Ala Ala Pro
            595                 600                 605

<210> SEQ ID NO 11
<211> LENGTH: 1818
<212> TYPE: DNA
<213> ORGANISM: Zea mays
<220> FEATURE:
<221> NAME/KEY: CDS
<222> LOCATION: (1)..(1815)

<400> SEQUENCE: 11 atg gcg gct ctg gcc acg tcg cag ctc gtc gca acg cgc gcc ggc ctg      48
Met Ala Ala Leu Ala Thr Ser Gln Leu Val Ala Thr Arg Ala Gly Leu
1               5                   10                  15 ggc gtc ccg gac gcg tcc acg ttc cgc cgc ggc gcc gcg cag ggc ctg      96
Gly Val Pro Asp Ala Ser Thr Phe Arg Arg Gly Ala Ala Gln Gly Leu
            20                  25                  30 agg ggg gcc cgg gcg tcg gcg gcg gcg gac acg ctc agc atg cgg acc     144
Arg Gly Ala Arg Ala Ser Ala Ala Ala Asp Thr Leu Ser Met Arg Thr
        35                  40                  45 agc gcg cgc gcg gcg ccc agg cac cag cag cag gcg cgc cgg ggc ggc     192
Ser Ala Arg Ala Ala Pro Arg His Gln Gln Gln Ala Arg Arg Gly Gly
    50                  55                  60
```

```
agg ttc ccg tcg ctc gtc gtg tgc gcc agc gcc ggc atg aac gtc gtc      240
Arg Phe Pro Ser Leu Val Val Cys Ala Ser Ala Gly Met Asn Val Val
 65                  70                  75                  80 ttc gtc ggc gcc gag atg gcg ccg tgg agc aag acc ggc ggc ctc ggc      288
Phe Val Gly Ala Glu Met Ala Pro Trp Ser Lys Thr Gly Gly Leu Gly
                 85                  90                  95 gac gtc ctc ggc ggc ctg ccg ccg gcc atg gcc gcg aac ggg cac cgt      336
Asp Val Leu Gly Gly Leu Pro Pro Ala Met Ala Ala Asn Gly His Arg
            100                 105                 110 gtc atg gtc gtc tct ccc cgc tac gac cag tac aag gac gcc tgg gac      384
Val Met Val Val Ser Pro Arg Tyr Asp Gln Tyr Lys Asp Ala Trp Asp
        115                 120                 125 acc agc gtc gtg tcc gag atc aag atg gga gac ggg tac gag acg gtc      432
Thr Ser Val Val Ser Glu Ile Lys Met Gly Asp Gly Tyr Glu Thr Val
    130                 135                 140 agg ttc ttc cac tgc tac aag cgc gga gtg gac cgt gtg ttc gtt gac      480
Arg Phe Phe His Cys Tyr Lys Arg Gly Val Asp Arg Val Phe Val Asp
145                 150                 155                 160 cac cca ctg ttc ctg gag agg gtt tgg gga aag acc gag gag aag atc      528
His Pro Leu Phe Leu Glu Arg Val Trp Gly Lys Thr Glu Glu Lys Ile
                165                 170                 175 tac ggg cct gtc gct gga acg gac tac agg gac aac cag ctg cgg ttc      576
Tyr Gly Pro Val Ala Gly Thr Asp Tyr Arg Asp Asn Gln Leu Arg Phe
            180                 185                 190 agc ctg cta tgc cag gca gca ctt gaa gct cca agg atc ctg agc ctc      624
Ser Leu Leu Cys Gln Ala Ala Leu Glu Ala Pro Arg Ile Leu Ser Leu
        195                 200                 205 aac aac aac cca tac ttc tcc gga cca tac ggg gag gac gtc gtg ttc      672
Asn Asn Asn Pro Tyr Phe Ser Gly Pro Tyr Gly Glu Asp Val Val Phe
    210                 215                 220 gtc tgc aac gac tgg cac acc ggc cct ctc tcg tgc tac ctc aag agc      720
Val Cys Asn Asp Trp His Thr Gly Pro Leu Ser Cys Tyr Leu Lys Ser
225                 230                 235                 240 aac tac cag tcc cac ggc atc tac agg gac gca aag acc gct ttc tgc      768
Asn Tyr Gln Ser His Gly Ile Tyr Arg Asp Ala Lys Thr Ala Phe Cys
                245                 250                 255 atc cac aac atc tcc tac cag ggc cgg ttc gcc ttc tcc gac tac ccg      816
Ile His Asn Ile Ser Tyr Gln Gly Arg Phe Ala Phe Ser Asp Tyr Pro
            260                 265                 270 gag ctg aac ctc ccg gag aga ttc aag tcg tcc ttc gat ttc atc gac      864
Glu Leu Asn Leu Pro Glu Arg Phe Lys Ser Ser Phe Asp Phe Ile Asp
        275                 280                 285 ggc tac gag aag ccc gtg gaa ggc cgg aag atc aac tgg atg aag gcc      912
Gly Tyr Glu Lys Pro Val Glu Gly Arg Lys Ile Asn Trp Met Lys Ala
    290                 295                 300 ggg atc ctc gag gcc gac agg gtc ctc acc gtc agc ccc tac tac gca      960
Gly Ile Leu Glu Ala Asp Arg Val Leu Thr Val Ser Pro Tyr Tyr Ala
305                 310                 315                 320 gag gag ctc atc tcc ggc atc gcc agg ggc tgc gag ctc gac aac atc     1008
Glu Glu Leu Ile Ser Gly Ile Ala Arg Gly Cys Glu Leu Asp Asn Ile
                325                 330                 335 atg cgc ctc acc ggc atc acc ggc atc gtc aac ggc atg gac gtc agc     1056
Met Arg Leu Thr Gly Ile Thr Gly Ile Val Asn Gly Met Asp Val Ser
            340                 345                 350 gag tgg gac ccc agc agg gac aag tac atc gcc gtg aag tac gac gtg     1104
Glu Trp Asp Pro Ser Arg Asp Lys Tyr Ile Ala Val Lys Tyr Asp Val
        355                 360                 365 tcg acg gcc gtg gag gcc aag gcg ctg aac aag gag gcg ctg cag gcg     1152
Ser Thr Ala Val Glu Ala Lys Ala Leu Asn Lys Glu Ala Leu Gln Ala
    370                 375                 380
```

-continued

```
gag gtc ggg ctc ccg gtg gac cgg aac atc ccg ctg gtg gcg ttc atc        1200
Glu Val Gly Leu Pro Val Asp Arg Asn Ile Pro Leu Val Ala Phe Ile
385                 390                 395                 400 ggc agg ctg gaa gag cag aag ggc ccc gac gtc atg gcg gcc gcc atc        1248
Gly Arg Leu Glu Glu Gln Lys Gly Pro Asp Val Met Ala Ala Ala Ile
            405                 410                 415 ccg cag ctc atg gag atg gtg gag gac gtg cag atc gtt ctg ctg ggc        1296
Pro Gln Leu Met Glu Met Val Glu Asp Val Gln Ile Val Leu Leu Gly
        420                 425                 430 acg ggc aag aag aag ttc gag cgc atg ctc atg agc gcc gag gag aag        1344
Thr Gly Lys Lys Lys Phe Glu Arg Met Leu Met Ser Ala Glu Glu Lys
    435                 440                 445 ttc cca ggc aag gtg cgc gcc gtg gtc aag ttc aac gcg gcg ctg gcg        1392
Phe Pro Gly Lys Val Arg Ala Val Val Lys Phe Asn Ala Ala Leu Ala
450                 455                 460 cac cac atc atg gcc ggc gcc gac gtg ctc gcc gtc acc agc cgc ttc        1440
His His Ile Met Ala Gly Ala Asp Val Leu Ala Val Thr Ser Arg Phe
465                 470                 475                 480 gag ccc tgc ggc ctc atc cag ctg cag ggg atg cga tac gga acg ccc        1488
Glu Pro Cys Gly Leu Ile Gln Leu Gln Gly Met Arg Tyr Gly Thr Pro
            485                 490                 495 tgc gcc tgc gcg tcc acc ggt gga ctc gtc gac acc atc atc gaa ggc        1536
Cys Ala Cys Ala Ser Thr Gly Gly Leu Val Asp Thr Ile Ile Glu Gly
        500                 505                 510 aag acc ggg ttc cac atg ggc cgc ctc agc gtc gac tgt aac gtc gtg        1584
Lys Thr Gly Phe His Met Gly Arg Leu Ser Val Asp Cys Asn Val Val
    515                 520                 525 gag ccg gcg gac gtc aag aag gtg gcc acc aca ttg cag cgc gcc atc        1632
Glu Pro Ala Asp Val Lys Lys Val Ala Thr Thr Leu Gln Arg Ala Ile
530                 535                 540 aag gtg gtc ggc acg ccg gcg tac gag gag atg gtg agg aac tgc atg        1680
Lys Val Val Gly Thr Pro Ala Tyr Glu Glu Met Val Arg Asn Cys Met
545                 550                 555                 560 atc cag gat ctc tcc tgg aag ggc cct gcc aag aac tgg gag aac gtg        1728
Ile Gln Asp Leu Ser Trp Lys Gly Pro Ala Lys Asn Trp Glu Asn Val
            565                 570                 575 ctg ctc agc ctc ggg gtc gcc ggc ggc gag cca ggg gtc gaa ggc gag        1776
Leu Leu Ser Leu Gly Val Ala Gly Gly Glu Pro Gly Val Glu Gly Glu
        580                 585                 590 gag atc gcg ccg ctc gcc aag gag aac gtg gcc gcg ccc tga               1818
Glu Ile Ala Pro Leu Ala Lys Glu Asn Val Ala Ala Pro
    595                 600                 605

<210> SEQ ID NO 12
<211> LENGTH: 605
<212> TYPE: PRT
<213> ORGANISM: Zea mays

<400> SEQUENCE: 12

Met Ala Ala Leu Ala Thr Ser Gln Leu Val Ala Thr Arg Ala Gly Leu
1               5                   10                  15

Gly Val Pro Asp Ala Ser Thr Phe Arg Arg Gly Ala Ala Gln Gly Leu
            20                  25                  30

Arg Gly Ala Arg Ala Ser Ala Ala Asp Thr Leu Ser Met Arg Thr
        35                  40                  45

Ser Ala Arg Ala Ala Pro Arg His Gln Gln Gln Ala Arg Gly Gly
    50                  55                  60

Arg Phe Pro Ser Leu Val Val Cys Ala Ser Ala Gly Met Asn Val Val
65                  70                  75                  80
```

-continued

```
Phe Val Gly Ala Glu Met Ala Pro Trp Ser Lys Thr Gly Leu Gly
                 85                  90                  95

Asp Val Leu Gly Gly Leu Pro Pro Ala Met Ala Asn Gly His Arg
            100                 105                 110

Val Met Val Ser Pro Arg Tyr Asp Gln Tyr Lys Asp Ala Trp Asp
            115                 120                 125

Thr Ser Val Val Ser Glu Ile Lys Met Gly Asp Gly Tyr Glu Thr Val
    130                 135                 140

Arg Phe Phe His Cys Tyr Lys Arg Gly Val Asp Arg Val Phe Val Asp
145                 150                 155                 160

His Pro Leu Phe Leu Glu Arg Val Trp Gly Lys Thr Glu Glu Lys Ile
                165                 170                 175

Tyr Gly Pro Val Ala Gly Thr Asp Tyr Arg Asp Asn Gln Leu Arg Phe
            180                 185                 190

Ser Leu Leu Cys Gln Ala Ala Leu Glu Ala Pro Arg Ile Leu Ser Leu
            195                 200                 205

Asn Asn Asn Pro Tyr Phe Ser Gly Pro Tyr Gly Glu Asp Val Val Phe
    210                 215                 220

Val Cys Asn Asp Trp His Thr Gly Pro Leu Ser Cys Tyr Leu Lys Ser
225                 230                 235                 240

Asn Tyr Gln Ser His Gly Ile Tyr Arg Asp Ala Lys Thr Ala Phe Cys
                245                 250                 255

Ile His Asn Ile Ser Tyr Gln Gly Arg Phe Ala Phe Ser Asp Tyr Pro
            260                 265                 270

Glu Leu Asn Leu Pro Glu Arg Phe Lys Ser Ser Phe Asp Phe Ile Asp
            275                 280                 285

Gly Tyr Glu Lys Pro Val Glu Gly Arg Lys Ile Asn Trp Met Lys Ala
    290                 295                 300

Gly Ile Leu Glu Ala Asp Arg Val Leu Thr Val Ser Pro Tyr Tyr Ala
305                 310                 315                 320

Glu Glu Leu Ile Ser Gly Ile Ala Arg Gly Cys Glu Leu Asp Asn Ile
                325                 330                 335

Met Arg Leu Thr Gly Ile Thr Gly Ile Val Asn Gly Met Asp Val Ser
            340                 345                 350

Glu Trp Asp Pro Ser Arg Asp Lys Tyr Ile Ala Val Lys Tyr Asp Val
            355                 360                 365

Ser Thr Ala Val Glu Ala Lys Ala Leu Asn Lys Glu Ala Leu Gln Ala
    370                 375                 380

Glu Val Gly Leu Pro Val Asp Arg Asn Ile Pro Leu Val Ala Phe Ile
385                 390                 395                 400

Gly Arg Leu Glu Glu Gln Lys Gly Pro Asp Val Met Ala Ala Ala Ile
                405                 410                 415

Pro Gln Leu Met Glu Met Val Glu Asp Val Gln Ile Val Leu Leu Gly
            420                 425                 430

Thr Gly Lys Lys Lys Phe Glu Arg Met Leu Met Ser Ala Glu Glu Lys
            435                 440                 445

Phe Pro Gly Lys Val Arg Ala Val Val Lys Phe Asn Ala Ala Leu Ala
    450                 455                 460

His His Ile Met Ala Gly Ala Asp Val Leu Ala Val Thr Ser Arg Phe
465                 470                 475                 480

Glu Pro Cys Gly Leu Ile Gln Leu Gln Gly Met Arg Tyr Gly Thr Pro
                485                 490                 495

Cys Ala Cys Ala Ser Thr Gly Gly Leu Val Asp Thr Ile Ile Glu Gly
            500                 505                 510
```

-continued

```
Lys Thr Gly Phe His Met Gly Arg Leu Ser Val Asp Cys Asn Val Val
        515                 520                 525

Glu Pro Ala Asp Val Lys Lys Val Ala Thr Thr Leu Gln Arg Ala Ile
        530                 535                 540

Lys Val Val Gly Thr Pro Ala Tyr Glu Glu Met Val Arg Asn Cys Met
545                 550                 555                 560

Ile Gln Asp Leu Ser Trp Lys Gly Pro Ala Lys Asn Trp Glu Asn Val
                565                 570                 575

Leu Leu Ser Leu Gly Val Ala Gly Gly Glu Pro Gly Val Glu Gly Glu
                580                 585                 590

Glu Ile Ala Pro Leu Ala Lys Glu Asn Val Ala Ala Pro
        595                 600                 605
```

GENETICALLY MODIFIED PLANTS WHICH SYNTHESIZE A LOW AMYLOSE STARCH WITH INCREASED SWELLING POWER

CROSS-REFERENCE TO RELATED APPLICATIONS

This application is the U.S. National Stage filing of International Application No. PCT/EP2008/000614, filed Jan. 23, 2008, which claims priority to European Patent Application No. EP 070 90 009.7, filed Jan. 26, 2007, and U.S. Provisional Application No. 60/898,427, filed Jan. 30, 2007, the disclosures of which are hereby incorporated in their entirety by reference.

The present invention relates to genetically modified monocotyledonous plant cells and plants whose starch has an apparent amylose content of less than 5% by weight and an increased activity of a protein with the activity of a starch synthase II and an increased activity of a protein with the activity of a glucan, water dikinase. Such plants synthesize starch with an increased hot-water swelling power. Methods and processes for the generation/preparation of these plant cells, plants, starches and flours are likewise subject matter of the present invention.

Besides oils, fats and proteins, polysaccharides are the most important renewable resources from plants. Starch, which is one of the most important reserve materials in Higher Plants, plays a central role in the polysaccharides, besides cellulose.

Furthermore, starch is a nutritionally essential component of human and animal food. The structural features of the starch which is present in foodstuffs may have an effect on the functional properties (for example water-binding capacity, swelling power), the nutritional characteristics (for example digestibility, effect of the foodstuff on the glycemic index) or the structural characteristics (for example sliceability, texture, stickiness, processability) of a very wide range of foodstuffs. Food products therefore frequently comprise a starch with specific structural features which bring about the desired characteristics of the foodstuff in question. Also, the starch which is present in the plant tissues may affect the characteristics of foodstuffs which comprise starch-storing plant tissues (for example grains, fruits, flours).

The polysaccharide starch is a polymer made up of chemically uniform units, the glucose molecules. However, it constitutes a highly complex mixture of different forms of molecules which differ with regard to their degree of polymerization, the occurrence of branches of the glucose chains and their chain lengths and which, moreover, may be modified, for example phosphorylated. Starch therefore does not constitute a uniform raw material. In particular, one differentiates between amylose and amylopectin. In typical plants used for industrial starch production or as foodstuffs such as, for example, maize, rice, wheat or potato, amylose accounts for approximately 20%-25% and amylopectin for approximately 70%-80% of the synthesized starch.

The functional, nutritional or structure-imparting characteristics of starch such as, for example, solubility, the retrogradation behavior, the water-binding capacity, the film-forming properties, the viscosity, the gelatination properties, the freeze-thaw stability, the stability to acid, the gel strength, the swelling power, the digestibility, the size of the starch grains of starches are affected, inter alia, by the structural features of the starch, such as the amylose/amylopectin ratio, the molecular weight of the glucose polymers, the side-chain distribution pattern, the ion content, the lipid and protein content and/or the starch grain morphology.

Methods based on plant breeding may be used to modify selected structural characteristics of the starch and therefore functional, nutritional or structure-imparting characteristics of starch in plant cells. However, at present this is only possible for selected structural features of starch (for example amylopectin/amylose content, U.S. Pat. No. 5,300,145). It is not possible currently for example to influence the starch phosphate content in plants by plant breeding methods alone.

An alternative to plant breeding methods is the targeted modification of starch-producing plants by means of recombinant methods. However, a prerequisite for doing so is the identification and characterization of the enzymes involved in starch synthesis and/or starch modification, and their subsequent functional analysis in transgenic plants.

A variety of enzymes which characterize different reactions are involved in the synthesis of starch in plant cells. Starch synthases (EC2.4.1.21, ADP-glucose:1,4-alpha-D-glucan 4-alpha-D-glucosyltransferase) catalyze a polymerization reaction by transferring a glucosyl residue from ADP-glucose to alpha-1,4-glucans, where the glucosyl residue transferred is linked with the alpha-1,4-glucan by generating an alpha-1,4-linkage. Several isoforms of starch synthases have been identified in each of the plants studied to date. Two classes of starch synthases can be distinguished: the granule-bound starch synthases (GBSS) and the soluble starch synthases (in the context of the present invention also abbreviated to "SS"). Granule-bound starch synthases catalyze the synthesis of amylose, while soluble starch synthases are involved in the synthesis of amylopectin (Ball and Morell, 2003, Annu. Rev, Plant Biol. 54, 207-233; Teltow et al., 2004, J. Expt. Bot. 55(406), 2131-2145). The group of the soluble starch synthases has several isoforms which are referred to the specialist literature as SSI, SSII, SSIII, SSIV and SSV. The association of starch synthases to the individual isoforms (SSI, SSII, SSIII, SSIV, SSV) is made with the sequence homologies of the respective protein sequences of the enzymes in question (Ball and Morell, 2003, Annu. Rev, Plant Biol. 54, 207-233). Each individual isoform of the soluble starch synthases has, in accordance with current teaching, allocated to it a specific function in the synthesis of starch. While only one isoform of SSI proteins has been detected in dicotyledonous plants, two different classes of SSII proteins have been detected in some monocotyledonous plants (for example maize), which are referred to as SSIIa and SSIIb, respectively. In monocotyledonous plants, SSIIa is expressed preferentially in the endosperm, and SSIIb preferentially in the leaf tissue (Teltow et al., 2004, J. Expt. Bot. 55(406): 2131-2145). The specific function, in particular of the individual soluble starch synthases, in the synthesis of the starch is currently not fully explained (Ball and Morell, 2003, Annu. Rev, Plant Biol. 54: 207-233).

The functional, nutritional or structure-parting characteristics of starch are also affected by the phosphate content, a noncarbon component. Here, one has to distinguish between phosphate which is bonded covalently to starch glucose molecules in the form of monoesters (referred to as starch phosphate in the context of the present invention) and phosphate in the form of starch-associated phospholipids.

The starch phosphate content varies with the plant cultivar. Thus, for example, certain maize mutants synthesize a starch with an increased starch phosphate content (waxy maize at 0.002% and high-amylose maize at 0.013%), while traditional maize varieties only contain traces of starch phosphate. Likewise, small amounts of starch phosphate are found in wheat (0.001%), while no starch phosphate was detected in oats and *Sorghum*. In waxy rice mutants, less starch phosphate (0.003%) was found than in traditional rice varieties (0.013%). Significant amounts of starch phosphate were detected in plants which synthesize tuber or root storage starch, such as, for example, tapioca (0.008%), sweet potato (0.011%), arrow root (0.021%) or potato (0.089%). The above-cited percentages for the starch phosphate content refer in each case to the dry weight of the starch and have been determined by Jane et al. (1996, Cereal Foods World 41 (11): 827-832).

Starch phosphate may be present in the form of monoesters at the C2, C3 or C6 position of the polymerized glucose monomers (Takeda and Hizukuri, 1971, Starch/Stärke 23: 267-272). The phosphate distribution of the phosphate in starch synthesized by plants is generally distinguished by the fact that approximately 30% to 40% of the phosphate residues are bonded covalently in the C3 position and approximately 60% to 70% of the phosphate residues in the C6 position of the glucose molecules (Blennow et al., 2000, Int. J. of Biological Macromolecules 27: 211-218). Blennow et al. (2000, Carbohydrate Polymers 41: 163-174) determined a starch phosphate content which is bonded in the C6 position of the glucose molecules for a variety of starches such as, for example, potato starch (between 7.8 and 33.5 nmol per mg starch, depending on variety), starch from various *Curcuma* species (between 1.8 and 63 nmol per mg starch), tapioca starch (2.5 nmol per mg starch), rice starch (1.0 nmol per mg starch), mungbean starch (3.5 nmol per mg starch) and sorghum starch (0.9 nmol per mg starch). These authors did not detect any starch phosphate bonded in the C6 position in barley starch and starch from various waxy mutants of maize. No relationship between the genotype of a plant and the starch phosphate content has been established as yet (Jane et al., 1996, Cereal Foods World 41 (11): 827-832).

To date there have been described two proteins which mediate the introduction of covalent bonds of phosphate residues to starch's glucose molecules. The first protein has the enzymatic activity of an alpha-glucan, water dikinase (GWD, E.C.: 2.7.9.4) (Ritte et al., 2002, PNAS 99: 7166-7171), is frequently referred to as R1 in particular in the earlier scientific literature and is bound to the starch granules of storage starch in potato tubers (Lorberth et al., 1998, Nature Biotechnology 16: 473-477). The second protein described in the literature which catalyzes the introduction of starch phosphate into starch has the enzymatic activity of a phosphorglucan, water dikinase (PWD, E.C.: 2.7.9.5) (Kötting et al., 2005, Plant Physiol. 137: 2424-252, Baunsgaard et al., 2005, Plant Journal 41: 595-605).

One essential difference between GWD and PWD is that GWD is capable of utilizing unphosphorylated starch as its substrate, i.e. a de novo phosphorylation of unphosphorylated starch can be catalyzed by GWD, while PWD requires already phosphorylated starch as its substrate, i.e. introduces additional phosphate into already-phosphorylated starch (Kötting et al., 2005, Plant Physiol. 137: 2424-252, Baunsgaard et al., 2005, Plant Journal 41: 595-605). A further essential difference between GWD and PWD is that GWD introduces phosphate groups exclusively in the C6 position of the starch's glucose molecules, while PWD exclusively phosphorylates the C3 position of starch's glucose molecules (Ritte et al., 2006, FEBS Letters 580: 4872-4876).

In the reaction which is catalyzed by GWD, or PWD, the starting materials alpha-1,4-glucan (in the case of GWD) and phosphorylated alpha-1,4-glucan (in the case of PWD), respectively, adenosin triphosphate (ATP) and water are converted into the products glucan phosphate (starch phosphate), inorganic phosphate and adenosin monophosphate (Kötting et al., 2005, Plant Physiol. 137: 2424-252; Ritte et al., 2002, PNAS 99: 7166-7171).

Wheat plants which have an elevated activity of GWD proteins as the result of the expression of a GWD-encoding gene from potato are described in WO 02/34923. In comparison with corresponding wild-type plants in which no starch phosphate could be detected, these plants synthesize starch with significant amounts of starch phosphate in the C6 position of the glucose molecules.

WO 05/002359 describes the expression, in maize plants, of a potato GWD which has been optimized for the codon usage in maize plants. By means of $^{31}$P NMR, a total phosphate content of 0.0736% phosphate based on the amount of glucose (bonded at the C6, C3 and C2 position of the glucose molecules) of the maize starch in question was determined. If a molecular weight 98 is assumed for phosphate ($H_3PO_4$), a total phosphate content of approximately 7.5 nmol of phosphate per mg of starch results for the total phosphate content of 0.0736%—which has been determined in WO 05/002359—for starch isolated from transgenic maize plants. Plants which as the result of the expression of a PWD-encoding gene from *Arabidopsis thaliana* show an increased activity of a PWD protein are described in WO 05/095617. In comparison to corresponding untransformed wild type plants, these plants have an increased starch phosphate content.

An important functional characteristic, for example when processing starches in the food industry, is the swelling power. Various structural characteristics of starches, such as the amylose-/amylopectin ratio, the side chain length, the molecular weight distribution of the starch polymers, the number of branches and the amount of starch phosphate have an effect on functional characteristics, in particular on the swelling power of the starches in question (Narayana and Moorthy, 2002, Starch/Stärke 54: 559-592).

Amylose has long been regarded as a linear polymer consisting of α-1,4-glycosidically linked α-D-glucose monomers. However, more recent studies have demonstrated the presence of α-1,6-glycosidic branch points (approx. 0.1%) (Hizukuri and Takagi, 1984, Carbohydr. Res. 134: 1-10; Takeda et al., 1984, Carbohydr. Res. 132: 83-92).

Amylopectin constitutes a complex mixture of glucose chains with different branching patterns. In contrast to amylose, amylopectin comprises more branches. Side chains are linked via α-1,6-glycosidic linkages to the main chain of α-D-Glucose monomers, which are α-1,4-glycosidically linked. According to the literature (Voet and Voet, 1990. Biochemistry, John Wiley & Sons), the α-1,6-branches occur on average every 24 to 30 glucose residues. This corresponds to a degree of branching of approx. 3%-4%. The data on the degree of branching vary and depend on the origin of the starch in question (for example plant species, plant variety and the like). In typical plants used for the industrial production of starch, such as, for example, maize, wheat or potato, amylose starch accounts for approximately 20%-30% and amylopectin starch for approximately 70%-80% of the starch synthesized.

Another important difference between amylose and amylopectin is their molecular weight. While amylose, depending on the origin of the starch, has a molecular weight of $5 \times 10^5$-$10^6$ Da, the molecular weight of amylopectin is between $10^7$ and $10^8$ Da. The two macromolecules can be distinguished on the basis of their molecular weight and their different physical-chemical characteristics, and the simplest way of visualizing this is through their different iodine-binding characteristics.

A large number of technical applications only require amylopectin since amylopectin has a thickening action. Amylose has a gelling action and is therefore rather undesired for a number of uses. Pure amylopectin starch makes possible a very uniform surface structure combined with high viscosity, stability and transparency. Possible applications for these starches are in papermaking, in the adhesives industry, the textiles industry, the building industry and the cosmetics industry. Furthermore, amylopectin starch is the preferred starting material for the preparation of maltodextrins as the result of their increased solubility in water, stability to dissolution and transparency in comparison with maltodextrins which are prepared from amylose-comprising starches.

In the food industry, amylopectin starches are frequently employed as stabilizers, binders and for improving texture. Amylopectin starches are particularly advantageous in the case of those processing steps at which large temperature variations occur during processing and finishing (for example freeze-thaw-stability). The use of amylopectin starches in the food industry is growing, in particular taking into consideration the increasing demand for (semi-)finished products.

GBSSI ("granule-bound starch synthase I") is involved in amylose formation. To date, plants have been described in which the activity of the granule-bound starch synthase GBSSI is reduced (Shure et al., 1983, Cell 35: 225-233; Hovenkamp-Hermelink et al., 1987, Theoretical and Applied Genetics 75: 217-221; Visser et al., 1991, Mol. Gen. Genet. 225: 289-296; Hergersberg, 1988, Thesis, University of Cologne; WO 92/11376). Furthermore, there are known mutants which lack a functional GBSSI gene and which therefore synthesize an amylose-free (=amylopectin) starch (Kossmann and Lloyd 2000, Critical Reviews in Plant Sciences, 19(3): 171-226). The endosperm of corresponding GBSSI mutant of maize is waxy in appearance, which is why the term "waxy" endosperm has been introduced as a synonym for amylose-free starches.

When describing the swelling power of starch, one must distinguish between swelling power in cold water (for example room temperature) and swelling power in warm or hot water. The swelling power of native starches in cold water is negligible, if not nonexistent, while physically modified (pregellatized, dried) starches are capable of swelling even in cold water. Preparation methods for cold water swelling starches are described for example in U.S. Pat. No. 4,280,851. In the context of the present invention, the term "swelling power" refers to the behavior of starch in warm/hot aqueous suspensions. The swelling power is routinely determined by warming starch granules in the presence of an excess of water, removing unbound water after centrifugation of the suspension and forming the quotient from the weight of the residue obtained and that of the amount of starch weighed in. When carrying out this procedure, warming the starch suspension causes crystalline regions of the starch granules to dissolve and the water molecules to intercalate into the starch granules without dissolving the structure of the starch granule itself, i.e. only a swelling of the individual starch granules takes place.

In comparison with starches from cereals, starches isolated from tubers or tuber-like tissues have a considerably higher hot-water swelling power.

For potato starches isolated from various varieties, a maximum swelling power of 74.15 g/g (variety Kufri Jyoti) at 85° C. has been determined (Singh et al., 2002, Journal of the Science of Food and Agriculture 82: 1376-1383), using the method of Leach et al. (1959, Cereal Chemistry 36: 534-544). Takizawa et al. (2004, Brazilian Archives of Biology and Technology 47(6): 921-931) determined a swelling power of 100 g/g for potato starch (90° C., using the method of Leach et al., above). Wheat starch isolated from various cultivars has a swelling power of 16.6 g/g to 26.0 g/g (temperature: boiling aqueous 0.1% $AgNO_3$ suspension) (Yamamori and Quynh, 2000, Theor Appl Genet. 100: 23-38). Starch isolated from various cultivars of hull-less barley has a swelling power of 16.5 g/g or 19.3 g/g, and waxy, or amylose-free starch of various cultivars of said barley has a swelling power of 36.0 g/g to 55.7 g/g (temperature: 70° C., aqueous 0.1% $AgNO_3$, Yasui et al., 2002, Starch/Stärke 54: 179-184). For maize starch, a swelling power of 22.3 g/g has been determined, and for high-amylose maize starches a swelling power of 9.6 g/g (Hylon V), 6.1 g/g (Hylon VII) or 3.9 g/g (LAPS=Low AmyloPectin Starch) (90° C., Shi et al., 1998, J. Cereal Sci. 27: 289-299). U.S. Pat. No. 6,299,907 states a swelling power of 35.4 g/g for waxy maize starch. For starch isolated from various rice cultivars, a swelling power of 26.0 g/g to 33.2 g/g has been determined (Sodhi and Singh, 2003, Food Chemistry 80: 99-108), using the method of Leach et al. (above). Chen et al. (2003, Starch/Stärke 55: 203-212) determined a swelling power of approximately 25 g/g to approximately 49 g/g (95° C., aqueous suspension) for various mixtures of waxy rice starches with high-amylose rice starches. Yasui et al. (2002, Starch/Stärke 54: 179-184) determined a swelling power of 55.7 g/g (measured in boiling water in 0.1% aqueous silver nitrate solution) for an amylase-free rice starch.

By producing derivatives of native starches, it is possible to modify functional characteristics of the starches. Crosslinked wheat starches have a swelling power of from 6.8 g/g to 8.9 g/g, depending on the degree of crosslinking, acetylated wheat starches have a swelling power of a maximum of 10.3 g/g, and simultaneously crosslinked and acetylated wheat starches have a swelling power of 9.4 g/g, while the corresponding non-derivatized starches have a swelling power of 8.8 g/g (measured at 90° C.; Van Hung und Morita, 2005, Starch/Stärke 57: 413-420).

For acetylated waxy rice starches, a swelling power of approximately 30 g/g has been determined and for crosslinked waxy rice starch a swelling power of approximately 15 g/g, while corresponding non-derivatized waxy rice starch had a swelling power of approximately 41 g/g. Acetylated rice starch had a swelling power of approximately 20 g/g and crosslinked rice starch a swelling power of approximately 13 g/g, while corresponding non-derivatized rice starch had a swelling power of approximately 14 g/g (measured at 90° C., Liu et al., 1999, Starch/Stärke 52: 249-252). U.S. Pat. No. 6,299,907 describes crosslinked starches, where the crosslinking reaction had been carried out after preswelling the starches in question in a sodium hydroxide/sulfate solution. Depending on the degree of crosslinking, wheat starch was found to have a swelling power of from 6.8 g/g to 7.3 g/g (corresponding non-derivatized wheat starch 14.7 g/g), wheat hydroxypropyl starch a swelling power of 9.7 g/g (corresponding non-derivatized wheat starch 22.9 g/g), crosslinked maize starch a swelling power of 5.9 g/g (corresponding non-derivatized maize starch 16.7 g/g), crosslinked waxy maize starch a swelling power of 8.3 g/g (corresponding non-derivatized waxy maize starch 35.4 g/g), and crosslinked potato starch a swelling power of 6.7 g/g (corresponding non-derivatized potato starch was not specified in detail) (measurements at 95° C.). This reveals that the swelling power of starch cannot be increased substantially, if at all, by current derivatization methods.

The object of the present invention is to provide modified waxy starches with altered functional characteristics, and novel plant cells and plants which synthesize a waxy starch with altered functional characteristics, as well as methods and means for generating said plants and/or plant cells.

In particular, the altered functional characteristics consist in the fact that the modified starches have an increased hotwater swelling power.

Thus, the present invention relates to genetically modified monocotyledonous plant cells or genetically modified monocotyledonous plants whose starch has an apparent amylose content of less than 5% by weight, and which additionally have an increased activity of a protein with the enzymatic activity of a starch synthase II and additionally an increased activity of a protein with the enzymatic activity of a glucan, water dikinase in comparison with corresponding genetically not modified wild-type plant cells, or corresponding genetically not modified wild-type plants.

In this context, the genetic modification may be any genetic modification which leads to the synthesis of a starch with less than 5% by weight amylose and simultaneously to an increase in the activity of at least one protein with the activity of a starch synthase II and (simultaneously) of at least one protein with the activity of a glucan, water dikinase in genetically modified plant cells or genetically modified plants in comparison with corresponding not genetically modified wild-type plant cells or wild-type plants.

In the context of the present invention, the term "wild-type plant cell" means plant cells which act as starting material for the generation of the plant cells according to the invention, i.e. whose genetic information, with the exception of the introduced genetic modification, corresponds to that of a plant cell according to the invention.

In the context of the present invention, the term "wild-type plant" means plants which acted as starting material for the generation of the plants according to the invention, i.e. whose genetic information, with the exception of the introduced genetic modification, corresponds to that of a plant according to the invention.

In the context of the present invention, the term "corresponding" means that, when comparing several objects, the objects in question which are compared with one another are maintained under identical conditions. In the context of the present invention, the term "corresponding" in the context of wild-type plant cell or wild-type plant means that the plant cells or plants which are compared with one another were grown under identical culture conditions and have an identical (culture) age.

The term "monocotyledonous plants" refers to the monocots. Botanically, they belong to one of the three classes of the angiosperms (Magnoliophyta). In contrast to dicots, monocotyledonous plants are distinguished by the fact that the embryo typically has only one cotyledon primordium (Greek: monos="single" and kotyledon="cotyledon"). Moreover, they have sheathed vascular bundles, i.e. phloem and xylem are not separated by a meristem, which is why no secondary thickening of the stem is possible. This class of plants includes, inter alia, the grasses with the orders Cyperales and Poales, and a large number of other families.

In the context of the present invention, the term "increased activity of at least one protein with the (enzymatic) activity of a starch synthase II" means an increase in the expression of endogenous genes which code for proteins with the activity of a starch synthase II and/or an increase in the amount of proteins with the activity of a starch synthase II in the cells and/or an increase in the activity of proteins with the activity of a starch synthase II in the cells.

In the context of the present invention, the term "increased activity of a protein with the (enzymatic) activity of a glucan, water dikinase" means an increase in the expression of endogenous genes which code for proteins with the activity of a glucan, water dikinase and/or an increase in the amount of proteins with the activity of a glucan, water dikinase in the cells and/or an increase in the activity of proteins with the activity of a glucan, water dikinase in the cells.

The increase in expression can be determined, for example, by measuring the amount of transcripts which code for proteins with the activity of a starch synthase II or proteins with the activity of a glucan, water dikinase. This can be done for example by northern blot analysis or by Q-PCR (quantitative transcription polymerase chain reaction).

An increase in the amount of a protein with the activity of a glucan, water dikinase means, in this context, preferably an increase in the amount of the protein in question by at least 50%, in particular by at least 70%, preferably by at least 85% and especially preferably by at least 100% in comparison to corresponding, not genetically modified cells.

An increase in the amount of protein with the activity of a glucan, water dikinase also means that plants or plant cells which contain no detectable amount of proteins with the activity of a glucan, water dikinase will, following genetic modification according to the invention, contain a detectable amount of protein with the activity of a glucan, water dikinase.

Methods for raising antibodies which specifically react to a certain protein, i.e. which specifically bind to said protein, are known to the skilled worker (see, for example, Lottspeich and Zorbas (Eds.), 1998, Bioanalytik, Spektrum akad, Verlag, Heidelberg, Berlin, ISBN 3-8274-0041-4). The raising of such antibodies can be commissioned from some companies (for example Eurogentec, Belgian). Antibodies by means of which an increase in the amount of protein with the activity of a glucan, water dikinase can be determined by means of immunological methods are described by Lorberth et al. (1998, Nature Biotechnology 16: 473-477) and Rifte et al. (2000, Plant journal 21: 387-391). Antibodies by means of which an increase in the amount of protein with the activity of a starch synthase II can be determined by means of immunological methods are described by Walter ("Untersuchungen der Expression und Funktion der Starkesynthase II (SSII) aus Weizen (*Triticum aestivum*) [Studies into the expression and function of starch synthase II (SSII) from wheat (*Triticum aestivum*)]", PhD Thesis at the Faculty of Biology, University of Hamburg, ISBN 3-8265-8212-8).

The amount of the activity of a protein with the activity of a glucan, water dikinase can be detected for example as described in the literature (Mikkelsen et al., 2004, Biochemical Journal 377: 525-532; Ritte et al., 2002, PNAS 99: 7166-7171).

The amount of the activity of a protein with the activity of a starch synthase II can be determined for example as described in the literature (Nishi et al., 2001, Plant Physiology 127: 459-472). A preferred method for determining the amount of the activity of a protein with the activity of a starch synthase II is described under "General Methods".

Preferably, plant cells according to the invention or plants according to the invention have an activity of a protein with the activity of a starch synthase II which is increased by at least a factor of 2, preferably by at least a factor of 6, in comparison with corresponding genetically not modified wild-type plant cells, or wild-type plants.

The construction of proteins with the activity of a starch synthase II (ADP-glucose:1,4-alpha-D-glucan 4-alpha-D-glucosyltransferase; EC 2.4.1.21) shows a sequence of certain domains. At the N terminus, they have a signal peptide for the transport into plastids. From the N terminus toward the C terminus, there follow an N-terminal region and a catalytic domain (Li et al., 2003, Funct Integr Genomics 3, 76-85). Further analyses based on amino acid sequence alignments (http://hits.isb-sib.ch/cgi-bin/PFSCAN) of various proteins with the activity of a starch synthase II revealed that these proteins have three specific domains. In the amino acid sequence shown as SEQ ID NO 4, the amino acids 322 to 351 represent domain 1, the amino acids 423 to 462 domain 2 and the amino acids 641 to 705 the domain 3. Domain 1 is encoded by the nucleotides 1190 to 1279, domain 2 by the nucleotides 1493 to 1612 and domain 3 by the nucleotides 2147 to 2350 of the nucleic acid sequence shown as SEQ ID NO 3.

In the context of the present invention, the term "protein with the activity of a starch synthase II" is understood as meaning a protein which catalyzes a glucosylation reaction in which glucose residues of the substrate ADP-glucose are transferred to alpha-1,4-linked glucan chains, with formation of an alpha-1,4-linkage (ADP-Glucose+{(1,4)-alpha-D-glucosyl}(N)<=>ADP+{(1,4)-alpha-D-glucosyl}(N+1)), where the amino acid sequence of the protein with the activity of a protein of a starch synthase II has at least 86%, preferably at least 93%, particularly preferably at least 95%, especially preferably at least 98% identity with the amino acids 322 to 351 (domain 1) of the amino acid sequence shown as SEQ ID NO 4, and at least 83%, preferably at least 86%, particularly preferably at least 95%, especially preferably at least 98% identity with the amino acids 423 to 462 (domain 2) of the amino acid sequence shown as SEQ ID NO 4 and at least 70%, preferably at least 82%, preferably 86%, particularly preferably 95%, especially preferably at least 98% identity with the amino acids 641 to 705 (domain 3) of the amino acid sequence shown as SEQ ID NO 4. Nucleic acid sequences and the corresponding amino acid sequences which have said identity with domains 1, 2 and 3 and which code for a protein with the activity of a starch synthase II are known to the skilled worker and published for example as Accession No AY133249 (*Hordeum vulgare*), Accession No AY133248 (*Aegilops tauschii*), Accession Nos XP467757, AAK64284 (*Oryza sativa*), Accession No AAK81729 (*Oryza sativa*) Accession Nos AAD13341, AAS77569, No AAD13342 (*Zea mays*), Accession No AAF13168 (*Manihut esculenta*), Accession No BAD18846 (*Phaseolus vulgaris*), Accession No CAA61241 (*Solanum tuberosum*), Accession No CAA61269 (*Pisum sativum*), Accession No AAC19119 (*Ipomea batatas*), Accession No AAF 26156 (*Arabidopsis thaliana*), Accession No AAP41030 (*Colocasia esculenta*), Accession No AAS88880 (*Ostraeococcus tauri*) or Accession No AAC17970 (*Chlamydomonas reinhardii*). The abovementioned nucleic acid sequences and amino acid sequences coding for a protein with the activity of a starch synthase II are accessible via NCBI (http://www.ncbi.nlm.nih.gov/entrez/) and are expressly incorporated into the description of the present application by reference.

For the purposes of the present invention, the term "protein with the activity of a glucan, water dikinase" is understood as meaning a protein which transfers a beta-phosphate residue from ATP to starch. Starches isolated from leaves of an *Arabidopsis thaliana* sex1-3 mutant contain no detectable amounts of covalently bonded phosphate residues, but are phosphorylated in vitro by a protein with the activity of a glucan, water dikinase. This means that unphosphorylated starch, for example isolated from leaves of an *Arabidopsis thaliana* sex1-3 mutant is used as the substrate in a phosphorylation reaction which is catalyzed by a protein with the activity of a glucan, water dikinase.

A protein with the activity of a glucan, water dikinase transfers the beta-phosphate residue of ATP to starch in the C6 position of glucose, and the gamma-phosphate residue of ATP to water. Another reaction product which is generated is AMP (adenosin monophosphate). A protein with the activity of a glucan, water dikinase is therefore also referred to as [alpha-1,4-glucan], water dikinase, or else starch: water dikinase (E.C.: 2.7.9.4; Ritte et al., 2002, PNAS 99: 7166-7171).

The phosphorylation of starch which is catalyzed by a protein with the activity of a glucan, water dikinase gives rise to additional phosphate monoester bonds exclusively in the C6 position of the glucose molecules (Ritte et al., 2006, FEBS Letters 580: 4872-4876). The catalysis of the phosphorylation reaction of a starch by a protein with the activity of a glucan, water dikinase gives rise to an intermediate phosphorylated protein in which the beta-phosphate residue of ATP is bonded covalently to an amino acid of the protein with the activity of a glucan, water dikinase (Ritte et al., 2002, PNAS 99, 7166-7171). The intermediate is formed by autophosphorylation of the protein with the activity of a glucan, water dikinase, i.e. the protein with the activity of a glucan, water dikinase itself catalyzes the reaction which leads to the intermediate. Amino acid sequences which code for proteins with the activity of a glucan, water dikinase contain a phosphohistidine domain. Phosphohistidine domains are described for example by Tien-Shin Yu et al. (2001, Plant Cell 13, 1907-1918). In the autophosphorylation of a protein with the activity of a glucan, water dikinase, a histidine residue in the phosphohistidine domain of the amino acid sequence, coding for a protein with the activity of a glucan water dikinase, is phosphorylated (Mikkelsen et al., 2004, Biochemical Journal 377: 525-532). In the protein sequence, shown for example as SEQ ID NO 2, of a protein with the activity of a glucan, water dikinase from *Solanum tuberosum*, the amino acids 1064 to 1075 constitute the phosphohistidine domain. If another amino acid is substituted for the conserved histidine residue (amino acid 1069 in the protein sequence shown for example as SEQ ID NO 2) of the phosphohistidine domain, autophosphorylation, and thus phosphorylation, of glucans by the mutagenized protein no longer takes place (Mikkelsen et al., 2004, Biochemical Journal 377: 525-532). Furthermore, a protein with the activity of a glucan, water dikinase is distinguished by the fact that it has a C-terminal nucleotide binding domain which is comprised by the amino acids 1121 to 1464 in the amino acids sequence shown for example as SEQ ID NO 2. A deletion of the nucleotide binding domain leads to inactivation of a protein with the activity of a glucan, water dikinase (Mikkelsen und Blennow, 2005, Biochemical Journal 385, 355-361). Proteins with the activity of a glucan, water dikinase have on their N terminals a carbohydrate binding domain (CBM) which is comprised by the amino acids 78 to 362 in the amino acid sequence shown as SEQ ID NO 2. Carbohydrate binding domains are distinguished inter alia by the fact that their amino acid sequences contain conserved tryptophan residues. If other amino acids are substituted for these conserved amino acid residues, the carbohydrate binding domains lose their ability of binding glucans. Thus, for example, a substitution of amino acids W139 or W194 in the amino acid sequence shown as SEQ ID NO 2 leads to a loss of function of this carbohydrate binding domain. If, however, the carbohydrate binding domain of a glucan, water dikinase is deleted (for example a deletion of amino acids 1 to 362, where the amino acids 1 to 77 in the amino acid sequence shown as SEQ ID NO 2 constitute a plastidal signal peptide), this does not lead to the inactivation of the phosphorylating activity of the enzyme (Mikkelsen et al., 2006, Biochemistry 45: 4674-4682).

Nucleic acid sequences and their corresponding amino acid sequences coding for a protein with the activity of a glucan, water dikinase are described from different species such as, for example, potato (WO 97/11188, GenBank Acc.:

AY027522, Y09533), wheat (WO 00/77229, U.S. Pat. No. 6,462,256, GenBank Acc.: AAN93923, GenBank Acc.: AR236165), rice (GenBank Acc.: AAR61445, GenBank Acc.: AR400814), maize (GenBank Acc.: AAR61444, GenBank Acc.: AR400813), Soybean (GenBank Acc.: AAR61446, GenBank Acc.: AR400815; citrus (GenBank Acc.: AY094062), *Arabidopsis* (GenBank Acc.: AF312027) and the green algae *Ostreococcus tauri* (GenBank Acc.: AY570720.1). The abovementioned nucleic acid sequences and amino acid sequences coding for a protein with the activity of a glucan, water dikinase are published inter alia by the NCBI (http://www.ncbi.nlm.nih.gov/entrez/) and are expressly incorporated into the description of the present application by reference.

In the context of the present invention, the term "GBSS I" is to be understood to mean any enzyme which belongs to the group of the granule-bound starch synthase of isoform I (EC 2.4.1.21).

In the context of the present invention, the term "GBSSI-Gen" is understood as meaning a nucleic acid molecule or polynucleotide (cDNA, DNA) which codes for a granule-bound starch synthase I (GBSS I). Seq ID No 7-12 comprise nucleic acid sequences or amino acid sequences which code in each case for a protein with the activity of a GBSS I from rice, wheat and maize.

Polynucleotides coding for GBSS I are described for a variety of monocotyledonous plant species such as, for example, for maize (Genbank Acc. Nos. AF079260, AF079261), wheat (Genbank Acc. Nos. AB019622, AB019623, AB019624), rice (Genbank Acc. Nos. AF092443, AF092444, AF031162), barley (Genbank Acc. Nos. X07931, X07932), *Sorghum bicolor* (Genbank Acc. No U23945) and durum wheat (Genbank Acc. No AB029063). The abovementioned nucleic acid sequences and amino acid sequences coding for a protein with the activity of a GBSS I are published inter alia by NCBI (http://www.ncbi.nlm.nih.gov/entrez/) and are expressly incorporated into the description of the present application by reference.

Mutants which lack a functional GBSS I gene synthesize an amylose-free starch (=waxy starch). Such mutants are described for a series of crops such as, for example, for maize (for example by Sprague et al, 1943, J. Am. Soc. Agron. 35:817-822; Shure et al. 1983, Cell 35: 225-233), rice (Sano 1984, Theor. Appl. Genet. 68: 467-473; Villareal and Juliano 1986, Starch/Staerke 38:118-119), barley (Rohde et al 1988, Nucleic Acids Res 16: 7185-7186), wheat (Nakamura et al 1995, Mol. Gen. Genet. 248: 253-259), potato (Hovenkamp-Hermelink et al. 1987, Theor. Appl. Genet. 75: 217-221) and millet (Okuno and Sakaguchi 1982, J. Hered 73: 467). The term "waxy mutant" is used synonymously, owing to the fact that, in maize, the endosperm has a waxy appearance. The GBSS I protein is also frequently referred to as "waxy protein" (Kossmann and Lloyd 2000 "Understanding and Influencing Starch Biochemistry", Critical Reviews in Plant Sciences, 19(3): 171-226).

Suitable plant cells or plants for the generation of the plant cells and plants according to the invention are those which show a reduction of the apparent amylose content in the starch synthesized by them to less than 5% by weight.

In one embodiment of the present invention, a genetic modification of the plant cells according to the invention or of the plants according to the invention is brought about by mutagenesis of one or more GBSS I genes. The nature of the mutation is of no consequence as long as it brings about a reduction, or complete diminishment, of the GBSSI activity, and thus a reduction of the apparent amylose content of the starch present in the plants according to the invention to less than 5% by weight.

A mutation which leads to the reduction of the GBSSI activity and to the diminishment of the apparent amylose content of the starch to less than 5% by weight in the plant cells and plants according to the invention may occur spontaneously, and the plants in question can be selected and propagated with the aid of the methods described hereinbelow.

For the purposes of the present invention, a "waxy mutant" is understood as meaning a plant whose starch has an apparent amylose content of less than 5% by weight. Equally, "waxy starch" refers to a starch with an apparent amylose content of less than 5% by weight.

In the context of the present invention, the term "mutagenesis" is understood as meaning any type of introduced mutation such as, for example, deletions, point mutations (nucleotide substitutions), insertions, inversions, gene conversions or chromosomal translocations.

Agents which can be employed for generating chemically induced mutations, and the types of mutation obtained thereby as the result of the effect of the mutagens in question are described, for example, by Ehrenberg and Husain (1981, Mutation Research 86: 1-113) and Müller (1972, Biologisches Zentralblatt 91 (1): 31-48). The generation of rice mutants using gamma rays, ethylmethanesulfonate (EMS), N-methyl-N-nitrosourea or sodium azide ($NaN_3$) is described for example, by Jauhar and Siddiq (1999, Indian Journal of Genetics, 59 (1): 23-28), Rao (1977, Cytologica 42: 443-450), Gupta and Sharma (1990, Oryza 27: 217-219) and Satoh and Omura (1981, Japanese Journal of Breeding 31 (3): 316-326). The generation of wheat mutants using $NaN_3$ or maleic anhydrazide is described by Arora et al. (1992, Annals of Biology 8 (1): 65-69). An review of the generation of wheat mutants using various types of high-energy radiation and chemical agents is described by Scarascia-Mugnozza et al. (1993, Mutation Breeding Review 10:1-28). Svec et al. (1998, Cereal Research Communications 26 (4): 391-396) describe the use of N-ethyl-N-nitrosourea for the generation of mutants in triticale. The use of MMS (methylmethanesulfonic acid) and gamma radiation for the generation of millet mutants is described by Shashidhara et al. (1990, Journal of Maharashtra Agricultural Universities 15 (1): 20-23).

Monocotyledonous plant cells and plants which synthesize a starch with an apparent amylose content of less than 5% by weight (=waxy plants, or waxy plant cells) can also be generated by using what is known as insertion mutagenesis (review: Thorneycroft et al., 2001, Journal of Experimental Botany 52 (361): 1593-1601). "Insertion mutagenesis" is understood as meaning in particular the insertion of transposons, or what is known as transfer DNA (T-DNA) into a gene.

The transposons may take the form of transposons which occur naturally in a (wild-type) plant cell (endogenous transposons) or else those which do not occur naturally in said cell but have been introduced into the cell by means of recombinant methods, such as, for example, by transforming the cell (heterologous transposons). Modifying the expression of genes by means of transposons is known to the skilled worker. A review of the utilization of endogenous and heterologous transposons as tools in plant biotechnology can be found in Ramachandran and Sundaresan (2001, Plant Physiology and Biochemistry 39, 234-252). The possibility of identifying mutants in which specific genes have been inactivated by transposon insertion mutagenesis can be found in a review by Maes et al. (1999, Trends in Plant Science 4 (3), 90-96). The generation of rice mutants with the aid of endogenous transposons is described by Hirochika (2001, Current Opinion in Plant Biology 4, 118-122). The identification of maize genes with the aid of endogenous retrotransposons is shown, for example, in Hanley et al. (2000, The Plant Journal 22 (4), 557-566). The possibility of generating mutants with the aid of retrotransposons and methods for identifying mutants are described by Kumar and Hirochika (2001, Trends in Plant Science 6 (3), 127-134). The activity of heterologous transposons in different species has been described both for dicotyledonous and for monocotyledonous plants, for example for rice (Greco et al., 2001, Plant Physiology 125, 1175-1177; Liu et al., 1999, Molecular and General Genetics 262, 413-420; Hiroyuki et al., 1999, The Plant Journal 19 (5), 605-613; Jeon and Gynheung, 2001, Plant Science 161, 211-219), barley (Koprek et al., 2000, The Plant Journal 24 (2), 253-263), *Arabidopsis thaliana* (Aarts et al., 1993, Nature 363, 715-717, Schmidt and Willmitzer, 1989, Molecular and General Genetics 220, 17-24; Altmann et al., 1992, Theoretical and Applied Genetics 84, 371-383; Tissier et al., 1999, The Plant Cell 11, 1841-1852), tomato (Belzile and Yoder, 1992, The Plant Journal 2 (2), 173-179) and potato (Frey et al., 1989, Molecular and General Genetics 217, 172-177; Knapp et al., 1988, Molecular and General Genetics 213, 285-290).

In principle, monocotyledonous "waxy" plant cells and plants can be generated, with the aid of both homologous and heterologous transposons, the use of homologous transposons also including those transposons which are already naturally present in the plant genome. In principle, T-DNA mutagenesis is likewise suitable for producing "waxy" plant cells and plants.

T-DNA insertion mutagenesis is based on the fact that certain segments (T-DNA) of Ti plasmids from *Agrobacterium* are capable of integrating into the genome of plant cells. The site of integration into the plant chromosome is not fixed but may take place at any position. If the T-DNA integrates in a segment of the chromosome which constitutes a gene function, this may lead to a modification of the gene expression and thus also to an altered activity of a protein encoded by the gene in question. In particular, the integration of a T-DNA into the coding region of a gene frequently means that the protein in question can no longer be synthesized in active form, or not at all, by the cell in question. The use of T-DNA insertions for the generation of mutants is described, for example, for *Arabidopsis thaliana* (Krysan et al., 1999, The Plant Cell 11, 2283-2290; Atipiroz-Leehan and Feldmann, 1997, Trends in Genetics 13 (4), 152-156; Parinov and Sundaresan, 2000, Current Opinion in Biotechnology 11, 157-161) and rice (Jeon and An, 2001, Plant Science 161, 211-219; Jeon et al., 2000, The Plant Journal 22 (6), 561-570). Methods for identifying mutants which have been generated with the aid of T-DNA insertion mutagenesis are described, inter alia, by Young et al., (2001, Plant Physiology 125, 513-518), Parinov et al. (1999, The Plant cell 11, 2263-2270), Thorneycroft et al. (2001, Journal of Experimental Botany 52, 1593-1601), and McKinney et al. (1995, The Plant Journal 8 (4), 613-622).

Mutations in the corresponding gene can be found with the aid of methods with which the skilled worker is familiar. For example, it is possible to employ molecular analyzes based on hybridizations with probes ("Southern blot"), on the amplification by means of polymerized chain reaction (PCR), on the sequencing of suitable genomic nucleic acid fragments and the search for individual nucleotides substitutions. An example of a method of identifying mutations with the aid of hybridization patterns is the search for restriction fragment length polymorphisms (RFLP) (Nam et al., 1989, The Plant Cell 1: 699-705; Leister and Dean, 1993, The Plant Journal 4 (4): 745-750). A PCR based method is, for example, the analysis of amplified fragment length polymorphisms (AFLP) (Castiglioni et al., 1998, Genetics 149: 2039-2056; Meksem et al., 2001, Molecular Genetics and Genomics 265: 207-214; Meyer et al. 1998, Molecular and General Genetics 259: 150-160). The use of amplified fragments which have been cleaved with restriction endonucleases ("cleaved amplified polymorphic sequences", CAPS) is a further possibility of identifying mutations (Konieczny and Ausubel, 1993, The Plant Journal 4: 403-410; Jarvis et al., 1994, Plant Mol. Biol. 24: 685-687; Bachem et al., 1996, The Plant Journal 9 (5): 745-753). Methods of determining SNPs have been described by, inter alia, Qi et al. (2001, Nucleic Acids Research 29 (22): 116), Drenkard et al. (2000, Plant Physiology 124: 1483-1492) and Cho et al. (1999, Nature Genetics 23: 203-207). Particularly suitable methods are those which permit a large number of plants to be studied for mutations in certain genes within a short period of time. Such a method, known as TILLING ("targeting induced local lesions in genomes") has been described by McCallum et al. (2000, Plant Physiology 123: 439-442).

The skilled worker knows that the above-described mutations are, as a rule, recessive mutations. To manifest the waxy phenotype, it is therefore necessary to generate true-breeding (homozygous) plant cells or plants. Methods of generating true-breeding plants are known to the skilled worker.

Homozygous "waxy" mutants can be identified by staining the starch with iodine. To this end, starch-comprising tissue samples (for example endosperm, pollen) are stained with iodine solution and studied for example under the microscope. Waxy starches stain brown (in comparison with the blue staining of the wild type).

In a further embodiment of the present invention, the introduction of one or more foreign nucleic acid molecules/polynucleotides, their presence and/or the expression of one or more foreign nucleic acid molecules/polynucleotides lead to the inhibition of the expression of endogenous genes which code for the GBSS I protein and to a reduction of the apparent amylose content of the starch present in the plant cell according to the invention, or plant according to the invention, to less than 5% by weight.

This can be done by various methods with which the skilled worker is familiar. These methods include, for example, the expression of a suitable antisense RNA, or of a double-stranded RNA, the provision of molecules or vectors which confer a cosuppression effect, the expression of a suitably constructed ribozyme which specifically cleaves transcripts which code for GBSSI, or what is known as "in-vivo mutagenesis". Furthermore, the reduction of the GBSSI activity/activities and/or the reduction of the gene expression of the GBSSI gene in the plant cells can also be brought about by the simultaneous expression of sense and antisense RNA molecules of the specific target gene to be repressed, preferably the GBSSI gene. These methods are known to the skilled worker.

In addition, it is known that the formation of double-stranded RNA of promoter sequences in trans can bring about methylation and transcriptional inactivation of homologous copies of this promoter in planta (Mette et al., 2000, EMBO J. 19: 5194-5201).

To inhibit the gene expression by means of antisense or cosuppression technology, for example, it is possible to employ a DNA molecule which comprises all of the GBSSI coding sequence including any flanking sequences present, or else DNA molecules which only comprise parts of the coding sequence, where these parts must be long enough to bring about an antisense effect, or cosuppression effect, in the cells. Generally suitable are sequences with a minimum length of 15 bp, preferably with a minimum length of 20-30 bp, especially preferably with a length of 100-500 bp, and, for highly efficient antisense or cosuppression inhibition, in particular sequences with a length of more than 500 bp.

Also suitable for antisense or cosuppression approaches is the use of polynucleotide sequences with a high degree of identity with the endogenous sequences which are present in the plant cell and which encode GBSSI. The minimum identity should be greater than approximately 65%. The use of sequences with identities of at least 90%, in particular between 95% and 100%, is to be preferred.

To achieve an antisense effect, or a cosuppression effect, it is furthermore also feasible to use introns, i.e. from noncoding regions of genes which code for GBSSI.

The use of intron sequences for inhibiting the expression of genes which code for starch biosynthesis proteins has been described in WO 97/04112, WO 97/04113, WO 98/37213, WO 98/37214.

The skilled worker knows how to achieve an antisense effect and a cosuppression effect. The method of cosuppression inhibition has been described, for example, by Jorgensen (1990, Trends Biotechnol. 8: 340-344), Niebel et al. (1995, Top. Microbiol. Immunol. 197: 91-103), Flavell et al. (1995, Curr. Top. Microbiol. Immunol. 197: 43-46), Palauqui and Vaucheret (1995, Plant Mol. Biol. 29: 149-159), Vaucheret et al. (1995, Mol. Gen. Genet. 248: 311-317), de Borne et al. (1994, Mol. Gen. Genet. 243: 613-621).

Furthermore, a reduction of the GBSSI activity in the plant cells can also be brought about by the simultaneous expression of sense and antisense RNA molecule of the specific target gene to be repressed, preferably the GBSSI gene.

This can be achieved for example by using chimeric constructs which comprise "inverted repeats" of the target gene in question, or parts of the target gene. The chimeric constructs code for sense and antisense RNA molecules of the target gene in question. Sense and antisense RNA are synthesized simultaneously in planta as one RNA molecule, it being possible for sense and antisense RNA to be separated from each other by a spacer, to form a double-stranded RNA molecule (RNAi technology).

It has been demonstrated that the introduction of inverted-repeat DNA constructs into the genome of plants is a highly effective method for repressing the genes corresponding to the inverted-repeat DNA constructs (Waterhouse et al., 1998, Proc. Natl. Acad. Sci. USA 95, 13959-13964; Wang and Waterhouse, 2000, Plant Mol. Biol. 43, 67-82; Singh et al., 2000, Biochemical Society Transactions 28 (6), 925-927; Liu et al., 2000, Biochemical Society Transactions 28 (6), 927-929; Smith et al., 2000, Nature 407, 319-320; WO 99/53050). Sense and antisense sequences of the target gene, or target genes, may also be expressed separately from one another by means of identical or different promoters (Nap et al, 6$^{th}$ International Congress of Plant Molecular Biology, 18-24 Jun. 2000, Quebec, Poster S7-27, Lecture Session S7).

The expression of ribozymes for reducing the activity of specific enzymes in cells is also known to the skilled worker and described, for example, in EP-B1 0321201. The expression of ribozymes in plant cells has been described for example by Feyter et al. (1996, Mol. Gen. Genet. 250: 329-338).

Moreover, the reduction of the GBSSI activity and/or the reduction of the apparent amylose content of the starch present in the plant cells to less than 5% by weight may also be achieved by what is known as "in-vivo" mutagenesis, where an RNA-DNA oligonucleotide hybrid ("chimeroplast") is introduced into cells by means of transforming cells (Kipp et al., Poster Session at the 5$^{th}$ International Congress of Plant Molecular Biology, 21-27 Sep. 1997, Singapore; R. A. Dixon and C. J. Arntzen, Meeting report regarding Metabolic Engineering in Transgenic Plants, Keystone Symposia, Copper Mountain, Colo., USA, 1997, TIBTECH 15: 441-447; WO 95/15972; Kren et al., 1997, Hepatology 25: 1462-1468; Cole-Strauss et al., 1996, Science 273: 1386-1389; Beetham et al., 1999, PNAS 96: 8774-8778).

Part of the DNA component of the RNA-DNA oligonucleotide is homologous with a polynucleotide sequence of an endogenous GBSSI gene, but comprises a mutation in comparison with the polynucleotide acid sequence of an endogenous GBSSI gene or comprises a heterologous region which is surrounded by the homologous regions. Owing to base pairing of the homologous regions of the RNA-DNA oligonucleotide and of the endogenous polynucleotide, followed by homologous recombination, the mutation or heterologous region present in the DNA component of the RNA-DNA oligonucleotide can be transferred into the genome of a plant cell.

Thus, the reduction of the GBSSI activity in the plant cells can also be achieved by generating double-stranded RNA molecules of GBSSI genes. To this end, it is preferred to introduce, into the genome of plants, inverted repeats of DNA molecules which are derived from nucleotide sequences formed by GBSSI genes or cDNAs formed by such genes, where the DNA molecules to be transcribed are under the control of a promoter which governs the expression of said RNA molecules.

A further possibility of reducing the activity of proteins in plant cells or plants is the method of what is known as immunomodulation. It is known that an expression in planta of antibodies which specifically recognize a plant protein results in a reduction of the activity of said proteins in corresponding plant cells or plants as the result of the formation of a protein/antibody complex (Conrad and Manteufel, 2001, Trends in Plant Science 6: 399-402; De Jaeger et al., 2000, Plant Molecular Biology 43: 419-428; Jobling et al., 2003, Nature Biotechnology 21: 77-80).

All the abovementioned methods are based on the introduction of one or more foreign nucleic acid molecules into the genome of plant cells or plants and are therefore suitable in principle for the generation of plant cells according to the invention and plants according to the invention.

The reduction of the expression can be determined for example by measuring the amount of transcripts which code for the enzymes in question, for example by means of Northern blot analysis or quantitative RT-PCR.

The reduction of the amount of GBSSI protein can be determined for example by immunological methods such as Western blot analysis, ELISA ("enzyme linked immuno sorbent assay") or RIA ("radio immune assay").

A reduction in the GBSSI activity in the plant cells, or plants, according to the invention can also be detected indirectly via quantifying of the reaction product of the GBSSI protein, amylose. The skilled worker knows a multiplicity of methods for determining the amylose content in plant starches. For cereals, in particular rice, the apparent amylose content is preferably determined by a method similar to that of Juliano (1971, Cereal Science Today 16 (10): 334-340), as described further below in the chapter "Materials and Methods".

In a further embodiment for generating the plant cells according to the invention or the plants according to the invention, it is possible to use, instead of a wild-type plant cell or wild-type plant, a mutant which is distinguished by the fact that it already synthesizes a starch with an apparent amylose content of less than 5% by weight and/or which has an increased activity of a protein with the activity of a glucan, water dikinase and/or an increased activity of a protein with the activity of a starch synthase II. These mutants may be either spontaneously occurring mutants or else those which have been generated by the targeted use of mutagens. Possibilities of generating such mutants have been described hereinabove.

The present invention furthermore comprises a genetically modified monocotyledonous plant cell, or plant, according to the invention whose genetic modification consists in the introduction of at least one foreign nucleic acid molecule into the genome of the plant used for the transformation.

As the result of the introduction of a foreign nucleic acid molecule, the genetic information of the plant cells according to the invention or plants according to the invention are altered. The presence of at least one foreign nucleic acid molecule leads to an altered "phenotype". Here, "altered phenotype" means a measurable alteration of one or more cellular functions. For example, the genetically modified plant cells according to the invention and the genetically modified plants according to the invention show, as the result of the presence or, in the case of expression of introduced foreign nucleic acid molecules, an increase in the activity of a protein with the activity of a glucan, water dikinase and an increase in the activity of a protein with the activity of a starch synthase II and/or a reduction of the activity of a protein with the activity of a GBSSI.

In the context of the present invention, the term "foreign nucleic acid molecule" is understood as meaning a molecule which either does not occur naturally in the plant cells used for the transformation, or which does not occur naturally in the specific spatial arrangement in the plant cells used for the transformation, or which is located at a locus in the genome of the plant cell used for the transformation at which it does not occur naturally. The foreign nucleic acid molecule is preferably a recombinant molecule which consists of various elements whose combination or specific spatial arrangement does not occur naturally in plant cells. Thus, recombinant nucleic acid molecules may, for example, besides nucleic acid molecules which code for a protein with the activity of a glucan, water dikinase and/or a protein with the activity of a starch synthase II and/or a nucleic acid which brings about a reduction in the activity of a GBSSI, have additional nucleic acid sequences which are not naturally present in combination with the abovementioned nucleic acid molecules. The abovementioned additional nucleic acid sequences which are present on a recombinant nucleic acid molecule in combination with a nucleic acid molecule coding for protein with the activity of a glucan, water dikinase and/or protein with the activity of a starch synthase II and/or with a nucleic acid which is suitable for mediating a reduction in the activity of a protein with the activity of a GBSSI may be any sequences. They may be for example genomic and/or plant nucleic acid sequences. Preferably, these additional nucleic acid sequences are regulatory sequences (promoters, termination signals, enhancers), particularly preferably regulatory sequences which are active in plant tissue; especially preferably tissue-specific regulatory sequences.

Methods of generating recombinant nucleic acid molecules are known to the skilled worker and comprise genetic engineering methods such as, for example, the linking of nucleic acid molecules by ligation, genetic recombination or the de-novo synthesis of nucleic acid molecules (see, for example, Sambrok et al., Molecular Cloning, A Laboratory Manual, 3rd edition (2001) Cold Spring Harbour Laboratory Press, Cold Spring Harbour, N.Y., ISBN: 0879695773; Ausubel et al., Short Protocols in Molecular Biology, John Wiley & Sons; 5th edition (2002), ISBN: 0471250929).

In the context of the present invention, the term "genome" is understood as meaning the totality of the hereditary material present in a plant cell. The skilled worker knows that not only the nucleus, but other compartments too (for example plastids, mitochondria) comprise hereditary material.

In principle, a foreign nucleic acid molecule can be any nucleic acid molecule which brings about, in the plant cell or plant, an increase in the activity of a protein with the activity of a glucan, water dikinase and of a protein with the activity of a starch synthase II and a reduction in the activity of a protein with the activity of a GBSSI.

In a preferred embodiment, the foreign nucleic acid molecules coding for a protein with the activity of a glucan, water dikinase take the form of the already-mentioned nucleic acid molecules from the various plant species, which nucleic acid molecules are known to the skilled worker. Particularly preferred in this context are nucleic acid molecules coding for a protein with the activity of a glucan, water dikinase from potato, especially preferred is a protein with the activity of a glucan, water dikinase which has the amino acid sequence shown in SEQ ID NO 2 or is encoded by the nucleic acid sequence shown in SEQ ID NO 1.

In a further preferred embodiment, the foreign nucleic acid molecules coding for a protein with the activity of a starch synthase II take the form of the already-mentioned nucleic acid molecules from the various plant species, which nucleic acid molecules are known to the skilled worker. Particularly preferred in this context are nucleic acid molecules coding for a protein with the activity of a starch synthase II from wheat, especially preferred is a protein with the activity of a starch synthase II which has the amino acid sequence shown in SEQ ID NO 4 or is encoded by the nucleic acid sequence shown in SEQ ID NO 3.

A further preferred embodiment takes the form of nucleic acid molecules coding for a protein with the activity of a starch synthase II from rice, especially preferably a protein with the activity of a starch synthase II which has the amino acid sequence shown in SEQ ID NO 6 or is encoded by the nucleic acid sequence shown in SEQ ID NO 5.

In a further preferred embodiment, the foreign nucleic acid molecules coding for a protein with the activity of a GBSSI take the form of the already-mentioned nucleic acid molecules from the various plant species, which nucleic acid molecules are known to the skilled worker. Particularly preferred in this context are nucleic acid molecules coding for a protein with the activity of a GBSSI from rice, especially preferred is a protein with the activity of a GBSSI which has the amino acid sequence shown in SEQ ID NO 8 or is encoded by the nucleic acid sequence shown in SEQ ID NO 7.

A further preferred embodiment takes the form of nucleic acid molecules coding for a protein with the activity of a GBSSI from wheat, especially preferably a protein with the activity of a GBSSI which has the amino acid sequence shown in SEQ ID NO 10 or is encoded by the nucleic acid sequence shown in SEQ ID NO 9.

A further preferred embodiment takes the form of nucleic acid molecules coding for a protein with the activity of the GBSSI from maize, especially preferably a protein with the activity of a GBSSI which has the amino acid sequence shown in SEQ ID NO 12 or is encoded by the nucleic acid sequence shown in SEQ ID NO 11.

In a further embodiment, the plant cells and plants according to the invention are homozygous for the waxy mutation(s) and thus synthesize a starch whose apparent amylose content is less than 5% by weight.

In the context of the present invention, the term "homozygous for the waxy mutation(s)" is understood as meaning that the plant breeds true for the non-functional GBSSI genes. To the skilled worker, homozygosis means that, within the hereditary material of a cell, all alleles regarding a particular trait are identical, that is to say two or more identical copies of a certain gene are present on the two chromatids of a chromosome, which chromatids comprise the gene. They are homozygous (=breed true) for this gene and, when selfed, pass on the trait in question to all progeny. The skilled worker knows that polyploid plants such as, for example, wheat may, under certain circumstances, require three non-functional GBSSI alleles (on the subgenomes A, B and D) in homozygous form in order to manifest the waxy phenotype.

The foreign nucleic acid molecules introduced, for the purposes of genetic modification, into the plant cells or plant which manifest the waxy phenotype may take the form of a single nucleic acid molecule or more nucleic acid molecules. They may take the form of nucleic acid molecules which comprise nucleic acid sequences which code for a protein with the activity of a glucan, water dikinase and nucleic acid sequences which code for a protein with the activity of a starch synthase II, but also nucleic acid molecules in which the nucleic acid sequences which code for a protein with the activity of a glucan, water dikinase and the nucleic acid sequences which code for a protein with the activity of a starch synthase II are present on different nucleic acid molecules. For example, the nucleic acid sequences which code for a protein with the activity of a glucan, water dikinase and the nucleic acid sequences which code for a protein with the activity of a starch synthase II may be present simultaneously in a vector, plasmid or in linear nucleic acid molecules ("dual construct") or else be components of two vectors, plasmids or linear nucleic acid molecules which are separate in each case.

If the nucleic acid sequences which code for a protein with the activity of a glucan, water dikinase and the nucleic acid sequences which code for a protein with the activity of a starch synthase II are present in two separate nucleic acid molecules, they can be introduced into the genome of the plant cell or plant either simultaneously ("cotransformation") or else one after the other, i.e. with a chronological interval ("supertransformation"). The separate nucleic acid molecules may also be introduced into different individual plant cells or plants of a species. Thereby it is possible to generate plant cells or plants in which the activity of either at least one protein with the activity of a glucan, water dikinase or else at least one protein with the activity of a starch synthase II is elevated. Plants according to the invention can then be generated by subsequently hybridizing those plants in which the activity of a protein with the activity of a glucan, water dikinase is elevated with those in which the activity of a protein with the activity of a starch synthase II is elevated. The parameters for the selection of plants which are used for the process steps in question are defined further below.

In a further embodiment, the waxy phenotype of the plant cells or plants according to the invention is brought about by introducing one or more recombinant nucleic acid molecules suitable for reducing the GBSSI activity.

The foreign nucleic acid molecules introduced, for the purposes of genetic modification, into the wild-type plant cell or plant may take the form of a single nucleic acid molecule or more nucleic acid molecules. They may therefore take the form of nucleic acid molecules which comprise nucleic acid sequences which code for a protein with the activity of a glucan, water dikinase and the nucleic acid sequences which code for a protein with the activity of a starch synthase II and additionally to nucleic acid sequences which are suitable for inhibiting the activity of the GBSSI activity (triple construct). Equally, they may also take the form of nucleic acid molecules in which the nucleic acid sequences which code for a protein with the activity of a glucan, water dikinase and the nucleic acid sequences which code for a protein with the activity of a starch synthase II are present on different nucleic acid molecules, where one or the other of these two nucleic acid molecules additionally comprises nucleic acid sequences which are suitable for inhibiting the activity of the GBSSI activity. Alternatively, they may also take the form of nucleic acid molecules in which the nucleic acid sequences which code for a protein with the activity of a glucan, water dikinase and the nucleic acid sequences which code for a protein with the activity of a starch synthase II are present on one nucleic acid molecule and the nucleic acid molecules which are suitable for inhibiting the GBSSI activity are present on a different nucleic acid molecule (3 variants of one dual construct and one simple construct).

In a further embodiment, they may also take the form of three different nucleic acid molecules, where one comprises nucleic acid sequences which code for a glucan, water dikinase protein, another one comprises nucleic acid sequences coding for a starch synthase II and a further one comprises nucleic acid sequences which are suitable for inhibiting the GBSSI activity (3 simple constructs).

The nucleic acid molecules which are suitable for generating the plant cells or plants according to the invention may be present for example in a vector, plasmid or in linear nucleic acid molecules.

If the constructs to be used for the generation of plant cells or plants according to the invention are present in two or three separate nucleic acid molecules, they can be introduced into the genome of the plant cell or plant either simultaneously ("cotransformation") or else one after the other, i.e. with a chronological interval ("supertransformation"). The separate nucleic acid molecules may also be introduced into different individual plant cells or plants of a species. Thereby it is possible to generate plant cells or plants in which the activity of either at least one protein with the activity of a glucan, water dikinase and/or at least one protein with the activity of a starch synthase II is elevated and/or at least one protein with the activity of a GBSSI activity is reduced to such an extent that the starch synthetized by the plant cells or plants has apparent amylose content of less than 5% by weight. Plants according to the invention can then be generated by subsequently hybridizing the plants.

Furthermore, it is also possible to generate plants in which the activity of at least one protein with the (enzymatic) activity of a GBSSI is reduced to such an extent that the starch synthetized by the plant cells or plants has an apparent amylose content of less than 5% by weight and which, in a further step, by crossing with plants in which the activity of at least one protein with the activity of a starch synthase II is elevated, leads to plant cells or plants according to the invention.

In the event that one or more nucleic acid molecules which comprise nucleic acid sequences suitable for increasing the activity of at least one protein with the activity of a glucan, water dikinase and/or of a starch synthase II in the plant cells and reducing the activity of a GBSSI in the plant cells to such an extent that the starch synthetized by the cells has an apparent amylose content of less than 5%, are introduced into the genome of the plant cells in one methodological step/simultaneously, the plants according to the invention may be selected directly among the plants to which the transformation gives rise.

In a further embodiment, the plant cells according to the invention and the plants according to the invention comprise that at least one foreign nucleic acid molecule codes for a protein with the activity of a starch synthase II and a second foreign nucleic acid molecule codes for a protein with the activity of a glucan, water dikinase. In a further embodiment, the plant cells according to the invention of the plants according to the invention comprise that a first foreign nucleic acid molecule codes for a protein with the activity of a glucan, water dikinase and a second foreign nucleic acid molecule codes for a protein with the activity of a starch synthase II.

A multiplicity of techniques is available for introducing DNA into a plant host cell. These techniques comprise the transformation of plant cells with T-DNA using *Agrobacterium tumefaciens* or *Agrobacterium rhizogenes* as transformation agent, the fusion of protoplasts, the injection, the electroporation of DNA, the introduction of the DNA by means of the biolistic approach, and other possibilities.

The use of the agrobacteria-mediated transformation of plant cells has been studied intensively and has been described, inter alia, in EP 120516; Hoekema (In: The Binary Plant Vector System, Offsetdrukkerij Kanters B. V. Alblasserdam (1985), Chapter V); Fraley et al., Crit. Rev. Plant Sci. 4: 1-46) and by An et al. (1985, EMBO J. 4: 277-287).

The transformation of monocotyledonous plants by means of vectors based on *Agrobacterium* transformation has also been described (Chan et al. 1993, Plant Mol. Biol. 22: 491-506; Hiei et al., 1994, Plant J. 6, 271-282; Deng et al, 1990, Science in China 33: 28-34; Wilmink et al., 1992, Plant Cell Reports 11: 76-80; May et al., 1995, Bio/Technology 13: 486-492; Conner and Domisse, 1992, Int. J. Plant Sci. 153: 550-555; Ritchie et al, 1993, Transgenic Res. 2: 252-265). Alternative methods for the transformation of monocotyledonous plants are the transformation by means of the biolistic approach (Wan and Lemaux, 1994, Plant Physiol. 104: 37-48; Vasil et al., 1993, Bio/Technology 11: 1553-1558; Ritala et al., 1994, Plant Mol. Biol. 24: 317-325; Spencer et al., 1990, Theor. Appl. Genet. 79: 625-631), the transformation of protoplasts, the electroporation of partially permeabilized cells or the introduction of DNA by means of glass fibers. The transformation of maize, in particular, is described repeatedly in the literature (cf., for example, WO95/06128, EP0513849, EP0465875, EP0292435; Fromm et al., 1990, Biotechnology 8: 833-844; Gordon-Kamm et al., 1990, Plant Cell 2: 603-618; Koziel et al., 1993, Biotechnology 11: 194-200; Moroc et al., 1990, Theor. Appl. Genet. 80: 721-726).

This successful transformation of other cereal species has also been described, for example in the case of barley (Wan and Lemaux, s.o.; Ritala et al., s.o.; Krens et al., 1982, Nature 296: 72-74) and wheat (Nehra et al., 1994, Plant J. 5: 285-297; Becker et al., 1994, Plant Journal 5: 299-307). All the above methods are suitable within the scope of the present invention.

Plant cells and plants whose starch has an amylose content of less than 5% by weight and which are genetically modified as the result of the introduction of a gene coding for a protein with the activity of a glucan, water dikinase and/or a gene coding for a protein with the activity of a starch synthase II can be distinguished from wild-type plant cells, or wild-type plants, inter alia by the fact that they comprise at least one foreign nucleic acid molecule which does not occur naturally in wild-type plant cells, or wild-type plants, or by the fact that such a molecule is present at a location in the genome of the plant cell according to the invention or in the genome of the plant according to the invention at which it does not occur in wild-type plant cells, or wild-type plants, i.e. in a different genomic environment. Furthermore, such plant cells according to the invention or plants according to the invention can be distinguished from wild-type plant cells, or wild-type plants, by the fact that they comprise at least one copy of the foreign nucleic acid molecule stably integrated in their genome, if appropriate additionally to copies of such a molecule which are naturally present in the wild-type plant cells, or wild-type plants. If the foreign nucleic acid molecule(s) which has been introduced into the plant cells according to the invention or plants according to the invention takes the form of additional copies, besides molecules which naturally occur in the wild-type plant cells, or wild-type plants, the plant cells according to the invention and the plants according to the invention can be distinguished from wild-type plant cells, or wild-type plants, in particular by the fact that this additional copy, or these additional copies, is/are located at locations in the genome where it does not occur, or they do not occur, in wild-type plant cells or wild-type plants. This can be verified for example with the aid of a Southern blot analysis.

The plant cells according to the invention or the plants according to the invention can furthermore be preferably distinguished from wild-type plant cells, or wild-type plants, by at least one of the following features: if a foreign nucleic acid molecule which has been introduced is heterologous with regard to the plant cell or plant, then the plant cells according to the invention, or plants according to the invention, comprise transcripts of the nucleic acid molecules which have been introduced. These transcripts can be detected for example by Northern blot analysis or by RT-PCR (reverse transcription polymerase chain reaction).

Plant cells according to the invention or plants according to the invention which express an antisense transcript and/or an RNAi transcript can be detected for example with the aid of specific nucleic acid probes which are complementary to the RNA which codes for the protein (and which occurs naturally in the plant cell). Preferably, the plant cells according to the invention and the plants according to the invention comprise a protein which is encoded by a nucleic acid molecule which has been introduced. This protein can be detected for example by immunological methods, in particular by Western blot analysis.

Preferably, the plant cells according to the invention or the plants according to the invention comprise a protein which is encoded by a nucleic acid molecule which has been introduced. This protein can be detected for example by immunological methods, in particular by Western blot analysis.

If a foreign nucleic acid molecule which has been introduced is homologous with regard to the plant cell or plant, then the plant cells according to the invention, or the plants according to the invention, can be distinguished from wild-type plant cells, or wild-type plants, for example on the basis of the additional expression of the foreign nucleic acid molecules which have been introduced. The plant cells according to the invention and the plants according to the invention preferably comprise transcripts of the foreign nucleic acid molecules. This can be detected for example by Northern blot analysis or with the aid of what is known as quantitative PCR.

A further subject matter of the present invention relates to genetically modified monocotyledonous plant cells or genetically modified monocotyledonous plants which synthetize a modified starch in comparison with starch isolated from corresponding, not genetically modified wild-type plant cells, or isolated from corresponding not genetically modified wild-type plants.

The invention furthermore relates to genetically modified monocotyledonous plants which comprise plant cells according to the invention. Such plants can be generated from plant cells according to the invention by means of regeneration.

The plants according to the invention may, in principle, take the form of any monocotyledonous plants. Preferably, they take the form of monocotyledonous crop plants, i.e. plants which are grown by man for the purposes of nutrition or for technical, in particular industrial, purposes.

In a further embodiment, the plants according to the invention take the form of starch-storing monocotyledonous plants, or the plant cells according to the invention are derived from a starch-storing plant.

In the context of the present invention, the term "starch-storing plant" means all plants with plant parts which comprise a storage starch such as, for example, maize, rice, wheat, rye, oats, barley, sago, taro and millet/sorghum.

In a preferred embodiment, the present invention relates to monocotyledonous plants of the (systematic) family Poaceae. These plants particularly preferably take the form of rice, maize or wheat plants. These plants very particularly preferably take the form of rice plants.

In the context of the present invention, the term "wheat plants" means plant species of the genus *Triticum* or plants which have originated from crosses with plants of the genus *Triticum*, particularly plant species of the genus *Triticum* which are grown in agriculture for commercial purposes, or plants which have originated from crosses with plants of genus *Triticum*, with *Triticum aestivum* being especially preferred.

In the context of the present invention, the term "maize plants" means plant species of the genus *Zea*, particularly plant species of the genus *Zea*, which are grown in agriculture for commercial purposes, particularly preferably *Zea mays*.

In the context of the present invention, the term "rice plant" means plant species of the genus *Oryza*, particularly plant species of the genus *Oryza*, which are grown in agriculture for commercial purposes, particularly preferably *Oryza sativa*.

The present invention also relates to propagation material of monocotyledonous plants comprising genetically modified plant cells.

Here, the term "propagation material" comprises those parts of the plant which are suitable for generating progeny via the vegetative or sexual route. Examples which are suitable for vegetative propagation are cuttings, callus cultures, rhizomes or tubers. Other propagation material comprises for example fruits, seeds, seedlings, protoplasts, cell cultures and the like.

In a further embodiment, the present invention relates to plant parts capable of being harvested of plants according to the invention such as fruits, storage roots, roots, flowers, buds, shoots or stems, preferably seeds or kernels, these parts which are capable of being harvested comprising plant cells according to the invention.

In a further embodiment, the genetically modified monocotyledonous plant cells according to the invention are distinguished by the fact that they synthesize a (waxy) starch with elevated hot-water swelling power and an amylose content of less than 5% by weight.

In a preferred embodiment, the genetically modified monocotyledonous plant cell is distinguished by the fact that it comprises a waxy starch with an elevated hot-water swelling power of between 60 to 100 g/g.

Particularly preferred in this context is a hot-water swelling power of between 70 and 95 g/g, very particularly preferred of between 80 and 95 g/g and extraordinarily preferred of between 80 and 90 g/g.

A further subject matter of the present invention relates to a method of generating a genetically modified monocotyledonous plant, where a) a plant cell is genetically modified, the genetic modification comprising the following steps i to iii:
  i) introduction, into the plant cell, of a genetic modification, where the genetic modification leads to an increase in the activity of a protein with the activity of a starch synthase II in comparison with corresponding not genetically modified wild-type plant cells,
  ii) introduction, into the plant cell, of a genetic modification, where the genetic modification leads to an increase in the activity of a protein with the activity of a glucan, water dikinase in comparison with corresponding not genetically modified wild-type plant cells,
  iii) introduction, into the plant cell, of a genetic modification, where the genetic modification leads to a reduction in the activity of a protein with the activity of a GBSSI in comparison with corresponding not genetically modified wild-type plant cells, where steps i to iii can be carried out in any desired sequence, individually or simultaneously as any desired combination of steps i to iii, b) a plant is regenerated from plant cells of step a);
c) if appropriate, further plants are generated with the aid of the plants of step b), where, if appropriate, plant cells are isolated from plants in accordance with steps b) or c) and the method steps a) to c) are repeated until a plant has been generated which has an increased activity of a protein with the activity of a starch synthase II in comparison with corresponding not genetically modified wild-type plant cells and reduced activity of a protein with the activity of a glucan, water dikinase in comparison with corresponding not genetically modified wild-type plant cells and reduced activity of a protein with the activity of a GBSSI in comparison with corresponding not genetically modified wild-type plant cells.

The present invention furthermore also relates to a method of generating a genetically modified plant, in which a plant cell whose starch has an amylose content of less than 5% by weight is genetically modified, where genetic modification comprises the following steps a) and b) in any desired sequence, individually or simultaneously:

a) introduction, into the plant cell, of a genetic modification, where the genetic modification leads to an increase in the activity of a protein with the activity of a starch synthase II in comparison with corresponding not genetically modified wild-type plant cells,
b) introduction, into the plant cell, of a genetic modification, where the genetic modification leads to an increase in the activity of a protein with the activity of a glucan, water dikinase in comparison with corresponding not genetically modified wild-type plant cells, and
c) a plant is regenerated from plant cells of step a) and b);
d) if appropriate, further plants are generated with the aid of the plants from steps a) and b), where, if appropriate, plant cells are isolated from plants according to step a) or b) and the method steps a) to c) are repeated until a plant has been generated which comprises a foreign nucleic acid molecule coding for a protein with the activity of a starch synthase II and a foreign nucleic acid molecule coding for a protein with the activity of a glucan, water dikinase.

A preferred subject matter of the present invention relates to methods of generating a monocotyledonous plant, wherein a) a plant cell is genetically modified, where the genetic modification comprises the following steps i to iii in any desired sequence, or any desired combinations of the following steps i to iii are carried out individually or simultaneously
- i) introduction, into the plant cell, of a genetic modification, where the genetic modification leads to an increase in the activity of a protein with the activity of a starch synthase II in comparison with corresponding not genetically modified wild-type plant cells,
- ii) introduction, into the plant cell, of a genetic modification, where the genetic modification leads to an increase in the activity of a protein with the activity of a glucan, water dikinase in comparison with corresponding not genetically modified wild-type plant cells,
- iii) introduction, into the plant cell, of a genetic modification, where the genetic modification leads to a reduction in the activity of a protein with the activity of a GBSSI in comparison with corresponding not genetically modified wild-type plant cells, b) a plant is regenerated from plant cells comprising the genetic modification in accordance with steps
- i) a) i
- ii) a) ii
- iii) a) iii
- iv) a) i and a) ii,
- v) a) i and a) iii,
- vi) a) ii and a) iii, or
- vii) a) i and a) ii and a) iii c) there is introduced, into plant cells from plants in accordance with step
- i) b) i, a genetic modification in accordance with step a) ii,
- ii) b) i, a genetic modification in accordance with step a) iii,
- iii) b) i, a genetic modification in accordance with step a) ii and simultaneously a genetic modification in accordance with step a) iii,
- iv) b) ii, a genetic modification in accordance with step a) i,
- v) b) ii, a genetic modification in accordance with step a) iii,
- vi) b) ii, a genetic modification in accordance with step a) i and simultaneously a genetic modification in accordance with step a) iii,
- vii) b) iii, a genetic modification in accordance with step a) i,
- viii) b) iii, a genetic modification in accordance with step a) ii,
- ix) b) iii, a genetic modification in accordance with step a) i and simultaneously a genetic modification in accordance with step a) ii,
- x) b) iv, a genetic modification in accordance with step a) iii,
- xi) b) v, a genetic modification in accordance with step a) ii, or
- xii) b) vi, a genetic modification in accordance with step a) i and the plant is regenerated, d) there is introduced, into plant cells of plants in accordance with step
- i) c) i, a genetic modification in accordance with step a) iii,
- ii) c) ii, a genetic modification in accordance with step a) ii,
- iii) c) iv, a genetic modification in accordance with step a) iii,
- iv) c) v, a genetic modification in accordance with step a) ii,
- v) c) vii, a genetic modification in accordance with step a) ii,
- vi) c) vii, a genetic modification in accordance with step a) i, or
- vii) c) ix, a genetic modification in accordance with step a) ii and a plant is regenerated, if appropriate, further plants are generated with the aid of the plants in accordance with one of steps b) vii, c) iii, c) vi, c) x, c) xi, c) xii or in accordance with any of steps d) i to d) vii.

The genetic modifications introduced in accordance with step a) into the plant cell may, in principle, take the form of any type of modification which leads to an increase in the activity of a protein with the activity of a starch synthase II and/or which leads to the increase in the activity of a protein with the activity of a glucan, water dikinase and/or which leads to the reduction in the activity of a protein with the activity of a GBSSI.

The regeneration of the plants in accordance with steps b) to e) of the methods according to the invention can be accomplished by methods known to the skilled worker (for example described in "Plant Cell Culture Protocols", 1999, ed. by R. D. Hall, Humana Press, ISBN 0-89603-549-2).

The generation of further plants of the methods according to the invention can be accomplished for example by vegetative propagation (for example via cuttings, tubers or via callus culture and regeneration of intact plants) or by generative propagation. Generative propagation preferably takes place in a controlled manner, i.e. selected plants with specific properties are crossed with each other and propagated. The selection is preferably accomplished in such a way that the further plants (which are generated, depending on the method, in accordance with step c) or step d) or step e)) have the modifications introduced in the preceding steps.

The parameters for the selection of the plant cells or plants according to the invention which can be generated by crossing or by transformation are detailed hereinbelow: in the case where exclusively at least one protein with the activity of a glucan, water dikinase is increased, suitable plants or plant cells are those which have a phosphate content in the C6 position of the starch of at least 2.5 nmol per mg starch. In the case where exclusively at least one protein with the activity of a starch synthase II is increased, suitable plants or plant cells are those which have an SSII activity which is increased by at least a factor of 2 over the SSII activity in the plant cells or plants which are used for introducing the nucleic acid molecule(s) according to the invention or used for crossing.

In the case where at least one protein with the activity of a glucan, water dikinase and at least one protein with the activity of a starch synthase II are increased, suitable plants or plant cells are those which have a phosphate content in the C6 position of the starch of at least 2.5 nmol per mg starch and additionally an SSII activity which is increased by at least a factor of 2 over the SSII activity in the plant cells or plants which are used for introducing the nucleic acid molecule(s) according to the invention or used for crossing.

in the case where the GBSSI activity is reduced, or waxy mutants are employed, suitable plants are those which have an apparent amylose content of less than 5% by weight when the mutation is present in homozygous form.

Another suitable selection criterion is the level of the starch phosphate content in the C6 position. Plants which are preferably selected are those which comprise the genetic modification in accordance with step a) and b) and whose starch phosphate content is at least 2.5 nmol C6P/mg starch and whose starch has an apparent amylose content of less than 5% by weight.

In the method according to the invention for the generation of genetically modified plants, the genetic modifications for generating the genetically modified plant cells according to the invention can be effected simultaneously or in successive steps. In this context, it is not critical whether the same method is used for successive genetic modifications which lead to an increased activity of a protein with the activity of a starch synthase II as for the genetic modification which leads to an increased activity in a protein with the activity of a glucan, water dikinase and/or for the genetic modification which leads to a reduced activity of a protein with the activity of a GBSSI.

Various selection criteria may be chosen for selecting the plants according to the invention, or those plants which are used for further modifications.

In a further embodiment of the method according to the invention for the generation of a genetically modified plant, step c) is followed by a method step c)-1, in which plants are selected whose starch has an apparent amylose content of less than 5% by weight and an increased activity in a protein with the activity of a starch synthase II in accordance with step a)i) and/or has an increased activity of a protein with the activity of a glucan, water dikinase in accordance with step a)ii). The selected plants are then used for the further method steps.

In a further embodiment of the method according to the invention for the generation of a genetically modified plant according to the invention, at least one foreign nucleic acid molecule codes for a protein with the activity of a glucan, water dikinase from potato, wheat, rice, maize, soybean, citrus, Curcuma or Arabidopsis. Preferably, at least one foreign nucleic acid molecule codes for a protein with the activity of a glucan, water dikinase from potato and especially preferably for a protein which has the amino acid sequence shown in SEQ ID NO 2 or which is encoded by the nucleic acid sequence shown in SEQ ID NO 1. References for nucleic acid sequences coding for proteins with the activity of a glucan, water dikinase from the abovementioned plants have already been detailed further above.

In a further embodiment of the method according to the invention for generating a genetically modified plant according to the invention, at least one foreign nucleic acid molecule codes for a protein with the activity of a starch synthase II from wheat, barley, Aegilops, rice, maize, cassava, bean, potato, pea, sweet potato, Arabidopsis, taro, Ostreococcus or Chlamydomonas. Preferably, at least one foreign nucleic acid molecule codes for a protein with the activity of a starch synthase II from wheat, in particular Seq ID No 3. References for nucleic acid sequences coding for proteins with the activity of a starch synthase II from the abovementioned plants have already been detailed further above.

As already described above for foreign nucleic acid molecules introduced into a plant cell or plant for the purposes of genetic modification, the nucleic acid molecule(s) in step a) of the method according to the invention for the generation of a genetically modified plant whose starch has an amylose content of less than 5% by weight may take the form of a single nucleic acid molecule or a plurality of nucleic acid molecules. Thus, the foreign nucleic acid molecules coding for a protein with the activity of a starch synthase II, or coding for a protein with the activity of a glucan, water dikinase, may be present together on a single nucleic acid molecule or else they may be present in separate nucleic acid molecules. If the nucleic acid molecules coding for a protein with the activity of a starch synthase II and coding for a protein with the activity of a glucan, water dikinase are present in a plurality of nucleic acid molecules, these nucleic acid molecules may be introduced into a plant cell either simultaneously or in successive steps.

In a further embodiment of the method according to the invention for the generation of a genetically modified plant according to the invention, at least one foreign nucleic acid molecule codes for a protein with the activity of a GBSSI from a monocotyledonous plant, preferably from rice, wheat, barley, maize, Aegilops, sorghum or oats.

References for the abovementioned nucleic acid sequences coding for proteins with the activity of a GBSSI from the abovementioned plants have already been detailed further above.

Preferably, at least one foreign nucleic acid molecule codes for a protein with the activity of a GBSSI from rice and especially preferably for a protein which is encoded by the nucleic acid sequence shown in SEQ ID NO 7 or by the amino acid sequence shown in SEQ ID NO 8.

In a further preferred embodiment, at least one foreign nucleic acid molecule codes for a protein with the activity of a GBSSI from wheat and especially preferably for a protein which is encoded by the amino acid sequence shown in SEQ ID NO 9 or shown in SEQ ID NO 10.

In a further preferred embodiment, at least one foreign nucleic acid molecule codes for a protein with the activity of a GBSSI from maize and especially preferably for a protein which is encoded by the nucleic acid sequence shown in SEQ ID NO 11 or by the amino acid sequence shown in SEQ ID NO 12.

Here, the foreign nucleic acid molecule brings about the inhibition of the activity of a GBSS I and thus the synthesis of a starch with an amylose content of less than 5% by weight. What has been said above regarding the use of the nucleic acids in question for the generation of plant cells or plants according to the invention also applies here analogously.

The foreign nucleic acid molecule(s) used for the genetic modification may take the form of one combined or of a plurality of separate nucleic acid constructs, in particular of what are known as simple, dual or triple constructs. Thus, the foreign nucleic acid molecule may be what is known as a "triple construct", which is understood as meaning a single vector for the transformation of plants which comprises not only the genetic information for inhibiting the expression of an endogenous GBSSI gene, but also the information for the overexpression of one or more SSII genes and for the overexpression of one or more GWD genes.

A basic principle in the construction of the foreign nucleic acid molecules for inhibiting the GBSSI activity is the use of antisense, cosuppression, ribozyme and double-stranded RNA constructs and of sense constructs, which use leads to a reduction in the expression of endogenous genes which code for GBSSI and which leads to a simultaneous increase in the activity of the proteins with the activities of an SSII and/or of a GWD.

In this context, the foreign nucleic acid molecules may be introduced into the genome of the plant cell either simultaneously ("cotransformation") or else one after the other, i.e. in chronological succession ("supertransformation").

The foreign nucleic acid molecules may also be introduced into different individual plants of one species. In this way, it is possible to generate plants in which the activity of a protein with the activity of a GBSSI is reduced and/or the activity of a protein with the activity of an SSII or GWD is increased. Subsequently, crosses may then be made to generate plants in which the activity of a protein with the activity of a GBSSI is reduced and the activity of a protein with the activity of an SSII and a GWD is increased.

In the context of the present invention, the term "identity" is understood as meaning the number of amino acids/nucleotides which agree (identity) with other proteins/nucleic acids, expressed in percent.

Preferably, the identity regarding a protein with the activity of a starch synthase II is determined by comparing the amino acid sequences detailed under SEQ ID NO 4 or SEQ ID NO 6, or the identity regarding a nucleic acid molecule coding for a protein with the activity of a starch synthase II by comparing the nucleic acid sequences detailed under SEQ ID NO 3 or SEQ ID NO 5, and the identity regarding a protein with the activity of a glucan, water dikinase by comparing the amino acid sequence detailed in SEQ ID NO 2, or the identity regarding a nucleic acid molecule coding for a protein with the activity of a glucan, water dikinase by comparing the nucleic acid sequence detailed in SEQ ID NO 1, and the identity regarding a nucleic acid molecule coding for a protein with the activity of a GBSSI by comparing the nucleic acid sequences detailed in SEQ ID NO 7 or SEQ ID NO 9 or SEQ ID NO 11, or the amino acid sequences detailed in SEQ ID NO 8 or SEQ ID NO 10 or SEQ ID NO 12, with other proteins/nucleic acids with the aid of computer programs.

If sequences which are compared with each other are different in length, the identity is to be determined in such a way that the number of amino acids/nucleotides which the shorter sequence shares with the longer sequence determines the percentage identity. The identity is preferably determined by means of known computer programmes which are publicly available such as, for example, ClustalW (Thompson et al., Nucleic Acids Research 22 (1994), 4673-4680). ClustalW is made publicly available by Julie Thompson (Thompson@EMBL-Heidelberg.DE) and Toby Gibson (Gibson@EMBL-Heidelberg.DE), European Molecular Biology Laboratory, Meyerhofstrasse 1, D 69117 Heidelberg, Germany. ClustalW can likewise be downloaded from various internet pages, inter alia the IGBMC (Institut de Génétique et de Biologie Moléculaire et Cellulaire, B.P.163, 67404 Illkirch Cedex, France; ftp://ftp-igbmc.u-strasbg.fr/pub/) and the EBI (ftp://ftp.ebi.ac.uk/pub/software/) and all mirrored EBI internet pages (European Bioinformatics Institute, Wellcome Trust Genome Campus, Hinxton, Cambridge CB10 1SD, UK).

To determine the identity between proteins described within the scope of the present invention and other proteins, it is preferred to employ the ClustalW computer program version 1.8. The following parameters are to be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP.

To determine the identity between for example the nucleotide sequence of the nucleic acid molecules described within the scope of the present invention and the nucleotide sequence of other nucleic acid molecules, it is preferred to employ the ClustalW computer program version 1.8. The following parameters are to be set: KTUPLE=2, TOPDIAGS=4, PAIRGAP=5, DNAMATRIX:IUB, GAPOPEN=10, GAPEXT=5, MAXDIV=40, TRANSITIONS: unweighted.

Identity furthermore means that functional and/or structural equivalence exists between the nucleic acid molecules in question or the proteins encoded by them. The nucleic acid molecules which are homologous to the above-described molecules and which are derivatives of these molecules will, as a rule, take the form of variations to these molecules which are modifications with the same biological function. They may take the form of naturally occurring variations, for example sequences from other species or else of mutations, where it is possible that these mutations have occurred naturally or else have been introduced by specific mutagenesis. Furthermore, the variations may take the form of synthetically generated sequences. The allelic variants may take the form of naturally occurring variants or else of synthetically generated variants or variants which have been generated by recombinant DNA technology. A specific form of derivatives are for example nucleic acid molecules which deviate from the nucleic acid molecules described within the scope of the present invention as the result of the degeneracy of the genetic code.

Within the scope of the present invention, the term "hybridization" means hybridization under traditional hybridization conditions, preferably under stringent conditions as are described for example in Sambrook et al., (Molecular Cloning, A Laboratory Manual, 3rd edition (2001) Cold Spring Harbour Laboratory Press, Cold Spring Harbour, N.Y.; ISBN: 0879695773). Particularly preferably, "to hybridize" means hybridization under the following conditions:
Hybridization Buffer:
2×SSC; 10×Denhardt solution (Ficoll 400+PEG+BSA; ratio 1:1:1); 0.1% SDS; 5 mM
EDTA; 50 mM Na2HPO4; 250 µg/ml herring sperm DNA; 50 µg/ml tRNA; or
25 M sodium phosphate buffer pH 7.2; 1 mM EDTA; 7% SDS
Hybridization Temperature:
T=65 to 68° C.
Wash buffer: 0.1×SSC; 0.1% SDS
Wash temperature: T=65 to 68° C.

Nucleic acid molecules which hybridize with the abovementioned molecules can be isolated for example from genomic libraries or from cDNA libraries. The identification and isolation of such nucleic acid molecules may be accomplished using the abovementioned nucleic acid molecules or parts of these molecules, or using the reverse complements of these molecules, for example by means of hybridization by standard methods, or by amplification by means of PCR.

Hybridization probes which can be used for isolating a nucleic acid sequence coding for a protein with the activity of a starch synthase II or with the activity of a glucan, water dikinase or with the activity of a GBSSI are, for example, nucleic acid molecules with exactly the nucleotide sequences, or essentially the nucleotide sequences, detailed in SEQ ID NO 3 or SEQ ID NO 5 (starch synthase II) or in SEQ ID NO 1 (glucan, water dikinase) or in SEQ ID NO 7, 9 or 11 (GBSSI), or parts of these sequences.

The fragments used as hybridization probe may also take the form of synthetic fragments or oligonucleotides which have been generated with the aid of the customary synthetic techniques and whose sequence agrees essentially with that of a nucleic acid molecule described within the scope of the present invention. When genes which hybridize with the nucleic acid sequences described within the scope of the present invention have been identified and isolated, a determination of the sequence and an analysis of the characteristics of the proteins encoded by this sequence should be carried out to verify that they are proteins with the activity of a starch synthase II or the activity of a glucan, water dikinase or the activity of a GBSSI, respectively.

The molecules which hybridize with the nucleic acid molecules described within the scope of the present invention comprise in particular fragments, derivatives and allelic variants of the abovementioned nucleic acid molecules. In the context of the present invention, the term "derivative" means that the sequences of these molecules differ from the sequences of the above-described nucleic acid molecules at one or more positions and that they have a high degree of identity with these sequences. The deviations from the above-described nucleic acid molecules may have been generated for example by deletion, addition, substitution, insertion or recombination.

To express nucleic acid molecules according to the invention which code for a protein with the activity of starch synthase II and/or a protein with the activity of a glucan, water dikinase and/or a protein with the activity of a GBSSI, these molecules are preferably linked with regulatory DNA sequences which ensure transcription in plant cells. These include in particular promoters. In general, any promoter which is active in plant cells is suitable for expression.

The promoter may be selected in such a way that expression takes place constitutively or else only in a certain tissue, at a certain point in time of plant development or at a point in time determined by external factors. The promoter may be homologous or heterologous both with regard to the plant and with regard to the nucleic acid molecule.

Examples of suitable promoters are the 35S RNA promoter of the Cauliflower Mosaic Virus and the maize ubiquitin promoter, the rice ubiquitin promoter (Liu et al., Plant Science 165, (2003), the rice actin promoter (Zhang, et al., Plant Cell 3:1150-1160, 1991), the Cassava Vein Mosaic Virus (CVMV) promoter (Verdaguer et. al., Plant Mol. Biol. 31: 1129-1139), the maize histone $H_3C4$ promoter (U.S. Pat. No. 6,750,378) or the Cestrum YLCV promoter (Yellow Leaf Curling Virus; WO 01 73087; Stavolone et al., 2003, Plant Mol. Biol. 53, 703-713) for the purposes of constitutive expression. A promoter which ensures expression only in photosynthetically active tissues may also be used, for example the ST-LS1 promoter (Stockhaus et al., Proc. Natl. Acad. Sci. USA 1987, 84: 7943-7947; Stockhaus et al., EMBO J. 1989, 8: 2445-2451), or for endosperm-specific expression, the wheat HMW promoter, the *Vicia faba* USP promoter (Fiedler et al., 1993, Plant Mol. Biol. 22: 669-679; Baumlein et al., 1991, Mol. Gen. Genet. 225: 459-467), the bean phaseolin promoter, promoters of zein genes from maize (Pedersen et al., 1982, Cell 29: 1015-1026; Quatroccio et al., 1990, Plant Mol. Biol. 15: 81-93), a glutelin promoter (Leisy et al., 1990, Plant Mol. Biol. 14: 41-50; Zheng et al., 1993, Plant J. 4: 357-366; Yoshihara et al., 1996, FEBS Lett. 383: 213-218), a globulin promoter (Nakase et al., 1996, Gene 170(2): 223-226), a prolamin promoter (Qu and Takaiwa, 2004, Plant Biotechnology Journal 2(2): 113-125). However, it is also possible to use promoters which are activated only at a point in time which is determined by external factors (see, for example, WO 93/07279). Promoters which are also of interest may be promoters of heat-shock proteins, which can make simple induction possible. Furthermore, it is possible to use seed-specific promoters, such as, for example, the *Vicia faba* USP promoter (see above).

A termination sequence (polyandenylation signal) may also be present; this serves to add a poly-A tail to the transcript. The poly-A tail is assumed to have a function in the stabilization of the transcripts. Such elements are described in the literature (cf. Gielen et al., 1989, EMBO J. 8: 23-29) and may be exchanged as desired.

It is also possible for intron sequences to be present between the promoter and the coding region. Such intron sequences may lead to the stability of the expression and to an increased expression in plants (Callis et al., 1987, Genes Devel. 1: 1183-1200; Luehrsen and Walbot 1991, Mol. Gen. Genet. 225: 81-93; Rethmeier et al. 1997, Plant Journal. 12(4): 895-899; Rose and Beliakoff 2000, Plant Physiol. 122 (2): 535-542; Vasil et al., 1989, Plant Physiol. 91: 1575-1579; Xu et al. 2003, Science in China Series C Vol. 46(6): 561-569). Examples of suitable intron sequences are the first intron of the maize sh1 gene, the first intron of the maize poly-ubiquitin gene 1, the first intron of the rice EPSPS gene, or one of the first two introns of the *Arabidopsis* PAT1 gene.

A further embodiment of the present invention relates to a method of generating a genetically modified monocotyledonous plant according to the invention, wherein a plant cell whose starch has an apparent amylose content of less than 5% by weight a) is genetically modified, where the genetic modification leads to an increase in the activity of a protein with the activity of a starch synthase II in comparison with corresponding not genetically modified wild-type plant cells;
b) a plant is regenerated from plant cells of step a);
c) if appropriate, further plants are generated with the aid of the plants in accordance with step b), and
d) plants obtained in accordance with step b) or c) are crossed with a plant which shows an increase in the activity of a protein with the activity of a glucan, water dikinase in comparison with corresponding not genetically modified wild-type plant cells.

A further embodiment of the present invention relates to a method of generating a genetically modified monocotyledonous plant according to the invention, wherein a plant cell whose starch has an apparent amylose content of less than 5% by weight a) is genetically modified, where the genetic modification leads to an increase in the activity of a protein with the activity of a glucan, water dikinase in comparison with corresponding not genetically modified wild-type plant cells;
b) a plant is regenerated from plant cells of step a);
c) if appropriate, further plants are generated with the aid of the plants in accordance with step b), and
d) plants obtained in accordance with step b) or c) are crossed with a plant which shows an increase in the enzymatic activity of a protein with the activity of a starch synthase II in comparison with corresponding not genetically modified wild-type plant cells.

A further embodiment of the present invention relates to a method of generating a genetically modified monocotyledonous plant according to the invention, wherein a plant cell is genetic modified, where a) i) the genetic modification leads to an increase in the activity of a protein with the activity of a glucan, water dikinase;
a) ii) a further genetical modification is carried out which leads to an increase in the activity of a protein with the activity of a starch synthase II
   in comparison with corresponding not genetically modified wild-type plant cells; where steps a) i) and ii) can be carried out in any desired sequence,
b) a plant is regenerated from plant cells of step a) i) and ii);
c) if appropriate, further plants are generated with the aid of the plants in accordance with step b), and
d) plants obtained in accordance with steps a) to c) are crossed with a plant whose starch thus has an amylose content of less than 5% by weight in comparison with corresponding not genetically modified wild-type plant cells.

In the three last-mentioned methods of generating a genetically modified plant, the plants may be genetically modified in accordance with step a), as already described above. The regeneration of plants in accordance with step b) and the generation of further plants in accordance with steps c) and d) have also been detailed further above.

A plant which is crossed in accordance with step d) of the first two embodiments with plants or progeny of the plants obtained from step b) or c) may be any plant which shows an increase in the activity of a protein with the activity of a starch synthase II or an increase in the activity of a protein with the activity of a glucan, water dikinase in comparison with corresponding wild-type plants. The increase in the activity of a protein with the activity of a starch synthase II, or a protein with the activity of a glucan, water dikinase, may have been brought about by any modification which leads to an increase in the activity of the proteins in question in the corresponding plants. These plants may take the form of mutants or of plants which have been modified by recombinant methods. The mutants may take the form of spontaneously (naturally) occurring mutants or else of those which have been generated by the targeted use of mutagens (such as, for example, chemical agents, ionizing radiation) or recombinant methods (for example transposon activation tagging, T-DNA activation tagging, in vivo mutagenesis).

Plants which are preferably used for crosses in the two last-mentioned methods according to the invention are those with an activity of a protein with the activity of a starch synthase II which is increased by at least 3-fold, preferably 6-fold, preferably at least 8-fold and particularly preferably at least 10-fold in comparison with corresponding genetically not modified wild-type plants.

Such plants in question with an increased activity of a protein with the activity of a glucan, water dikinase are used for crosses in the two last-mentioned methods according to the invention are preferably plants which synthesize a starch with a starch phosphate content of at least 2.5 nmol C6P/mg starch.

In a preferred embodiment, methods according to the invention are used for generating a genetically modified plant for generating plants according to the invention or for generating plants which have the characteristics of plants according to the invention.

The present invention also relates to plants obtainable by methods according to the invention.

Surprisingly, it has been found that plant cells according to the invention and plants according to the invention whose starch has an apparent amylose content of less than 5% by weight and an increase in the activity of a protein with the activity of a starch synthase II and an increase in the activity of a protein with the activity of a glucan, water dikinase synthetize a modified starch. The fact that starch synthetized by plant cells according to the invention or plants according to the invention has an increased hot-water swelling power was particularly surprisingly. The increased hot-water swelling power of starches which can be isolated from plant cells according to the invention and plants according to the invention imparts to the starches according to the invention properties which make them better suited to certain applications than traditional starches. If starch is employed for example as a thickener, the increased hot-water swelling power of the starch means that considerably less starch is required for achieving the same thickening power.

A further subject matter of the present invention relates to modified starch with an apparent amylose content of less than 5% by weight and an increased hot-water swelling power. The hot-water swelling power of modified starch according to the invention is increased preferably by at least the factor 1.5, particularly preferably by at least the factor 2, especially preferably by at least the factor 2.5 and very particularly preferably by at least the factor 3 in comparison with starch isolated from corresponding not genetically modified wild-type plant cells or isolated from corresponding not genetically modified wild-type plants.

Methods for determining the hot-water swelling power are known to the skilled worker and described in the literature (for example Leach et al., 1959, Cereal Chemistry 36: 534-544). A method to be used by preference in connection with the present invention for determining the hot-water swelling power is described further below in "General Methods".

A further subject matter of the present invention relates to modified starch, isolated from a monocotyledonous plant cell or from a monocotyledonous plant, with an apparent amylose content of 5% by weight and which has a hot-water swelling power of from at least 60 g/g, preferably of from 60 to 100 g/g, particularly preferably of from 70 to 95 g/g, especially preferably of from 80 to 95 g/g and specifically preferably of from 80 to 90 g/g.

A further subject matter of the present invention relates to modified starch, isolated from rice plant cells or rice plants, with an apparent amylose content of 5% by weight and a hot-water swelling power of from at least 60 g/g, preferably of from 60 to 100 g/g, particularly preferably of from 70 to 95 g/g, especially preferably of from 80 to 95 g/g and specifically preferably of from 80 to 90 g/g.

Starch synthetized by genetically modified plant cells according to the invention or genetically modified plants according to the invention preferably has an increased content of phosphate in the C6 position of the starch. Here, the starch phosphate content of starch isolated from plant cells according to the invention and plants according to the invention is markedly higher than the starch phosphate content which would be expected after making crosses on the basis of the total of the starch phosphate contents of the parent plants in question.

The amount of the starch phosphate bound in the C6 position of the glucose molecules can be determined by methods known to the skilled worker, such as, for example, photometrically by means of coupled enzyme assays or by means of $^{31}$P NMR, following the method described by Kasemusuwan and Jane (1996, Cereal Chemistry 73: 702-707). In the context of the present invention, the amount of starch phosphate bound in the C6 position of the glucose molecules is preferably determined as described in "General Methods".

A further preferred subject matter of the present invention relates to modified starch according to the invention which has been isolated from a monocotyledonous plant cell or from a monocotyledonous plant and which has a starch phosphate content bound in the C6 position of the glucose molecules of the starch of at least 1.5 nmol per mg starch, particularly preferably of at least 2.5 nmol per mg starch. This modified starch according to the invention particularly preferably takes the form of maize, rice or wheat starch.

In a further embodiment of the present invention, the modified starches according to the invention take the form of native starches.

In the context of the present invention, the term "native starch" means that the starch is isolated by methods known to the skilled worker from plants according to the invention, harvestable plant parts according to the invention, starch-storing parts according to the invention or plant propagation material according to the invention.

The present invention also relates to modified starch according to the invention obtainable from plant cells according to the invention or plants according to the invention, from propagation material according to the invention or from harvestable plant parts according to the invention, or obtainable from plants which have been generated using a method according to the invention for generating a genetically modified plant.

Plant cells or plants which synthetize a modified starch according to the invention are likewise subject matter of the present invention.

The present invention furthermore relates to a method of generating a modified starch comprising the step of extracting the starch from a plant cell according to the invention or a plant according to the invention, from propagation material according to the invention of such a plant and/or from harvestable plant parts according to the invention of such a plant, preferably from starch-storing parts according to the invention of such a plant. Preferably, such a method also comprises the step of harvesting the plants or plant parts which have been grown and/or the propagation material of these plants before extracting the starch, and particularly preferably furthermore the step of growing plants according to the invention before harvesting.

Methods for extracting the starch from plants, or from starch-storing parts of plants, are known to the skilled worker. Furthermore, methods for extracting the starch from various starch-storing plants have been described, for example in Starch: Chemistry and Technology (Ed.: Whistler, BeMiller and Paschall (1994), 2nd edition, Academic Press Inc. London Ltd; ISBN 0-12-746270-8; see, for example, chapter XII, page 412-468: Mais and sorghum starches: production; by Watson; chapter XIII, page 469-479: Tapioca, Arrowroot and Sago starches: production; by Corbishley and Miller; chapter XIV, page 479-490: potato starch: production and uses; by Mitch; chapter XV, page 491 to 506: wheat starch: production, modification and uses; by Knight and Oson; and chapter XVI, page 507 to 528: rice starch: production and uses; by Rohmer and Klem; maize starch: Eckhoff et al., 1996, Cereal Chem. 73: 54-57, the extraction of maize starch on the industrial scale is generally accomplished by what is known as wet milling). Devices which are usually employed in processes for extracting starch from plant material are separators, decanters, hydrocyclones, spray dryers and fluidized-bed dryers.

In the context of the present invention, the term "starch-storing parts" are understood as meaning those parts of a plant in which starch, in contrast to transitory leaf starch, is stored as a reserve for surviving for longer periods. Preferred starch-storing plant parts are, for example, tubers, storage roots and grains, particularly preferred are grains comprising an endosperm, especially preferred are grains comprising an endosperm from maize, rice or wheat plants.

In a preferred embodiment, methods according to the invention for preparing a modified starch are used for preparing a starch according to the invention.

Modified starch obtainable by a process according to the invention for preparing modified starch is also a subject matter of the present invention.

The use of plant cells according to the invention or plants according to the invention for preparing a modified starch is also subject matter of the present invention.

The skilled worker knows that the properties of starch can be altered for example via thermal, chemical, enzymatic or mechanical derivatization. Derivatized starches are particularly suitable for a variety of uses in the food and/or nonfood sector. The starches according to the invention are better suited as starting material for the preparation of derivatized starches than conventional starches since they comprise a higher proportion of reactive functional groups, for example as a result of the higher starch phosphate content. As the result of the increased hot-water swelling power of starches according to the invention, the derivatization processes can furthermore be carried out at higher temperatures without the starch granule structure being damaged to a substantial degree.

The present invention therefore also relates to processes for preparing a derivatized starch, wherein modified starch according to the invention is subsequently derivatized. The present invention furthermore relates to a derivatized starch prepared by one of the known processes.

In the context of the present invention, the term "derivatized starch" is understood as meaning a modified starch according to the invention whose properties have been altered with the aid of chemical, enzymatic, thermal or mechanical processes after the starch has been isolated from plant cells.

In another embodiment of the present invention, the derivatized starch according to the invention is heat- and/or acid-treated starch.

In a further embodiment, the derivatized starches take the form of starch ethers, in particular starch alkyl ethers, O-allyl ethers, hydroxyl alkyl ethers, O-carboxylmethyl ethers, nitrogen-containing starch ethers, phosphate-containing starch ethers or sulfur-containing starch ethers.

In a further embodiment, the derivatized starches take the form of crosslinked starches.

In a further embodiment, the derivatized starches take the form of starch graft polymers.

In a further embodiment, the derivatized starches take the form of oxidized starches.

In a further embodiment, the derivatized starches take the form of starch esters, in particular starch esters which have been introduced into the starch using organic acids. They particularly preferably take the form of what are known as phosphate starches, nitrate starches, sulfate starches, xanthate starches, acetate starches or citrate starches.

The derivatized starches according to the invention are suitable for a variety of uses in the pharmaceutical industry, in the food sector and/or in the nonfood sector. Methods of preparing derivatized starches according to the invention are known to the skilled worker and extensively described in the general literature. A review of the preparation of derivatized starches is found for example in Orthoefer (in Corn, Chemistry and Technology, 1987, eds. Watson and Ramstad, Chapter 16: 479-499).

Derivatized starch obtainable by the process according to the invention for preparing a derivatized starch is likewise subject matter of the present invention.

The use of modified starches according to the invention for the preparation of derivatized starch is furthermore subject matter of the present invention.

The present invention also comprises products comprising a starch according to the invention.

The present invention also comprises mixtures comprising the starch according to the invention.

Starch-storing parts of plants are frequently processed into flours. Examples of parts of plants from which flours are prepared are, for example, tubers of potato plants and grains of cereal plants. To prepare flours from cereal plants, the endosperm-containing grains of these plants are ground and sieved. Starch is a main constituent of the endosperm. In other plants which comprise no endosperm, but other starch-storing parts such as, for example, tubers or roots, flour is frequently prepared by comminuting, drying and subsequently grinding the storage organs in question. The starch of the endosperm or present in starch-storing parts of plants accounts for a considerable proportion of the flour which is prepared from the plant parts in question. The properties of flours are therefore also influenced by the starch present in the flour in question. Plant cells according to the invention and plants according to the invention synthesize an altered starch in comparison with corresponding not genetically modified wild-type plant cells, or not genetically modified wild-type plants. Flours prepared from plant cells according to the invention, plants according to the invention, propagation material according to the invention or harvestable parts according to the invention therefore have altered properties. The properties of flours may also be influenced by mixing starch with flours or by mixing flours with different properties.

A further subject matter of the present invention therefore relates to flours comprising a starch according to the invention.

A further subject matter of the present invention relates to flours which can be prepared from plant cells according to the invention, plants according to the invention, starch-storing parts of plants according to the invention, from propagation material according to the invention or from harvestable plant parts according to the invention. Preferred starch-storing parts of plants according to the invention for the preparation of flours are tubers, storage roots and grains which comprise an endosperm. Particularly preferred in the context of the present invention are grains from plants of the (systematic) family Poaceae; especially preferably, grains are obtained from maize, rice or wheat plants.

In the context of the present invention, the term "flour" is understood as meaning a powder which can be obtained by grinding plant parts. If appropriate, plant parts are dried and sieved prior to grinding.

On account of the starch according to the invention present in them, flours according to the invention are distinguished by the fact that they have an increased hot-water swelling power. This is desirable for example in the processing of flours in the food industry for a multiplicity of applications, in particular in the production of baked good.

A preferred subject matter of the present invention relates to flours prepared from grains of a monocotyledonous waxy plant, which flours have a hot-water swelling power of at least 25 g/g, preferably of from 25 to 50 g/g, particularly preferably of from 30 to 45 g/g and especially preferably of from 35 to 45 g/g.

In this context, the determination of the hot-water swelling power of flours is effected analogously to the above-described method for determining the hot-water swelling power for starch, with the difference that flours are employed in place of starch. A preferred method of determining the hot-water swelling power of flours is described in "General Methods".

A further subject matter of the present invention is a process for the preparation of flours, comprising the step of grinding plant cells according to the invention, plants according to the invention, parts of plants according to the invention, starch-storing parts of plants according to the invention, propagation material according to the invention or harvestable material according to the invention.

Flours can be produced by grinding starch-storing parts of plants according to the invention. The skilled worker knows how to produce flours. Preferably, a process for the production of flours also comprises the step of harvesting the plants or plant parts which are grown and/or the propagation material and/or the starch-storing parts of these plants before grinding, and particularly preferably furthermore the step of growing plants according to the invention before harvesting.

Products comprising a flour according to the invention are likewise subject matter of the present invention.

In a further embodiment of the present invention, the process for the production of flours comprises the processing of plants according to the invention, of starch-storing parts of plants according to the invention, of propagation material according to the invention or of harvestable material according to the invention prior to grinding.

In this context, processing may be a heat treatment and/or a drying step. A heat treatment followed by the drying of the heat-treated material is employed for example in the production of flours from storage roots or tubers such as, for example, from potato tubers, before grinding takes place. The comminution of plants according to the invention, of starch-storing parts of plants according to the invention, of propagation material according to the invention or of harvestable material according to the invention before grinding may likewise constitute processing within the meaning of the present invention. The removal of plant tissue before grinding, such as, for example, hulling the grains, also constitutes processing before grinding within the meaning of the present invention.

In a further embodiment of the present invention, the process for the preparation of flours comprises processing the mill base after grinding. In this context, the mill base may be sieved after grinding in order to prepare various types of flours.

The present invention also comprises mixtures comprising a flour according to the invention.

A further subject matter of the present invention is the use of genetically modified plant cells according to the invention, of plants according to the invention, of parts of plants according to the invention, of starch-storing parts of plants according to the invention, of propagation material according to the invention or of harvestable material according to the invention for the preparation of flours.

The disclosure of all documents cited in the patent application is intended to be incorporated in the disclosure of the present description of the invention.

DESCRIPTION OF THE SEQUENCES

SEQ ID NO 1: Nucleic acid sequence coding for a protein with the activity of a glucan, water dikinase from *Solanum tuberosum*.

SEQ ID NO 2: Amino acid sequence of the protein encoded by SEQ ID NO 1 with the activity of a glucan, water dikinase from *Solanum tuberosum*.

SEQ ID NO 3: Nucleic acid sequence coding for a protein with the activity of a starch synthase II from *Triticum aestivum*.

SEQ ID NO 4: Amino acid sequence of the protein encoded by SEQ ID NO 3 with the activity of a starch synthase II from *Triticum aestivum*.

SEQ ID NO 5: Nucleic acid sequence coding for a protein with the activity of a starch synthase II from *Oryza sativa*.

SEQ ID NO 6: Amino acid sequence of the protein encoded by SEQ ID NO 5 with the activity of a starch synthase II from *Oryza sativa*.

SEQ ID NO 7: Nucleic acid sequence coding for a protein with the activity of a GBSS I from *Oryza sativa*.

SEQ ID NO 8: Amino acid sequence of the protein encoded by SEQ ID NO 7 with the activity of a GBSS I from *Oryza sativa*.

SEQ ID NO 9: Nucleic acid sequence coding for a protein with the activity of a GBSS I from *Triticum aestivum*.

SEQ ID NO 10: Amino acid sequence of the protein encoded by SEQ ID NO 9 with the activity of a GBSS I from *Triticum aestivum*

SEQ ID NO 11: Nucleic acid sequence coding for a protein with the activity of a GBSS I from *Zea mays*.

SEQ ID NO 12: Amino acid sequence of the protein encoded by SEQ ID NO 11 with the activity of a GBSS I from *Zea mays*

General Methods

In the following text, methods will be described which can be used for carrying out the methods/processes according to the invention. These methods are specific embodiments of the present invention, but do not limit the present invention to these methods. The skilled worker knows that he can carry out the invention in the same manner by modifying the methods described and/or by replacing individual parts of the methods by alternative parts of methods. The content of all cited publications is incorporated into the description of the application by reference.

1. Transformation and Regeneration of Rice Plants

Rice plants were transformed by the method described by Hiei et al. (1994, Plant Journal 6(2), 271-282).

The regimen of the rice plants in the greenhouse involved the following conditions: sowing: substrate: mixture of 100% sphagnum peat and 100 l sand/m$^2$ and clay: 180 kg/m$^2$ in 1.6 l rose pots (manufacturer: H. Meyer, Germany), pH: 5.4-6.2; green manure: Hakaphos (Compo, Germany) 14% N–16% P–18% K+2% Mg; 2 kg/m$^2$; fertilization: 3.5 g/plant until flowering: NH$_4$NO$_3$ (1.75 g) and Flory 2 basic mixture (manufacturer: Euflor, Germany): 1.75 g; 3% N–16% P–15% K+5% Mg.

Temperature: day 28° C./night: 24° C. (16 h/8 h); relative atmospheric humidity: 85-95%;

Light: 16 h, 350 µEinstein/sxm$^2$

2. Origin of the Sequences and Constructs Used for the Transformation

The sequence T.a.-SSIIa from wheat was used for the transformation of rice. It was isolated and cloned as described in WO 97-45545 (under its then name "pTaSS1").

The transformation vector used, AH32-191, is described in example 2.

The sequence of a glucan, water dikinase from potato (R1St) was furthermore used. It was isolated and cloned as described in example 5. The transformation vector used, pML82, is described in WO 05/095619.

The waxy trait was introduced via a suitable mutant which is explained in example 1.

3. Analysis of the Expression Level of a Gene by Means of Northern Blot

The expression of a nucleic acid which codes for a protein was studied by means of Northern blot analysis. To this end, three immature rice grains (approximately 15 days after anthesis) were harvested for each individual plant obtained by means of transformation and frozen in liquid nitrogen. To homogenize the material, the frozen rice grains were comminuted for 30 seconds in a Retsch mill (model MM300) in a 96-well microtiter plate using a 4.5 mm steel ball at a frequency of 30 Hertz. Thereafter, the RNA was isolated by means of the Promega RNA extraction kit following the manufacturer's instructions (SV 96 Total RNA Isolation System, Order No. Z3505, Promega, Mannheim). The concentration of the RNA in the individual samples was determined by photometrically measuring the absorption at 260 nm.

For each sample, 2 µg of RNA were brought to a uniform volume and treated with an identical volume of RNA sample buffer (65% (v/v) formamide, 8% formaldehyde, 13% (v/v) gel buffer (see above), 50 µg/ml ethidium bromide). After heating (10 min, 65° C.) and immediate cooling on ice, the RNA was separated for approximately 2 hours using a 1.2% (w/v) agarose gel (20 mM MOPS pH 8.0, 5 mM sodium acetate, 1 mM EDTA, 6% (v/v) formaldehyde) using RNA running buffer (20 mM MOPS pH 8.0, 5 mM sodium acetate, 1 mM EDTA) at a constant amperage of 50-80 mA.

Thereafter, the RNA was transferred to a Hybond N membrane by means of diffusion blot using 10×SSC (1.5 M NaCl, 150 mM sodium citrate pH 7.0) and immobilized on the membrane by means of UV irradiation.

The hybridization of the Northern blot for detecting the expression of a nucleic acid molecule which codes for a protein with the activity of a starch synthase II from wheat employed an approx. 1 kb SpeI/BspHI fragment of the plasmid AH32-191 (bp 4568-5686), which encompasses the 5' region of the cDNA. The DNA fragment was radiolabeled by means of the Random Primed DNA Labeling Kit from Roche (Order No. 1004 760) using $^{32}$P-alpha-dCTP and following the manufacturer's instructions. The nylon membrane comprising the transferred RNA was incubated for 4 hours at 60° C. in a water bath with hybridization buffer (250 mM sodium phosphate buffer pH 7.2, 1 mM EDTA, 6% (w/v) SDS, 1% (w/v) BSA), with gentle shaking, whereupon the radiolabel DNA was added to the hybridization buffer. After incubation for 16 hours, the hybridization buffer was removed, and the membrane was washed in succession once with 3×SSC and once with 2×SSC (see above) at 60° C., with gentle shaking, to remove unspecifically bound DNA molecules.

To detect labeled RNA, the nylon membrane was autoradiographed for one to three days at −70° C. on an x-ray film.

4. Determination of the Activity of a Protein with the Activity of a Starch Synthase II by Means of Activity Gels (Zymogramm)

The detection of the activity of proteins with the activity of a starch synthase in immature rice grains was performed by means of activity gels (zymogramms), in which protein extracts are separated in a polyacrylamide gel under native conditions and subsequently incubated with suitable substrates. The reaction product formed (alpha-glucan) was stained in the gel using Lugol's solution.

Individual immature rice grains (approx. 15 days after anthesis) were frozen in liquid nitrogen and homogenized in 150-200 µl of cold extraction buffer (50 mM Tris/HCl pH 7.6, 2.5 mM EDTA, 2 mM DTT, 4 mM PMSF, 0.1% (w/v) glycogen, 10% (v/v) glycerol). After centrifugation (15 min, 13000 g, 4° C.), the clear supernatant was transferred into a fresh reaction vessel, and an aliquot of the extract was used for determining the protein content by the method of Bradford (1976, Anal Biochem 72: 248-254).

The protein extracts were separated by means of continuous 7.5% strength polyacrylamide gel (7.5% acrylamide: bisacrylamide 37.5:1; 25 mM Tris/HCl pH 7.6, 192 mM glycine, 0.1% (w/v) APS, 0.05% (v/v) TEMED) using running buffer in single concentration (25 mM Tris/HCl, 192 mM glycine). For each sample, amounts corresponding to 15 µg of protein were applied in each case, and the electrophoresis was run for 2 to 2.5 hours at 4° C.

Thereafter, the gels were incubated overnight at room temperature in 15 ml of incubation buffer (0.5 mM sodium citrate pH 7.0, 25 mM potassium acetate, 2 mM EDTA, 2 mM DTT, 0.1% (w/v) amylopectin, 50 mM tricine/NaOH pH 8.5, 1 mM ADP-glucose), with constant shaking. The starch formed was stained by means of Lugol's solution.

To determine by how many times the activity of a protein with the activity of a starch synthase II is increased in comparison with corresponding not genetically modified wild-type plants, protein extracts from the genetically modified lines were in each case subjected to sequential dilution and separated by electrophoresis in accordance with the above-described method. The remaining steps were carried out as already described above. After the zymogramms had been stained with Lugol's solution, the intensity of the stained products produced by a protein with the activity of a starch synthase II (identified by an arrow in FIG. 1) for the different dilutions of the protein extracts from genetically modified plants were compared visually with the relevant products of the undiluted wild-type protein extract. Since the intensity of the coloration of the products correlates directly with the activity of a protein with the activity of a starch synthase II, product bands with the same intensities have the same activity. If the band of the product of a protein with the activity of a starch synthase II in the dilute protein extract has the same intensity as the corresponding band of the product from corresponding undiluted protein extract from wild-type plants, the dilution factor corresponds to the degree of the increase in the activity in the corresponding genetically modified plant (for comparisons, see FIG. 1).

5. Generation of Plants from Isolated Rice Embryos (Embryo Rescue)

Seeds are removed from the panicle, and the shells are removed. The endosperm is dissected from the embryo using a surgical blade and used for suitable analyses. To improve the wettability, the embryo is briefly treated with 70% ethanol and subsequently incubated for 20 minutes in a solution comprising 2% NaOCl and one drop of commercially available washing-up liquid to sterilize it.

Thereafter, as much as possible of the sterilization solution is removed, and the embryo is washed with sterile demineralized water, once for a minute and thereafter twice for in each case 10 minutes. The seeds are plated out in Petri dishes on agar solidified medium comprising in each case a quarter of the salt concentration of MS medium (Murashige-Skoog medium) and 4% sucrose. Thereafter, the Petri dishes are sealed using Parafilm and incubated in the dark at 23° C. After germination (approx. 5-7 days after plating out the embryos), the Petri dishes are transferred into the light. When the hypocotyls of the seedlings have reached a length of approx. 2 cm, the plants are transferred into jars comprising agar-solidified MS medium with 2% sucrose. After sufficient roots have developed, the plants can be potted in compost.

6. Processing of Rice Grains, and Preparation of Rice Flours

To prepare sufficient amounts of test material, rice plants were grown in the greenhouse and harvested when fully mature. The mature rice grains were stored for 3-7 days at 37° C. to dry them further.

Thereafter, the grains were freed from the shells by means of a sheller (Laboratory Paddy sheller, Grainman, Miami, Fla., USA), and the brown rice obtained was processed by polishing for 1 minute (Pearlest Rice Polisher, Kett, Villa Park, Calif., USA) to give white rice. For grain composition studies and starch property studies, the white grains were ground by means of a laboratory mill (Cyclotec, Sample mill, Foss, Denmark) to give what is known as rice flour.

7. Extraction of Rice Starch from Rice Flour

Rice starch was extracted from rice flour by a method similar to the method described by Wang and Wang (2004; Journal of Cereal Science 39: 291-296).

Approx. 10 g of rice flour were incubated for 16-18 hours with 40 ml of 0.05% (w/v) NaOH at room temperature on a shaker. Thereafter, the suspension was transferred into a Waring blender to complete the digestion and mixed for 15 seconds at low speed and subsequently for 45 seconds at high speed. To remove coarse constituents (for example cell wall), the suspension was poured in succession through sieves with a mesh size of 125 p$\mu$m and of 63 $\mu$m. After centrifugation at 1500 rpm for 15 minutes (Microfuge 3.OR; Heraeus), the supernatant was decanted off, and the protein layer at the top of the sediment was removed using a spatula. The remainder of the sediment was resuspended in 0.05% (w/v) NaOH, and the procedure described above was repeated. Thereafter, the sediment was resuspended in water and the pH of the suspension was brought to 6.5 to 7 using HCl. The rice starch obtained was washed in total three times with water, where each wash step comprised a sedimentation (centrifugation at 1500 rpm, 15 min, RT), discarding the supernatant and resuspending the sediment in fresh water. Before the last wash step, the pH was rechecked and, if necessary, brought to pH 7 with HCl. The sediment of the last wash step was resuspended in acetone, sedimented and the supernatant was discarded. After resuspending the sediment again in acetone, the suspension was poured into a Petri dish and dried in a fume hood at room temperature for at least 18 hours.

In a last step, the resulting rice starch was made into a fine powder by comminuting in a pestle and mortar, and this powder can be employed directly for further studies.

8. Determination of the Hot-Water Swelling Power (SP)

100 mg of sample (starch or flour) are suspended in 10 ml of water and subsequently swelled for 20 minutes at 92.5° C. During the incubation of the sample of 92.5° C., the suspension is mixed repeatedly (continuously during the first 2 minutes, then after 3, 4, 5, 10, 15 and 25 minutes) by carefully turning the sample containers by 360°. After incubation for a total of 30 minutes at 92.5° C., the suspension is cooled for approx. 1 minute in ice-water before carrying out an incubation at 25° C. for 5 minutes. After centrifugation (room temperature, 1000×g, 15 minutes), the supernatant obtained is removed carefully from the gel-like sediment and the sediment weight is determined. The hot-water swelling power is calculated using the following formula:

$$SP=\text{(weight of the gel-like sediments)}/\text{(weight of the weighed-in sample (flour or starch))}$$

9. Determination of the Starch Phosphate Content in the C6 Position of the Glucose Molecules In starch, the positions C2, C3 and C6 of the glucose units may be phosphorylated. To determine the C6-P content of the starch or the flour (modified method of Nielsen et al., 1994, Plant Physiol. 105: 111-117), 50 mg of rice flour or rice starch were hydrolyzed for 4 hours in 500 $\mu$l of 0.7 M HCl at 95° C., with continuous shaking. Thereafter, the mixtures were centrifuged for 10 minutes at 15.500×g, and the supernatants were freed from suspended matter and cloudiness by means of a filter membrane (0.45 $\mu$M). 20 $\mu$l of the clear hydrolyzate were mixed with 180 $\mu$l of imidazol buffer (300 mM imidazol, pH 7.4; 7.5 mM MgCl2, 1 mM EDTA and 0.4 mM NADP), and the samples were measured in a photometer at 340 nm. After recording the basic absorption, an enzyme reaction was started by addition of 2 units of glucose 6-phosphate dehydrogenase (from *Leuconostoc mesenteroides*, Boehringer Mannheim). The measured change (OD) is based on an equimolar conversion of glucose 6-phosphate and NADP to give 6-phosphogluconate and NADPH, where the formation of NADPH is recorded at the abovementioned wavelength. The reaction was monitored until an end point had been reached. The result of this measurement can be used for calculating the glucose 6-phosphate content in the hydrolyzate:

$$\text{nmol glucose 6-phosphate/mg } FW = \frac{OD \times \text{measuring volume } (200\ \mu l) \times \text{hydrolyzate volume } (500\ \mu l)}{\text{extinction coefficient} \times \text{sample volume } (20\ \mu l) \times \text{mg material weighed in } (50\ mg)}$$

To avoid erroneous results caused by incomplete hydrolysis of the starch in the material weighed in (flour or starch), the degree of hydrolysis was subsequently determined. To this end, 10 $\mu$l of hydrolyzate was removed from the respective hydrolyzates which were measured by their glucose 6-phosphate content, neutralized with 10 $\mu$l of 0.7 M NaOH and brought to a final volume of 2 ml with water (dilution 1:200). 4 $\mu$l of this dilution were treated with 196 $\mu$l of measuring buffer (100 mM imidazole pH 6.9; 5 mM MgCl2, 1 mM ATP, 0.4 mM NADP) and used for the photometric determination of the glucose content. After determining the basic absorption at 340 nm, the reaction was monitored until the end point was reached in the photometer (340 nm) by addition of 2 μl of enzyme mix (hexokinase 1:10; glucose 6-phosphate dehydrogenase from yeast 1:10 in measuring buffer). The principle of the measurement corresponds to that of the first reaction. Using the data obtained, the amount of glucose can be calculated for the sample in question:

$$\text{mmol Glucose/g } FW = \frac{OD \times \text{measuring volume} (200\ \mu l) \times \text{hydrolyzate volume} (500\ \mu l) \times \text{total volume of the dilution} (2\ ml)}{\text{extinction coefficient} \times \text{sample volume} (20\ \mu l) \times \text{volume employed for the dilution} (10\ \mu l) \times \text{mg material weighed in} (50\ mg)}$$

The amount of glucose detected in the individual samples corresponds to the amount of starch which is available for the C6-phosphate determination. To simplify the further calculation, the glucose content is converted into starch content.

$$\text{starch content } (\%) = \frac{\text{glucose content (mmol/g } FW) \times \text{molecular weight of glucose in starch} (162\ g/mol) \times \text{conversion factor} (\% = 100)}{\text{conversion factor (mmol to mol} = 1000)}$$

In what follows, the result of the glucose 6-phosphate measurement is related to the starch content of the sample in question in order to express, in this manner, the glucose 6-phosphate content per mg of hydrolyzed starch:

$$\text{nmol } Glc\text{-}6\ P/\text{mg starch} = \frac{\text{nmol glucose 6-phosphate/mg material weighed in} \times \text{starch content}}{(mg\ starch/100\ mg\ material\ weighed\ in)}$$

In contrast to when relating the amount of glucose 6-phosphate to the weighed-in weight of the sample (flour or starch), this type of calculation relates the amount of glucose 6-phosphate only to the amount of starch which has been completely hydrolyzed to give glucose.

10. Determination of the Apparent Amylose Content

The determination of the apparent amylose content was carried out by a method similar to that of Juliano (1971, Cereal Science Today 16 (10): 334-340).

For each sample, 50 mg of rice flour were weighed, in duplicate, in 100 ml Erlenmeyer flasks and consecutively moistened with 1 ml of 95% strength ethanol and 9 ml of 1M NaOH.

In parallel, flasks with defined amounts of pure amylose from potato starch are treated in the same manner as the flour samples, in order to establish a calibration curve. The flasks were swirled briefly to mix the contents and subsequently incubated for 20 minutes in a boiling water bath, with gentle shaking. After 5-10 minutes cooling at RT, the volume was made up to 100 ml with water.

A 100 μl aliquot was treated with 1 ml measuring solution (10 mM acetic acid, 0.004% (w/v) $I_2$; 0.04% (w/v) KI), mixed thoroughly, and the absorption was determined at 620 nm against a suitable blank. The calculation of the amylose content was carried out with the aid of the amylose standards used for establishing a calibration curve.

11. Quantitative PCR

RNA was prepared from individual immature rice seeds (10-12 days after anthesis). After the seeds, which had been frozen in liquid nitrogen, had been homogenized using a 4 mm steel ball (Retsch mill, 30 Hz, 45 sec), the RNA was prepared using the "SV 96 Total RNA Isolation System" by Promega, following protocol No. 294 (Promega). The RNA was treated with in each case 10 μl of "RQ1 RNase-Free DNase" (Promega), following the manufacturer's instructions.

Identical amounts of RNA from in each case four seeds of one plant were combined. The quantitative RT-PCR was carried out with reagents of the "Access RT-PCR System" by Promega.

The reaction conditions for the RT-PCR were: 30 min at 55° C., 2 min at 94° C., 40×(15 sec 94° C., 1 min 60° C.). The fluorescent signal was recorded using an ABI Prism 7700 apparatus (Applied Biosystems), in each case during the combined annealing/extension phase.

The controls which were employed in this approach were in each case mixtures without reverse transcriptases.

The relative expression was calculated as described by M. W. Pfaffl (2001, A new mathematical model for relative quantification in real-time RT-PCR, Nucleic Acids Research 29, No 9 00).

Examples

1. Generation and Selection of the Waxy (GBSSI Knock Out) Mutant

The waxy mutant originated from an agrobacteria-mediated transformation of rice. An analysis of the progeny revealed that the waxy phenotype of the rice grains is inherited independently of the phosphinotricine resistance introduced with the transformation. A sequence analysis of the GBSSI (waxy) gene revealed that the manifestation of the waxy phenotype gene can be attributed to the exchange of two nucleotides, as a result of which a premature stop codon is generated, which leads to a truncated and probably inactive protein. The RFLP analysis of the apparent amylose content of the starch present in the rice grains confirmed a value of less than 5% by weight, which means that the mutant identified is a "waxy" mutant. As a consequence, the term "waxy phenotype" is understood as meaning waxy mutants whose starch has an apparent amylose content of less than 5%.

Lines 738-104 and 738-106, which are homozygous for the above-mentioned mutation, were used for the combination with the transgenic approaches.

```
                              BamHI
M202           GAG TGG GAT CCT AGC

Waxy_Mutant    GAG TGA AAT CCT AGC
                   Stop
```

2. Preparation of the Plant Expression Vector pAH32-191, which Comprises a Coding Sequence for a Protein with the Activity of a Starch Synthase II The complete encoding sequence of the protein with the activity of a starch synthase II from wheat (T.a.-SSII) was excised from the plasmid pCF31 (described in WO 97/45545 under the name pTaSS1) by means of the restriction endonucleases Ecl13611 and Xho I and cloned into the plasmid pIR103-123 (described in WO 05/030941) which had been cleaved with the restriction endonucleases Eco RV and Xho I. The expression vector obtained was named pAH32-191. The plant expression vector pIR103-123 serves for the endosperm-specific expression of the target gene under the control of the endosperm-specific globulin promoter (Nakase et al. (1996) Gene 170(2): 223-226) from rice. In addition, the plant expression vector pIR103-123 comprises the bar gene under the control of the CaMV 35S promoter, which gene was used as the selection marker for the transformation of plants.

3. Generation of Rice Plants with an Increased Activity of a Protein with the Activity of a Starch Synthase II Rice plants (variety M202) were transformed by means of agrobacteria comprising the plasmid pAH32-191 using the method described by Hiei et al. (1994, Plant Journal 6(2), 271-282). The resulting plants were named oe-SSII-O.s.-X, where X means independent plants obtained from the transformation.

4. Analysis of the Rice Plants which Had been Transformed with the Expression Vector pAH32-191

Rice plants (T0 plants) of the lines named oe-SSII-O.s.-X and which had originated from the transformation with the expression vector pAH32-191 where grown in soil in the greenhouse. RNA was isolated from immature grains (T1 seeds) of various lines, and a Northern blot analysis was carried out in accordance with the method described in "General Methods", using an SSII-specific probe. A plurality of lines with an increased amount of transcript of the wheat starch synthase II in comparison with corresponding not genetically modified wild-type plants were identified (see diagram shown by way of example in FIG. 2).

In addition, an increased activity of a protein with the activity of a starch synthase II in protein extracts of immature T1 seeds from different lines of the above-mentioned transformation was determined by means of zymograms (see diagram shown by way of example in FIGS. 1 and 2). The analysis was carried out by means of zymograms as described in "General Methods".

Based on the results of the analyses described, the following line was selected for the combination with other approaches:

oe-SSII-O.s-01502

On the basis of a variety of analyses, it was possible to demonstrate that this line is homozygous for the integrations of the T-DNA(s) of the vector pAH32-191.

5. Generation of Rice Plants with an Increased Activity of a Protein with the Activity of a Glucan, Water Dikinase Rice plants (variety M202) were transformed by means of agrobacteria which comprise the plasmid pML82 (described in WO 05/095619), using the method described by Hiei et al. (1994, Plant Journal 6(2), 271-282). The resulting plants were named oe-GWD-O.s.-X, where X means independent plants obtained from the transformation.

6. Analysis of the Rice Plants which Had been Transformed with the Expression Vector pML82

Rice plants (T0 plants) of the lines named oe-GWD-O.s.-X and which had originated from the transformation with the expression vector pML82 were grown in soil in the greenhouse. Individual, mature grains (T1 seeds) from different lines were made into a flour. To this end, individual grains were comminuted, in a ball mill (from Retsch, Model MM300), for 30 seconds at a frequency of 30 Hertz in an Eppendorf reaction vessel using a tungsten carbide ball. This was followed by a determination of the starch phosphate content in the C6 position of glucose molecules of the starch present in the flour as described in "General Methods".

The following results were obtained for selected plants:

TABLE 1

Starch phosphate content in the C6 position of the glucose molecules of individual T1 seeds from different lines with the name oe-GWD-O.s.-X in comparison with seeds of corresponding not genetically modified wild-type plants (WT) of variety M202.

| Line | nmol C6P/mg material weighed |
|---|---|
| oe-GWD-O.s.-2 | 1.68 |
| oe-GWD-O.s.-4 | 1.70 |
| oe-GWD-O.s.-9 | 1.47 |
| WT | 0.30 |

As can be seen from table 1, it was possible to identify independent lines which are the result of the transformation with the plant expression vector pML82 and which, in comparison with corresponding not genetically modified wild-type plants have an increased starch phosphate content in the C6 position of the glucose molecules. It is known that plant cells with an increased expression of a protein with the activity of a glucan, water dikinase synthesize a starch with a higher starch phosphate content in comparison with corresponding genetically not modified wild-type plants (see, for example, WO 02/34923).

Based on the above-described analyses, the following lines were selected for the combination with other approaches:

oe-GWD-O.s.-2 oe-GWD-O.s.-4 oe-GWD-O.s.-9

On the basis of various analyses, it was possible to demonstrate that these lines are homozygous for the integrations of the T-DNA(s) of vector pML82.

7. Generation of Plants with a Waxy Phenotype and an Increased Activity of a Protein with the Activity of a Glucan, Water Dikinase The following crosses were made:

TABLE 2

Crosses of the combination of 738-104/4 (M202 waxy) with oe-GWD-O.s.

| Pedigree cross | | Name of female parent | Plasmid of female parent | Name of male parent | Plasmid of male parent |
|---|---|---|---|---|---|
| XPOS0001 | | M202 waxy | — | oe-GWD-O.s. | pML82 |
| | −01 | 738-106 | — | oe-GWD-O.s-2 | pML82 |
| | −02 | 738-104 | — | oe-GWD-O.s-2 | pML82 |
| | −03 | 738-104 | — | oe-GWD-O.s-4 | pML82 |
| | −04 | 738-106 | — | oe-GWD-O.s-4 | pML82 |
| | −05 | 738-104 | — | oe-GWD-O.s-9 | pML82 |
| | −06 | 738-106 | — | oe-GWD-O.s-9 | pML82 |

The endosperm of the F1 seeds, which were the result of the cross, was studied for the starch phosphate content in the C6 position of the glucose molecules (C6P). The embryos of those grains whose starch phosphate content (C6P) was markedly increased in comparison with the female parent were germinated by means of tissue culture techniques. After a sufficient size had been attained, relevant plants were transferred to the greenhouse in order to produce F2 seeds.

Grains with waxy phenotype were selected from the mature F2 seeds by means of visual scoring and placed in the greenhouse. After germination, the plants were sprayed with Basta® (Bayer CropScience), and leaf samples were taken from Basta®-tolerant plants. Plants which were homozygous for the integration of the T-DNA of vector pML82 were identified by means of a copy number determination using invader technology (http://www.twt.com/invader_chemistry/invaderchem.htm; Ledford et al (2000, J. of Mol. Diagnostics. 2(2): 97-104; Mein et al., 2000, Genome Res. 10: 330-343) for the bar gene. The plants thus selected were grown on in the greenhouse for the production of F3 seeds.

Some mature F3 seeds of the potentially doubly homozygous plants were studied individually for their starch phosphate (C6P) content. Those plants where all grains had an expectedly high starch phosphate (C6P) content were retained.

The seed of all doubly homozygous plants of a parental combination was pooled and used for further propagation and for grain and flour property analyses.

For the combination with line oe-SSII-O.s, the event XPOS0001-05, which is homozygous both for the waxy mutation and for the T-DNA of the vector pML82, was selected.

8. Generation of Plants with a Waxy Phenotype and with an Increased Activity of a Protein with the Activity of a Glucan, Water Dikinase and with an Increased Activity of a Protein with the Activity of a Starch Synthase II The following crosses were made:

TABLE 3

Crosses of the combination of oe-SSII-O.s. with XPOS0001-05

| Pedigree cross | Female parent | Plasmid of female parent | Male parent | Plasmid of male parent |
|---|---|---|---|---|
| XPOS0025-01 | oe-SSII-O.s.-01502 | pAH31-191 | XPOS0001-05 | pML82 |
| XPOS0026-01 | XPOS0001-05 | pML82 | oe-SSII-O.s.-01502 | pAH32-191 |

Successful events in crosses were identified by measuring the starch phosphate content of the F1 endosperm, since the starch phosphate content of the combination is markedly higher than that of the parental lines.

9. Analysis of Plants with a Waxy Phenotype and with an Increased Activity of a Protein with the Activity of a Glucan, Water Dikinase and with an Increased Activity of a Protein with the Activity of a Starch Synthase II Embryos of F1 seeds whose endosperm has a starch phosphate content of more than 5 nmol C6P/mg starch and is therefore markedly above that of both parents (2.5 nmol/mg starch for oe-GWD-O.s. and at least 0.8 nmol/mg starch for oe-SSII-O.s.) were germinated by means of tissue culture techniques, and the plants in question, once they had reached a suitable size, were transferred to the greenhouse to produce F2 seeds.

To identify progeny which is homozygous for both transgenes and for the waxy mutation, the above-described procedure was repeated for F2 seeds which had been preselected visually with regard to a "waxy phenotype", including the embryo rescue.

10. Selection and Analysis of the F2 Plants

Based on the results of the starch phosphate measurement, F2 seeds were selected (C6P>8 nmol/mg starch), their embryos were germinated, and the F2 plants in question were grown in the greenhouse.

Genomic DNA was extracted from leaf material of the F2 plants, and the copy number of the two transgenes and of the bar gene (total of the values for the two transgenes) was determined by means of quantitative PCR.

The proof that the waxy mutation was homozygous was carried out using an RFLP(Bam HI) in the GBSSI gene (definition and/or method) of the waxy mutant. F2 plants which are potentially homozygous for the two transgenes and homozygous for the waxy RFLP were grown on in the greenhouse and used for the production of F3 seeds.

11. Selection of the F3 Plants/Analysis of F3 Seeds

To identify triply homozygous lines, some individual grains of suitably selected plants were examined visually for a waxy phenotype and subsequently studied for their starch phosphate content. If all grains have a waxy phenotype, and if the starch phosphate content for all grains of one plant is found to be approximately equally high, it can be assumed that the plant is homozygous for the waxy mutation and for the T-DNA of pML82 and pAH32-191.

12. Generation of F4 Material

The following lines were found in the abovementioned analysis to be triply homozygous:

XPOS002501-1-37

XPOS002501-1-13

XPOS002601-1-19

Plants from these lines were grown in the greenhouse, and the F4 seeds produced were harvested and dried and then pooled as one line for all progeny.

13. Functionalities and Analysis of the Constituents of the F4 Material a) Grain Composition Apparent Amylose Content:

TABLE 4

Apparent amylose content in rice flours and rice starches for the single-gene approaches and the triple combination

| Sample name | Apparent amylose content of rice flours (% amylose/FW) | Apparent amylose content of rice starches (% amylose/FW) |
|---|---|---|
| Wild type | 8.9 | 11.8 |
| oe-GWD-O.s.-4 | 10.6 | 14.4 |
| oe-GWD-O.s.-9 | 10.6 | 14.3 |
| oe-SSII-O.s.-01502 | 6.6 | 9.2 |
| 738-104/6 | 2.3 | 2.2 |
| XPOS025-01-1-37 | 3.7 | 3.5 |
| XPOS025-01-1-13 | 3.7 | 3.7 |
| XPOS026-01-1-19 | 3.9 | 4.1 |

It emerged that the combinations XPOS0025/6 have an amylase content above that of the waxy mutant (738-104/6).

Starch Phosphate Content (C6P Contents)

TABLE 5

Starch phosphate content in the C6 position of rice flours or starches for the single-gene approaches and for the triple combinations

| Sample name | Starch phosphate content in the C6 position of starches present in rice flours (nmol C6P/mg starch) | Starch phosphate content in the C6 position of rice starches (nmol C6P/mg starch) |
|---|---|---|
| Wild type | 0.46 | 0.37 |
| oe-GWD-O.s.-4 | 2.85 | 2.65 |
| oe-GWD-O.s.-9 | 3.27 | 2.56 |
| oe-SSII-O.s.-01502 | 1.22 | 0.91 |
| 738-104/6 | 0.52 | 0.38 |
| XPOS025-01-1-37 | 11.45 | 9.50 |
| XPOS025-01-1-13 | 11.20 | 10.24 |
| XPOS026-01-1-19 | 11.06 | 10.23 |

The starch phosphate content in the C6 position of the triple combination is markedly higher than that of the single-gene approaches.

b) Functionalities of Rice Flours and Rice Starches

Hot-Water Swelling Power

TABLE 6

Hot-water swelling power of rice flours or rice starches of the single-gene approaches and of the triple combination

| Sample name | Hot-water swelling power of rice flours (g/g) | Hot-water swelling power of rice starches (g/g) |
|---|---|---|
| Wild type | 15.7 | 31.9 |
| oe-GWD-O.s.-4 | 21.6 | 38.6 |
| oe-GWD-O.s.-9 | 21.3 | 39.9 |
| oe-SSII-O.s.-01502 | 20.2 | 40.8 |
| 738-104/6 | 19.9 | 47.3 |
| XPOS025-01-1-37 | 40.6 | 86.0 |
| XPOS025-01-1-13 | 41.9 | 89.1 |
| XPOS026-01-1-19 | 38.3 | 87.2 |

The determination of the hot-water swelling power of flours or starches prepared from F4 seeds of the abovementioned lines and from wild-type plants was accomplished as described in "General Method".

The hot-water swelling power of the triple combination is markedly above that of the single-gene approaches.

Figure 1:
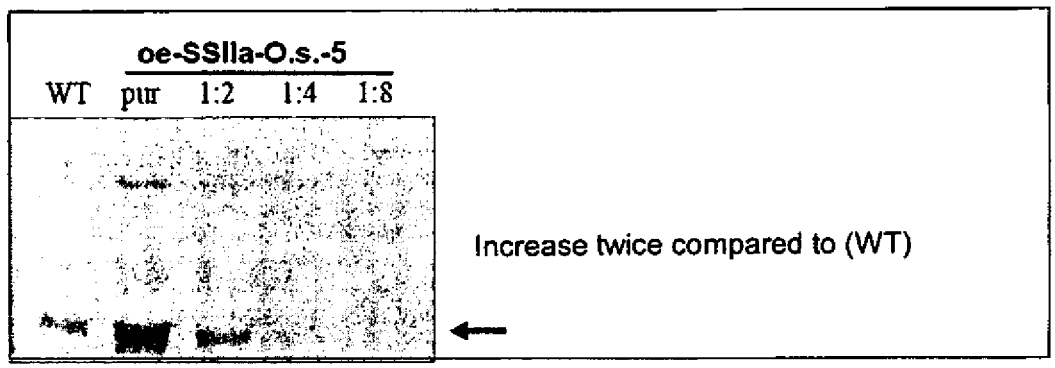
FIG. 1 shows zymograms for determining the activity of proteins with the activity of a starch synthase II in comparison with the wild type. The material used were total protein extracts from immature grains (15 days after anthesis) of wild-type plants (WT) and of the three independent genetically modified plants which are the result of the transformations with the expression vector AH32-191 (oe-SSII-O.s.-5, oe-SSII-O.s.-12, oe-SSII-O.s.-19). In the lanes WT and pur, in each case identical amounts of protein of the respective extracts are applied. The protein extracts of the genetically modified plants were subjected to serial dilution (1:2, 1:4, 1:6, 1:8, 1:10, 1:20, 1:50 or 1:100), and these dilutions were separated by electrophoresis, also separately from one another. The increase in the activity of a starch synthase II in comparison with wild-type plants can be determined by comparing the intensity of the specific products which are present in the zymogram after staining with Lugol's solution and which have been synthesized by a protein with the activity of a starch synthase II (identified by an arrow) of protein extracts from wild-type plants with the intensity of the corresponding bands of protein extracts from genetically modified plants. Equal intensities mean equal activities.
Figure 1:
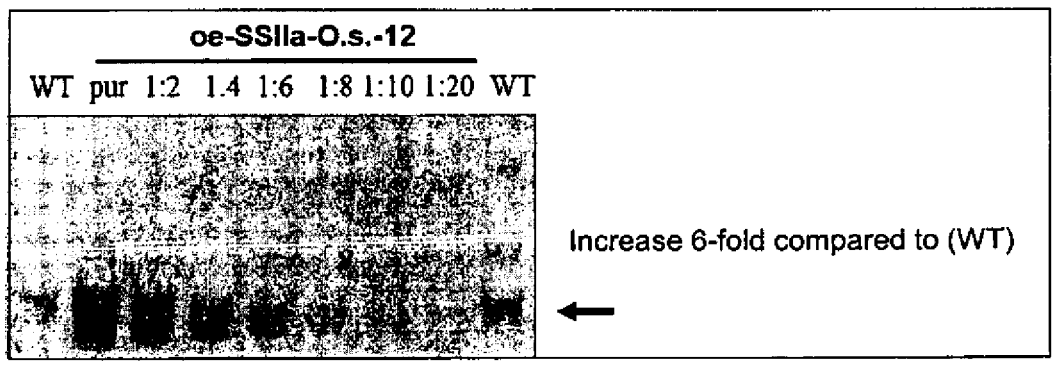
Figure 1:
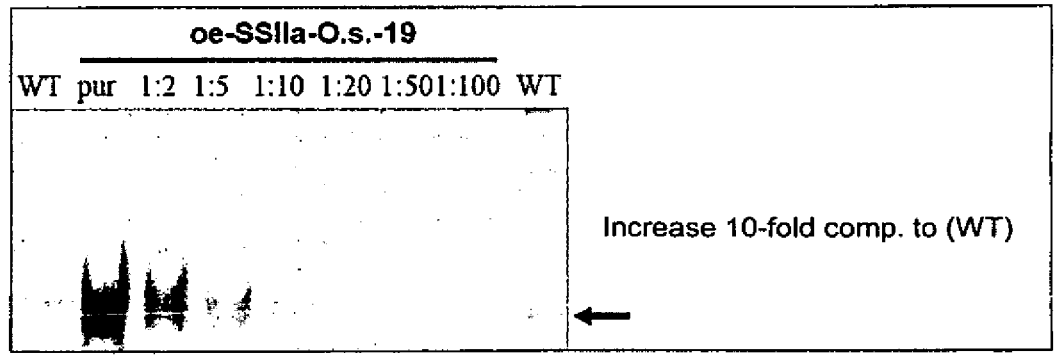
Figure 2:
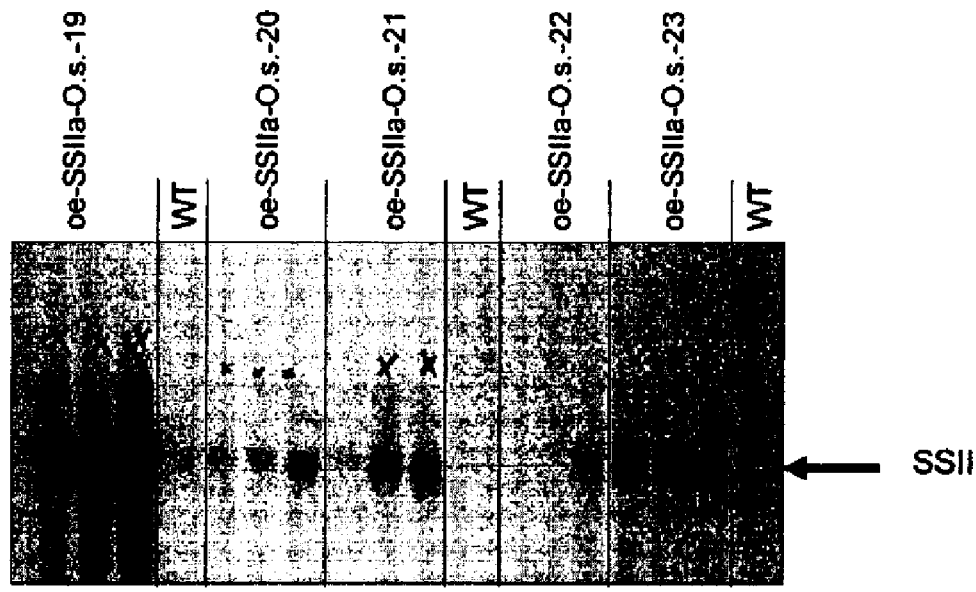
FIG. 2 shows the autoradiogram of a Northern blot analysis of immature T1 seeds of the rice lines oe-SSII-O.s.-19, oe-SSII-O.s.-20, oe-SSII-O.s.-21, oe-SSII-O.s.-22, oe-SSII-O.s.-23 in comparison with not genetically modified wild-type plants (WT). To this end, RNA was extracted from in each case three seeds of lines which have independently originated from the transformation with the expression vector AH32-191 and was analyzed in accordance with the method described in General Methods, item 8. The band which hybridizes with a labeled nucleic acid probe coding for a protein with the activity of a starch synthase II from wheat is identified as SSII.
Figure 3:
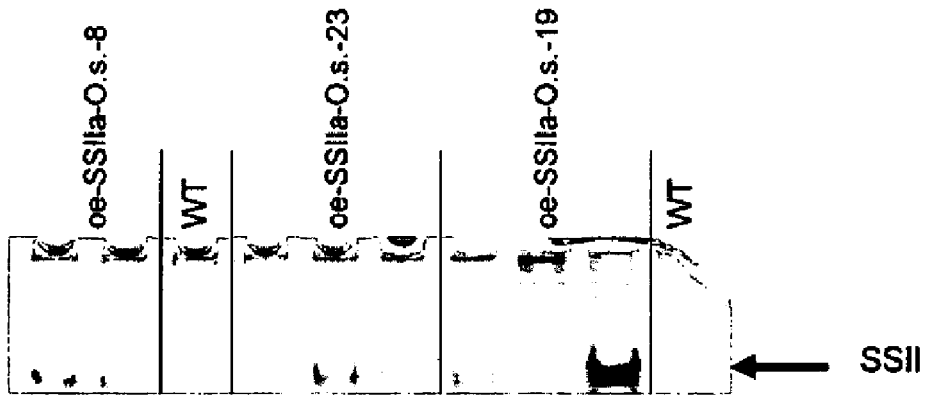
FIG. 3 shows a zymogram of protein extracts from immature T1 seeds of the rice lines oe-SSII-O.s.-8, oe-SSII-O.s.-19, oe-SSII-O.s.-23 in comparison with seeds of not genetically modified wild-type plants (WT) after staining with Lugol's solution. Protein extracts from two (oe-SSII-O.s.-8)

or three (oe-SSII-O.s.-19, oe-SSII-O.s.-23) different grains were analyzed per line. The analysis by means of zymogram was performed following the method described in General Methods, item 9. The band in the zymogram which is specific for a protein with the activity of a starch synthase II is identified as SSII.

We claim:

1. A genetically modified monocotyledonous plant cell that comprises a waxy mutation that results in the synthesis of a starch with an apparent amylose content of less than 5% by weight and that comprises a foreign nucleic acid molecule that increases the expression of a starch synthase II, and a foreign nucleic acid molecule that increases the expression of a glucan water dikinase, each compared to a corresponding monocotyledonous plant cell that does not comprise said foreign nucleic acid molecules, wherein said starch has a hot-swelling power of between 60 to 100 g/g.

2. A monocotyledonous plant comprising the genetically modified plant cell of claim 1.

3. The monocotyledonous plant of claim 2, wherein said plant is rice, maize or wheat.

4. A propagation material of monocotyledonous plants, wherein said propagation material comprises the genetically modified plant cell of claim 1.

5. A method of generating a genetically modified monocotyledonous plant, said method comprising the following steps:
   a) genetically modifying a monocotyledonous plant cell comprising the following steps:
      i) introducing, into the plant cell, a foreign nucleic acid molecule that increases the expression of a starch synthase II in comparison with a corresponding wild-type plant cell that does not comprise said foreign nucleic acid molecule,
      ii) introducing, into the plant cell, a foreign nucleic acid molecule that increases the expression of a glucan water dikinase in comparison with a corresponding wild-type plant cell that does not comprise said foreign nucleic acid molecule,
      iii) introducing, into the plant cell, a foreign nucleic acid molecule that reduces the expression of a GBSSI in comparison with a corresponding wild-type plant cells that does not comprise said foreign nucleic acid molecule,
      where steps i to iii can be carried out in any sequence, individually or simultaneously; and
   b) regenerating a plant from the plant cell of step a).

6. A process for the preparation of a modified starch, said process comprising the step of extracting the starch from the genetically modified plant cell of claim 1.

7. A process for the preparation of flours, said process comprising the step of grinding parts of the plant of claim 2.

8. The method of claim 5, further comprising the following steps:
   c) generating further plants by isolating plant cells from a plant of step b) and repeating steps a) and b); and
   d) repeating step c) until a plant has been generated which has an increased expression of a starch synthase II, an increased expression of a glucan water dikinase, and a reduced expression of a GBSSI, in comparison with a corresponding wild-type plant that has not been genetically modified by introducing the foreign nucleic acid molecules of claim 5.

9. A process for the preparation of flours, said process comprising the step of grinding parts of the propagation material of claim 4.

10. A process for the preparation of flours, said process comprising the step of grinding parts of the plants produced by the method of claim 5.

11. The genetically modified monocotyledonous plant cell of claim 1, wherein the plant cell comprises
   at least one foreign nucleic acid molecule encoding a starch synthase II; and
   at least one foreign nucleic acid molecule encoding a glucan water dikinase.

12. The genetically modified monocotyledonous plant cell of claim 11, wherein the at least one foreign nucleic acid molecule encoding a starch synthase II comprises:
   i) a nucleic acid molecule encoding a protein comprising the amino acid sequence of SEQ. ID. NOs.: 4 or 6;
   ii) a nucleic acid molecule comprising the nucleic acid sequence of SEQ. ID. NOs.: 3 or 5; or
   iii) a nucleic acid molecule that hybridizes under stringent conditions with at least one strand of the nucleic acid molecule described in ii), wherein the stringent conditions are:
   hybridization buffer: 2×SSC, 10×Denhardt solution (Ficoll 400+PEG+BSA; ratio 1:1:1), 0.1% SDS; 5 mM EDTA, 50 mM $Na_2HPO4$, 250 µg/ml of herring sperm DNA, 50 µg/ml of tRNA, or 25 M sodium phosphate buffer pH 7.2; 1 mM EDTA; 7% SDS;
   hybridization temperature: T=65 to 68° C.;
   wash buffer: 0.1×SSC; 0.1% SDS; and
   wash temperature: T=65 to 68° C.

13. The genetically modified monocotyledonous plant cell of claim 11, wherein the at least one foreign nucleic acid molecule encoding a glucan water dikinase comprises:
   i) a nucleic acid molecule encoding a protein comprising the amino acid sequence of SEQ. ID. NO.: 2;
   ii) a nucleic acid molecule comprising the nucleic acid sequence of SEQ. ID. NO.: 1; or iii) a nucleic acid molecule that hybridizes under stringent conditions with at least one strand of the nucleic acid molecule described in ii), wherein the stringent conditions are:
hybridization buffer: 2×SSC, 10×Denhardt solution (Ficoll 400+PEG+BSA; ratio 1:1:1), 0.1% SDS; 5 mM EDTA, 50 mM $Na_2HPO4$, 250 µg/ml of herring sperm DNA, 50 µg/ml of tRNA, or 25 M sodium phosphate buffer pH 7.2; 1 mM EDTA; 7% SDS;
hybridization temperature: T=65 to 68° C.;
wash buffer: 0.1×SSC; 0.1% SDS; and
wash temperature: T=65 to 68° C.

14. A genetically modified monocotyledonous plant cell comprising a foreign nucleic acid molecule that reduces the expression of an endogenous GBSSI, a foreign nucleic acid molecule that increases expression of a starch synthase II, and a foreign nucleic acid molecule that increases expression of a glucan water dikinase, each compared to a corresponding monocotyledonous plant cell that does not comprise said foreign nucleic acid molecules, wherein said plant cell synthesizes a starch having a hot-swelling power of between 60 to 100 g/g.

15. The genetically modified monocotyledonous plant cell of claim 14, wherein the foreign nucleic acid molecule that reduces the expression of an endogenous GBSSI comprises:
   i) a nucleic acid molecule encoding a protein comprising the amino acid sequence of SEQ. ID. NO.: 8, 10, or 12;
   ii) a nucleic acid molecule comprising the nucleic acid sequence of SEQ. ID. NO.: 7, 9, or 11; or
   iii) a nucleic acid molecule that hybridizes under stringent conditions with at least one strand of the nucleic acid molecule described in ii), wherein the stringent conditions are:
   hybridization buffer: 2×SSC, 10×Denhardt solution (Ficoll 400+PEG+BSA; ratio 1:1:1), 0.1% SDS; 5 mM EDTA, 50 mM $Na_2HPO4$, 250 µg/ml of herring sperm DNA, 50 µg/ml of tRNA, or 25 M sodium phosphate buffer pH 7.2; 1 mM EDTA; 7% SDS;
   hybridization temperature: T=65 to 68° C.;
   wash buffer: 0.1×SSC; 0.1% SDS; and
   wash temperature: T=65 to 68° C.

16. The genetically modified monocotyledonous plant cell of claim 14, wherein the foreign nucleic acid molecule that reduces the expression of an endogenous GBSSI comprises
   (i) a nucleic acid molecule encoding at least one antisense RNA that reduces the expression of at least one endogenous gene encoding a GBSSI protein;
   (ii) a nucleic acid molecule which, via a co-suppression effect, reduces the expression of at least one endogenous gene encoding a GBSSI protein; or
   (iii) a nucleic acid molecule that simultaneously encodes at least one antisense RNA and at least one sense RNA, where said antisense RNA and said sense RNA form a double-stranded RNA molecule that reduces the expression of at least one endogenous gene encoding a GBSSI protein.

17. A method of generating a genetically modified monocotyledonous plant comprising the following steps:
   a) genetically modifying a monocotyledonous plant cell that comprises a waxy mutation that results in the synthesis of a starch having an apparent amylose content of less than 5% comprising the following steps:
   i) introducing, into the plant cell, a foreign nucleic acid molecule that increases the expression of a starch synthase II in comparison with a corresponding wild-type plant cell that does not comprise said foreign nucleic acid molecule, and
   ii) introducing, into the plant cell, a foreign nucleic acid molecule that increases the expression of a glucan, water dikinase in comparison with a corresponding wild-type plant cell that does not comprise said foreign nucleic acid molecule
   where steps i to ii can be carried out in any sequence, individually or simultaneously; and
   b) regenerating a plant from the plant cell of step a).

* * * * *